US010857218B2

(12) United States Patent
Bordevik et al.

(10) Patent No.: US 10,857,218 B2
(45) Date of Patent: Dec. 8, 2020

(54) **ATTENUATED *PISCIRICKETTSIA SALMONIS* BACTERIUM**

(71) Applicant: PHARMAQ AS, Overhalla (NO)

(72) Inventors: Marianne Bordevik, Overhalla (NO); Anja Nygaard, Overhalla (NO); Siv Haugen Tunheim, Overhalla (NO); Marianne Froystad-Saugen, Overhalla (NO); Are Klevan, Overhalla (NO); Claudia Vargas Maira, Overhalla (NO)

(73) Assignee: PHARMAQ AS, Overhalla (NO)

( * ) Notice: Subject to any disclaimer, the term of this patent is extended or adjusted under 35 U.S.C. 154(b) by 19 days.

(21) Appl. No.: 15/576,352

(22) PCT Filed: May 25, 2016

(86) PCT No.: PCT/EP2016/061862
§ 371 (c)(1),
(2) Date: Nov. 22, 2017

(87) PCT Pub. No.: WO2016/189067
PCT Pub. Date: Dec. 1, 2016

(65) Prior Publication Data

US 2019/0091317 A1 Mar. 28, 2019

(30) Foreign Application Priority Data

May 26, 2015 (GB) .................................. 1509004.6

(51) Int. Cl.

| | |
|---|---|
| ***A01N 63/00*** | (2020.01) |
| ***A01N 65/00*** | (2009.01) |
| ***A61K 48/00*** | (2006.01) |
| ***A61K 45/00*** | (2006.01) |
| ***A61K 39/385*** | (2006.01) |
| ***A61K 47/00*** | (2006.01) |
| ***A61K 39/02*** | (2006.01) |
| ***C12N 1/36*** | (2006.01) |
| ***C12R 1/01*** | (2006.01) |
| ***C07K 14/195*** | (2006.01) |
| *A61K 39/00* | (2006.01) |
| *A61K 35/00* | (2006.01) |

(52) U.S. Cl.
CPC ........ *A61K 39/0208* (2013.01); *C07K 14/195* (2013.01); *C12N 1/36* (2013.01); *C12R 1/01* (2013.01); *A61K 2035/11* (2013.01); *A61K 2039/522* (2013.01); *A61K 2039/552* (2013.01)

(58) Field of Classification Search
CPC ........ A61K 35/12; A61K 35/74; A61K 39/39; A61K 39/0011; A61K 2039/522; C12N 15/86
See application file for complete search history.

(56) References Cited

FOREIGN PATENT DOCUMENTS

WO WO 2014/198913 A2 12/2014

OTHER PUBLICATIONS

Bowie et al., Science, 1990, 257:1306-1310 (Year: 1990).*
XP002761895, UNIPROT: A0A095BFK5, ATP-grasp domain protein sequence of Piscirickettsia salmonis strain PM32597B1. Nov. 26, 2014.
XP002761882, Millar, A. D. et al., "Piscirickettsia salmonis LF-89= ATCC VR-1361 strain LF-89, whole genome shotgun sequencing project," GenBank accession No. AMFF00000000.2 , Nov. 26, 2014.
Tamura, K. et al. "MEGA5: Molecular Evolutionary Genetics Analysis Using Maximum Likelihood, Evolutionary Distance, and Maximum Parsimony Methods," *Molecular Biology and Evolution* 28.10 (2011): pp. 2731-2739.
Rozas, M. et al., 2014, "Piscirickettsiosis and *Piscirickettsia salmonis* in fish: a review", Journal of Fish Diseases, vol. 37, pp. 163-188.

* cited by examiner

*Primary Examiner* — Gary B Nickol
*Assistant Examiner* — Lakia J Jackson-Tongue
(74) *Attorney, Agent, or Firm* — Vyacheslav Vasilyev

(57) ABSTRACT

The present invention relates to an attenuated *Piscirickettsia salmonis* bacterium. The bacterium comprises mutations in the amino acid sequence of each of the rpoD, FecR, ATP-grasp domain protein, and FtsH gene products. The invention also relates to vaccines comprising the attenuated *Piscirickettsia salmonis* bacterium that are useful for the prevention of microbial pathogenesis. In addition, the invention relates to methods for the preparation of attenuated *Piscirickettsia salmonis* bacteria, and vaccines comprising such bacteria.

7 Claims, 2 Drawing Sheets

Specification includes a Sequence Listing.

ATTENUATED *PISCIRICKETTSIA SALMONIS* BACTERIUM

CROSS REFERENCE TO RELATED APPLICATIONS

This application is a national stage, 35 U.S.C. § 371, of the international application PCT/EP2016/061862, filed May 25, 2016, which claims priority from GB1509004.6 filed May 26, 2015, the entire disclosures of which are hereby incorporated by reference in their entirety.

FIELD OF THE INVENTION

In the broadest aspect, the present invention relates to an attenuated bacterium, its preparation, and its use in a live attenuated vaccine.

BACKGROUND

Salmon Rickettsial Syndrome, "SRS", (also known as, Piscirickettsiosis, Coho salmon septicaemia, or Huito disease) is considered to be one of the most important disease problems facing the salmon farming industry. The bacterium *Piscirickettsia salmonis* is the causative agent of SRS.

SRS continues to evolve and new outbreaks continually occur which are increasingly insidious and refractory to treatments. New outbreaks frequently show increased bacterial virulence, clinical and pathological severity and variable presentation under similar conditions of species, age and management measures.

SRS has proven very difficult to control. The use of antibiotics, both prophylactically and during early infection, may inhibit the growth of the pathogen, but failure of antibiotic treatment is common, and antibiotic treatments have been largely unsuccessful in stopping disease outbreaks.

Thus, there is a need for improved methods of controlling *P. salmonis.*

Vaccines based on live but attenuated micro-organisms (live attenuated vaccines) induce a highly effective type of immune response. Generally, such vaccines induce stronger and more durable immunity than vaccines based on an inactivated pathogen as they activate all phases of the immune system. Specifically, once an animal host has been vaccinated with a live attenuated vaccine, entry of the microbial pathogen into the host induces an accelerated recall of earlier, cell-mediated and/or humoral immunity which is able to control the further growth of the organism before the infection can assume clinically significant proportions. Inactivated vaccines (based on killed micro-organisms or fragments of micro-organisms) are less likely to be able to achieve the same magnitude and rapidity of response.

There is thus a need for an attenuated strain of *P. salmonis*, suitable for use in a vaccine. The attenuated vaccine should substantially retain the antigenic capacity of the wild-type strain in order to cause a robust immune response in the host, and thereby provide strong immunity. The vaccine should also be sufficiently avirulent to minimise undesirable pathological effects. In addition, the live attenuated vaccine strain should have substantially no likelihood of reversion to a virulent form.

The general approach for attenuating bacteria is the removal of one or more virulence factors. In most cases however, virulence factors are required in order to induce immunity, and deletion of virulence factors unavoidably impairs the immunogenic capacities of the bacterium.

It has now surprisingly been found that by mutating the rpoD, FecR, ATP-grasp domain protein, and FtsH gene products, an attenuated *P. salmonis* bacterium can be produced, without impairing the viability or immunogenicity of such bacteria in vivo. By mutating a number of genes in parallel, the likelihood of reversion to a virulent form is minimised. Moreover, these genes were not previously known to relate to virulence factors, and it is therefore surprising that they have now been found to affect bacterial pathogenicity. This also offers the further advantage that the attenuated bacterium demonstrates substantially the same level of immunogenicity as wild-type strains. The disclosed bacterium has therefore surprisingly been found to be extremely suitable for use in the preparation of live attenuated vaccines.

SUMMARY

According to a first aspect, an attenuated *Piscirickettsia salmonis* bacterium is provided. The bacterium comprises a mutation in the amino acid sequence of each of the rpoD, FecR, ATP-grasp domain protein, and FtsH gene products.

The attenuated bacterium has a reduced virulence relative to wild-type *P. salmonis.* The attenuated bacterium is preferably avirulent and does not induce any symptoms of Salmon Rickettsial Syndrome when administered to fish.

The attenuated bacterium preferably does not revert to a virulent strain after serial passage in fish. For example, the attenuated bacterium preferably does not revert to a virulent strain after 2, 3, 4, 5, or 6 passages in fish.

The attenuated bacterium is preferably capable of inducing immunological protection against Salmon Rickettsial Syndrome when administered to fish. Indeed, the attenuated bacterium preferably provides protection to fish against SRS following subsequent challenge with a virulent strain of *P. salmonis*. Preferably, when measured in terms of accumulated mortality, the attenuated bacterium provides more than 40%, more than 50%, more than 60%, or more than 80% protection against SRS. Preferably, when measured in terms of accumulated mortality, the attenuated bacterium provides 100% protection against SRS.

The mutations in each of the rpoD, FecR, ATP-grasp domain protein, and FtsH genes of the attenuated bacterium, which underlie the mutations in the corresponding gene products, may be non-reverting mutations.

The mutations in the amino acid sequence of the rpoD, FecR, ATP-grasp domain protein, and FtsH gene products may be mutations relative to the sequence of the corresponding LF-89 wild-type protein, as derived from the LF-89 genomic sequence that is available under the GenBank accession no. AMFF00000000.2, and as provided as Seq. ID No.s 17, 26, 40, and 54, respectively.

The attenuated bacterium may comprise at least one mutation in 1, 2, 3, or all 4, of the following regions:

a) amino acid residues 462-504 of the rpoD gene product, provided as Seq. ID No. 17;
b) amino acid residues 39-137 of the FecR gene product, provided as Seq. ID No. 26;
c) amino acid residues 118-251 of the ATP-grasp domain protein gene product, provided as Seq. ID No. 40; and/or,
d) amino acid residues 152-274 of the FtsH gene product, provided as Seq. ID No. 54.

The attenuated bacterium may comprise 1, 2, 3, or all 4, of the following specific mutations:

a) an arginine to cysteine mutation at position 473 of the rpoD gene product, provided as Seq. ID No. 17;

b) a premature stop codon at the position corresponding to residue 83 of the FecR gene product, provided as Seq. ID No. 26;

c) a serine to proline mutation at position 184 of the ATP-grasp domain protein gene product, provided as Seq. ID No. 40; and/or, d) a methionine to isoleucine mutation at position 191 of the FtsH gene product, provided as Seq. ID No. 54.

The amino acid residue numbers given throughout are defined on the basis of the sequences of the corresponding LF-89 wild-type proteins, as shown in Example 2 (and given as Seq. ID No.s 17, 26, 40, 54), and derived from the LF-89 genomic sequence that is available under the GenBank accession no. AMFF00000000.2.

The attenuated bacterium may be the strain PHARMAQ 001 deposited with the European Collection of Cell Cultures, Public health England, Culture Collections, Porton Down, Salisbury SP4 OJG, United Kingdom, on 9 Oct. 2014 with accession number 14100901.

According to a second aspect, the invention provides a live, attenuated vaccine composition comprising:

(a) an attenuated *Piscirickettsia salmonis* bacterium of the first aspect; and (b) a pharmaceutically acceptable carrier or diluent.

The live, attenuated vaccine composition may be in freeze-dried form.

According to a third aspect, the invention provides a method of producing an attenuated bacterium in accordance with the first aspect. The method comprises:

1) subjecting an initial population of *P. salmonis* bacteria to attenuating conditions to produce a putatively attenuated bacterial population;

2) identifying clones of the putatively attenuated bacterial population that have mutations in the amino acid sequences of all of the rpoD, FecR, ATP-grasp domain protein, and FtsH gene products; and then, 3) identifying and selecting clones that have mutations in the amino acid sequence of all of the rpoD, FecR, ATP-grasp domain protein, and FtsH gene products and that also exhibit reduced virulence relative to wild-type bacteria of the genus *Piscirickettsia.*

According to a fourth aspect, the invention provides a method of raising an immune response in a fish. The method comprises administering to the fish an attenuated *Piscirickettsia salmonis* bacterium of the first aspect.

According to a fifth aspect, the invention provides a method of vaccinating a fish against Salmon Rickettsial Syndrome. The method comprises administering to a fish an immunologically-effective amount of a vaccine composition, said vaccine composition comprising an attenuated *Piscirickettsia salmonis* bacterium of the first aspect.

According to a sixth aspect, the invention provides an attenuated *Piscirickettsia salmonis* bacterium of the first aspect, for use in a method of vaccinating a fish.

According to a seventh aspect, the invention provides an attenuated *Piscirickettsia salmonis* bacterium of the first aspect, for use in a method of vaccinating a fish against Salmon Rickettsial Syndrome.

According to an eighth aspect, the invention provides a method of distinguishing the PHARMAQ 001 strain of *Piscirickettsia salmonis* from other strains such as wild-type strains. More specifically, the invention provides a method of distinguishing between wild-type and mutant alleles of a *Piscirickettsia salmonis* single nucleotide polymorphism (SNP) located at the position corresponding to:

residue number 1417 of Seq. ID No. 1 (in the rpoD gene);

residue number 247 of Seq. ID No. 4 (in the FecR gene);

residue number 550 of Seq. ID No. 7 (in the ATP-grasp domain protein gene); or, residue number 573 of Seq. ID No. 10 (in the FtsH gene).

The method comprises:

i) amplifying by PCR the region of the nucleotide sequence containing the SNP;

ii) including in the PCR reaction mix a nucleic acid probe having a sequence complementary to one allele of the SNP, the probe comprising a detectable marker; and iii) analysing the PCR product for the presence of the marker, wherein the presence of the marker is indicative of the presence of the allele.

The method may further comprise including in the PCR reaction mix a first nucleic acid probe having a sequence complementary to the wild-type allele of the SNP, and a second nucleic acid probe having a sequence complementary to the mutant allele of the SNP, the first and second probes comprising different detectable markers.

The probe may comprise a 10-40 nucleotide subsequence of:

Seq. ID No. 1, the subsequence including residue number 1417;

Seq. ID No. 4, the subsequence including residue number 247;

Seq. ID No. 7, the subsequence including residue number 550; or,

Seq. ID No. 10, the subsequence including residue number 573.

Specifically, the probe may comprise Seq. ID No. 68, 69, 72, 73, 76, or 77.

A PCR primer pair may be used in the method to amplify a region of at least 50 nucleotides in length of the subsequence of:

Seq. ID No. 1, the subsequence including residue number 1417;

Seq. ID No. 4, the subsequence including residue number 247;

Seq. ID No. 7, the subsequence including residue number 550; or,

Seq. ID No. 10, the subsequence including residue number 573.

Specifically, the PCR primer pair may comprise Seq. ID No. 67 and 70, 71 and 74, or 75 and 78.

DETAILED DESCRIPTION

*P. salmonis*

Figure 1:
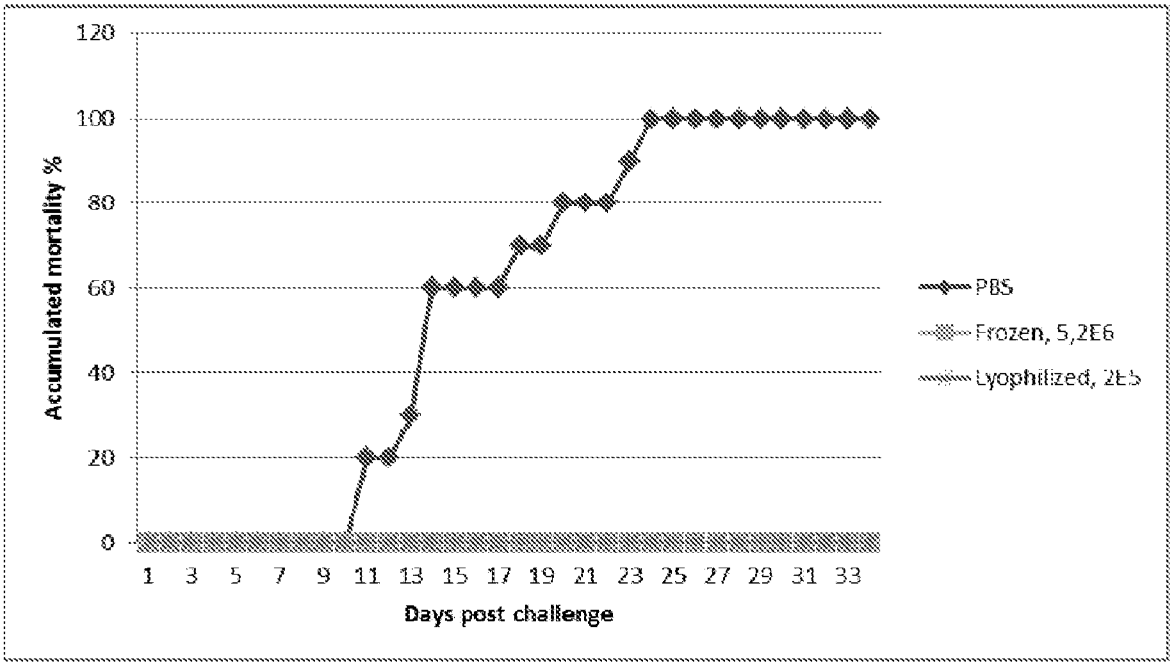
FIG. 1 shows the accumulated mortality following challenge with a virulent *P. salmonis* strain.

SRS is caused by the gram-negative bacterium, *Piscirickettsia salmonis*. This was the first "*rickettsia*-like" bacterium to be recognized as a pathogen of fish.

*P. salmonis* is generally non-motile, obligate intracellular bacterium, pleomorphic but predominately coccoid, and 0.5-1.5 μm in diameter. It is currently placed in the class Gammaproteobacteria; order Thiotrichales; and family Piscirickettsiacaea, and has a closer relationship to, e.g., *Legionella* and *Coxiella*, than to members of the genera *Rickettsia*. The bacterium replicates by binary fission within membrane bound cytoplasmic vacuoles in fish cell lines and in the cells of tissues throughout infected fish. The bacteria occur either singularly or in groups, giving the vacuole the appearance of a morula. When *P. salmonis* is examined by electron microscopy, the bacterium displays the typical protoplasmic structure of a prokaryote and the cell wall of a gram-negative bacterium.

The genome of *P. salmonis* strain LF-89 has been sequenced and published on at least three separate occasions (see, for example, Eppinger et al. Genome Announc. November/December 2013 vol. 1 no. 6), and is available via DDBJ/EMBL/GenBank under the accession no.s AMGC00000000.1, AMFF00000000.2, and ASSK00000000.2. Unless otherwise indicated, the LF-89 sequence used in the present application is the sequence available under the accession no. AMFF00000000.2. Specifically, unless otherwise indicated, for the purposes of genetic and protein sequence comparison in particular, this LF-89 sequence that is available under the GenBank accession no. AMFF00000000.2 is considered to represent the sequence of wild-type *P. salmonis*, and references to the wild-type in this context should be interpreted accordingly. The genomes of *P. salmonis* strains EM-90 (NCBI Reference Sequence: NZ_JRHP00000000.1), A1-15972 (NCBI Reference Sequence: NZ_JRAV00000000.2), and B1-32597 (NCBI Reference Sequence: NZ_JRAD00000000.2) have also been published.

Attenuated Bacterium

The attenuated *P. salmonis* bacterium of the invention is attenuated by means of a mutation in each of the rpoD, FecR, ATP-grasp domain protein, and FtsH genes. Specifically, the attenuated bacterium comprises genetic mutations which result in mutations in the amino acid sequence of each of the rpoD, FecR, ATP-grasp domain protein, and FtsH gene products, relative to the sequence of the wild-type proteins.

For the purposes of the invention, the term "gene product" is specifically considered to refer to the protein resulting from the expression of a gene.

For the purposes of the invention, a "mutation" is considered to be any alteration in the gene or protein sequence relative to the wild-type sequence. Genetic mutations that are of interest are those that result in a mutation (i.e. alteration) in the resulting amino acid sequence of the gene product relative to the wild-type amino acid sequence. Each of the mutations in the rpoD, FecR, ATP-grasp domain protein, and FtsH genes can be any type of mutation, including an insertion, a deletion, a substitution, or any combination of these, provided that the mutation leads to a change in the amino acid sequence of each of the rpoD, FecR, ATP-grasp domain protein, and FtsH gene products, relative to the wild-type protein sequence.

A functional gene product is a protein having the functional characteristics of the wild-type protein. A rpoD, FecR, ATP-grasp domain protein, or FtsH gene product that is at least partially defective in at least one of its functions is considered to be an attenuated gene product. Any mutation resulting in an attenuated gene product is considered to be an attenuating mutation. The mutations in the amino acid sequence of each of the rpoD, FecR, ATP-grasp domain protein, and FtsH gene products, relative to the wild-type proteins, are preferably attenuating mutations.

Attenuating mutations in the rpoD, FecR, ATP-grasp domain protein, and FtsH gene products may knock-out the function of the gene product partially or completely. The partial or total functional knock-out may be achieved, for example, by making a mutation that results in the synthesis of non-functional or partially functional polypeptide. For example, the mutation in the amino acid sequence may comprise the insertion of a stop codon, or may result in the incorporation of an amino acid that is physically or chemically dissimilar to the wild-type residue. Such mutations may result in the production of a truncated protein, a misfolded protein, or a chemically inactive protein, for example.

The mutations in each of the rpoD, FecR, ATP-grasp domain protein, and FtsH genes, which result in mutated gene products, are preferably non-reverting mutations. These are mutations that show essentially no reversion back to the wild-type when the bacterium is used as a vaccine.

The possibility of reversion of the bacterium to full virulence is also eliminated by the fact the bacterium contains attenuating mutations in four independent genes.

Attenuated Genes

The gene rpoD encodes RNA polymerase sigma factor, which is an initiation factor involved in promoting the attachment of RNA polymerase to specific transcription initiation sites. The rpoD gene product is believed to be involved in in the regulation of essential housekeeping genes. For the avoidance of doubt, the wild-type *P. salmonis* rpoD gene sequence that is mutated in the present invention is given as Seq. ID No. 1, and the gene can be identified using the PCR primers of Seq. ID No.s 2 and 3. The amino acid sequence of the full-length wild-type protein is given in Seq. ID No.s 14-17. The attenuated bacterium of the invention comprises a mutation in the amino acid sequence of the rpoD gene product, relative to the sequence of the wild-type protein, which is exemplified by the LF-89 sequence, given as Seq. ID No. 17.

The gene FecR encodes an iron dicitrate transport regulator. The FecR gene product is believed to be involved in regulating a number of genes involved in the uptake of iron and citrate. For the avoidance of doubt, the wild-type *P. salmonis* FecR gene sequence that is mutated in the present invention is given as Seq. ID No. 4, and the gene can be identified using the PCR primers of Seq. ID No.s 5 and 6. The amino acid sequence of the full-length wild-type protein is given in Seq. ID No.s 26-29. The attenuated bacterium of the invention comprises a mutation in the amino acid sequence of the FecR gene product, relative to the sequence of the wild-type protein, which is exemplified by the LF-89 sequence, given as Seq. ID No. 26.

The ATP-grasp domain protein gene encodes a protein with similarity to an alpha-L-glutamate ligase-related protein found in *Pseudomonas* (GenBank accession No. AP 014655.1). For the avoidance of doubt, the wild-type *P. salmonis* ATP-grasp domain protein gene sequence that is mutated in the present invention is given as Seq. ID No. 7, and the gene can be identified using the PCR primers of Seq. ID No.s 8 and 9. The amino acid sequence of the full-length wild-type protein is given in Seq. ID No.s 40-43. The attenuated bacterium of the invention comprises a mutation in the amino acid sequence of the ATP-grasp domain protein gene product, relative to the sequence of the wild-type protein, which is exemplified by the LF-89 sequence, given as Seq. ID No. 40.

The gene FtsH encodes an ATP-dependent zinc metalloprotease, which acts as a processive, ATP-dependent zinc metallopeptidase for both cytoplasmic and membrane proteins. The FtsH gene product is also believed to play a role in the quality control of integral membrane proteins. For the avoidance of doubt, the wild-type *P. salmonis* FtsH gene sequence that is mutated in the present invention is given as Seq. ID No. 10, and the gene can be identified using the PCR primers of Seq. ID No.s 11 and 12. The amino acid sequence of the full-length wild-type protein is given in Seq. ID No.s 54-57. The attenuated bacterium of the invention comprises a mutation in the amino acid sequence of the FtsH gene product, relative to the sequence of the wild-type protein, which is exemplified by the LF-89 sequence, given as Seq. ID No. 54.

In some embodiments, one or more of the rpoD, FecR, ATP-grasp domain protein, and FtsH gene products are entirely knocked-out, with the effect that no functional protein is detectable. Thus, the mutation in the amino acid sequence of the gene product is that there is no amino acid sequence.

In other embodiments, the mutation may comprise the introduction of a stop codon.

In some embodiments, the genes may be expressed at wild-type levels, but mutated so that the gene products have a different amino acid sequence to that found in wild-type strains. The genetic mutation may result in a deletion, an insertion, and/or a substitution of one or more amino acids in the gene product. The genetic mutation may result in full-length or substantially full-length gene products, or truncated gene products. The mutation may be a point mutation, affecting just one amino acid, or may affect more than one amino acid residue, such as, for example, affecting 2-20 residues, 3-15 residues, 4-12 residues, or 5-10 residues.

For example, in one embodiment of the invention, the rpoD gene is mutated resulting in the replacement of arginine with cysteine at position 473 in the amino acid sequence of the gene product. As a result of this mutation, the protein encoded by the mutated rpoD gene has different functional properties to those of the wild-type protein.

In one embodiment of the invention, the FecR gene is mutated resulting in the insertion of a premature stop codon, for example, in the position of residue 83, and therefore the production of a truncated gene product, having different functional properties to those of the wild-type protein.

In one embodiment of the invention, the ATP-grasp domain protein gene is mutated resulting in the replacement of serine with proline at position 184 in the amino acid sequence of the gene product. As a result, the mutated ATP-grasp domain protein has different functional properties to those of the wild-type protein.

In one embodiment of the invention, the FtsH gene is mutated resulting in the replacement of methionine with isoleucine at position 191 in the amino acid sequence of the gene product. As a result, the protein encoded by the mutated FtsH gene has different functional properties to those of the wild-type protein.

In some embodiments, two, three, or all four, of the specific point mutations described above in the rpoD, FecR, ATP-grasp domain protein, and FtsH genes may be present in combination. For example, in one embodiment, the attenuated bacterium comprises the specific point mutations described above in three of the rpoD, FecR, ATP-grasp domain protein, and FtsH genes, and the fourth gene has a different mutation to that described above. In one embodiment, the attenuated bacterium comprises all four of the specific point mutations described above in the rpoD, FecR, ATP-grasp domain protein, and FtsH genes.

The bacterium preferably contains only defined mutations, which are fully characterised. It is less preferred to use a bacterium which has uncharacterised mutations in its genome as a vaccine because there would be a risk that the uncharacterised mutations may confer properties on the bacterium that cause undesirable side-effects.

Production of Attenuated *P. salmonis*

In another aspect of the present invention, the invention provides methods for identifying and/or producing attenuated *P. salmonis* clones.

The methods according to this aspect of the invention include subjecting an initial population of *P. salmonis* bacteria to attenuating conditions, thereby producing a putatively attenuated bacterial population.

According to this aspect of the invention, the "initial population of *P. salmonis* bacteria" can be any quantity of *P. salmonis* bacteria. The bacteria, in certain embodiments are wild-type *P. salmonis* bacteria. A number of strains of *P. salmonis* have been isolated following outbreaks of SRS. Any of these isolated strains would potentially be suitable as a starting population for producing a putatively attenuated bacterial population, including the following strains: AL 10 016, AL 10 008, AL 20 218, AL 20 219, AL 20 223, AL 20 220, AL 20 470, AL 20 471, AL 20 455, AL 20 222, A1-15972, B1-32597, LF-89, EM-90. References to wild-type *P. salmonis* may refer to any of these strains. Preferably, however, references to wild-type *P. salmonis* refer to any of strains A1-15972, B1-32597, LF-89, or EM-90, such as in particular, strains A1-15972, LF-89, or EM-90. Unless otherwise indicated, however, for the specific purposes of genetic and protein sequence comparison, the LF-89 sequence that is available under the GenBank accession no. AMFF00000000.2 is considered to represent the sequence of wild-type *P. salmonis*, and references to the wild-type in this context should be interpreted accordingly.

The bacteria used as a starting population for producing a putatively attenuated bacterial population may alternatively contain one or more mutations relative to the wild-type, or other strain.

Preferably, the bacteria in the initial population are clonally identical or substantially clonally identical. In other words, the bacteria are preferably all derived from a single parental *P. salmonis* bacterial cell and/or have identical or substantially identical genotypic and/or phenotypic characteristics.

The term "attenuating conditions" refers to any condition or combination of conditions which has or have the potential for introducing one or more genetic changes (i.e., mutations) into the genome of a *P. salmonis* bacterium. Exemplary, non-limiting, attenuating conditions include, for example, passaging bacteria in culture, transforming bacteria with a genome-insertable genetic element such as a transposon (e.g., a transposon that randomly inserts into the *P. salmonis* genome), exposing bacteria to one or more mutagens (e.g., chemical mutagens or ultraviolet light), and any other suitable methods.

Indeed, the attenuating mutations may be introduced by any suitable method. A possibility to introduce a mutation at a predetermined site, deliberately rather than randomly, is offered by recombinant DNA-technology. Such a mutation may be an insertion, a deletion, a replacement of one or more nucleotides, or any combination of these, with the only proviso that the genetic mutation leads to a mutation in the amino acid sequence of the resulting gene product.

For example, one possible method includes cloning the DNA sequence of the wild-type gene into a vector, such as a plasmid, and inserting a selectable marker into the cloned DNA sequence or deleting a part of the DNA sequence, resulting in its inactivation. A deletion may be introduced by, for example, cutting the DNA sequence using restriction enzymes that cut at two points in or just outside the coding sequence and ligating together the two ends in the remaining sequence. A plasmid carrying the inactivated DNA sequence can be transformed into the bacterium by known techniques such as electroporation and conjugation. It is then possible by suitable selection to identify a mutant wherein the inactivated DNA sequence has recombined into the chromosome of the bacterium and the wild-type DNA sequence has been rendered non-functional by homologous recombination.

In some embodiments, one or more further mutations may be introduced into the bacteria to generate strains containing mutations in genes in addition to those in the rpoD, FecR, ATP-grasp domain protein, and FtsH genes.

When bacterial cells are attenuated by passaging in vitro, the cells may be passaged any number of times, such as for example, at least 10, 20, 40, 60, 80, 100, 120, or more times in vitro.

The initial population of *P. salmonis*, after being subjected to attenuating conditions, is referred to as a putatively attenuated bacterial population. Individual clones of the putatively attenuated bacterial population can be obtained by standard microbiological techniques including, for example, serially diluting the cells and plating out individual cells on appropriate media.

Once obtained, the individual clones of the putatively attenuated bacterial population are assayed for mutations in each of the rpoD, FecR, ATP-grasp domain protein, and FtsH genes. The mutated gene sequences are then analysed to determine whether the resulting amino acid sequences have any mutations. Mutations in the amino acid sequences of the gene products are considered to be any differences in the amino acid sequences compared to the wild-type *P. salmonis* sequence.

Any suitable method may be used to determine whether a putatively attenuated *P. salmonis* bacterium exhibits mutations in each of the rpoD, FecR, ATP-grasp domain protein, and FtsH genes, and consequently any mutations in the amino acid sequence of any of the rpoD, FecR, ATP-grasp domain protein, and FtsH gene products.

One method by which mutations in these genes may be identified is by amplifying and sequencing portions of the genes. Any suitable PCR method may be used to amplify portions of the genes and pairs of PCR primers suitable for amplifying specific portions of the rpoD, FecR, ATP-grasp domain protein, and FtsH genes are given in Seq. ID No.s: 2 and 3; 5 and 6; 8 and 9; and 11 and 12, respectively. The amino acid sequence of the gene product can be determined from the genetic sequence using any suitable computational tool.

For the avoidance of doubt, the primers given in Seq. ID No.s: 2 and 3; 5 and 6; 8 and 9; and 11 and 12, may also be used to identify the genes referred to as rpoD, FecR, ATP-grasp domain protein, and FtsH respectively.

The portions of the genes amplified using the PCR primers of Seq. ID No.s: 2 and 3; 5 and 6; 8 and 9; and 11 and 12 are regions of the genes, which when mutated, have been found to be particularly associated with the attenuation of the bacteria. Specifically, differences between the amino acid sequences of these portions of the rpoD, FecR, ATP-grasp domain protein, and FtsH gene products, and the wild type sequences, may be indicative of attenuating mutations in the gene products. Therefore, in some embodiments, references to mutations in the amino acid sequence of the rpoD, FecR, ATP-grasp domain protein, and FtsH gene products preferably refer to the presence of mutations in the amino acid sequence of those portions of the gene products corresponding to the regions that may be amplified by the PCR primers of Seq. ID No.s: 2 and 3; 5 and 6; 8 and 9; and 11 and 12.

Differences in the amino acid sequences of the rpoD, FecR, ATP-grasp domain protein, and FtsH gene products between the putatively attenuated and wild-type *P. salmonis* bacteria may in some cases not be accompanied by reduced function of the gene product. For the purposes of the invention, such mutations are not considered to be attenuating mutations. Non-attenuating mutations may be found in the portions of the gene products corresponding to the regions amplified using the PCR primers of Seq. ID No.s: 2 and 3; 5 and 6; 8 and 9; and 11 and 12, or elsewhere in the genes.

In some embodiments, some (such as 1, 2, or 3) of the rpoD, FecR, ATP-grasp domain protein, and FtsH gene products may include attenuating mutations, while the remainder of the rpoD, FecR, ATP-grasp domain protein, and FtsH gene products contain non-attenuating mutations.

The clones that have been identified as having mutations in the amino acid sequence of each of the rpoD, FecR, ATP-grasp domain protein, and FtsH gene products, relative to the wild-type sequence, are then tested for virulence.

Individual clones that are identified as having mutations in the amino acid sequence of each of the rpoD, FecR, ATP-grasp domain protein, and FtsH gene products can be tested for virulence by any suitable method. For example, the attenuated bacteria may be administered to an animal that is susceptible to infection by the wild-type version of the bacterium, and the presence and severity of disease determined.

In the present context, "an animal that is susceptible to infection by a wild-type *P. salmonis* bacterium" is an animal that shows at least one clinical symptom after being challenged with a wild-type *P. salmonis* bacterium. Such symptoms are known to persons of ordinary skill in the art. For example, in the case of a putatively attenuated *P. salmonis* strain that exhibits mutations in the amino acid sequence of each of the rpoD, FecR, ATP-grasp domain protein, and FtsH gene products, the strain can be administered to, for example, salmon (which are normally susceptible to infection by wild-type *P. salmonis*). Clinical symptoms of SRS in salmon are known to the skilled person.

In some embodiments, the symptoms investigated may include the accumulated mortality of a population. If the accumulated mortality is lower in animals challenged with the putatively attenuated *P. salmonis* strain, compared to fish that have been infected with a wild-type *P. salmonis* strain, then the putatively attenuated *P. salmonis* strain is deemed to have reduced virulence.

In some embodiments, the symptoms investigated may include the presence or accumulation or *P. salmonis* genomes in tissue samples taken from animals challenged with the putatively attenuated *P. salmonis* strain. If the presence of *P. salmonis* DNA is reduced compared to fish that have been infected with a wild-type *P. salmonis* strain, then the putatively attenuated *P. salmonis* strain is deemed to have reduced virulence.

Thus, if the putatively attenuated *P. salmonis* strain, when administered to salmon, results in fewer and/or less severe symptoms when compared to fish that have been infected with a wild-type *P. salmonis* strain, then the putatively attenuated *P. salmonis* strain is deemed to have "reduced virulence". Any degree of reduction in any relevant symptoms will identify the putatively attenuated strain as having reduced virulence.

For the purposes of the invention, any strain that is found to have a reduced virulence is considered to be an attenuated strain. In preferred embodiments, the putatively attenuated strain is avirulent.

Clones that exhibit mutations in the amino acid sequence of each of the rpoD, FecR, ATP-grasp domain protein, and FtsH gene products, and that also exhibit reduced virulence relative to wild-type *P. salmonis* are identified as attenuated *P. salmonis* clones of the present invention.

An exemplary, live, attenuated *P. salmonis* clone of the present invention, which exhibits non-reverting genetic mutations resulting in mutations in the amino acid sequence of each of the rpoD, FecR, ATP-grasp domain protein, and FtsH gene products is the strain designated PHARMAQ 001.

Specifically, relative to wild-type *P. salmonis*, PHARMAQ 001 has been found to have mutations located at positions corresponding to:

- residue number 1417 of Seq. ID No. 1 (in the rpoD gene);
- residue number 247 of Seq. ID No. 4 (in the FecR gene);
- residue number 550 of Seq. ID No. 7 (in the ATP-grasp domain protein gene); and,
- residue number 573 of Seq. ID No. 10 (in the FtsH gene).

For the purpose of the present disclosure, the mutations found in the *P. salmonis* strain PHARMAQ 001 are considered to represent single nucleotide polymorphisms (SNP). Various methods of distinguishing between SNP alleles are known to the skilled person, and can be used to determine whether a given strain is PHARMAQ 001. In particular, various different methods have been developed for the detection of specific alleles, or DNA sequence variants, at the same locus by polymerase chain reaction. For example, suitable methods may be based on the use PCR primers with a 3' end specific for one of the allelic variants, or on the use of nucleic acid probes having a sequence complementary to the sequence of one particular individual allelic variant.

PHARMAQ 001 has been deposited with the European Collection of Cell Cultures, Public health England, Culture Collections, Porton Down, Salisbury SP4 OJG, United Kingdom, on 9 Oct. 2014 and was assigned accession number 14100901.

Vaccine

A vaccine comprising the disclosed attenuated bacterium may be formulated using known techniques.

It has now surprisingly been found that an attenuated *P. salmonis* bacterium having a combination of mutations in the the amino acid sequences of the rpoD, FecR, ATP-grasp domain protein, and FtsH gene products gives a vaccine having superior properties for at least two reasons.

Firstly, due to the presence of multiple mutations in four independent genes there is a significantly reduced chance of reversion of attenuation of the bacterium. Therefore, the bacterium can survive in the vaccinated host for a long time and at high levels, resulting in better protection.

Secondly, the disclosed bacterium does not cause reduced immunogenicity compared to wild type strains because antigens important for immunogenicity are still expressed.

The vaccine composition preferably comprises a live, attenuated *P. salmonis* bacterium and a pharmaceutically acceptable carrier.

Examples of pharmaceutically acceptable carriers or diluents useful in the present invention include water, a preservative, culture medium, stabilisers such as SPGA, carbohydrates (e.g. sorbitol, mannitol, starch, sucrose, glucose, dextran), proteins such as albumin or casein, protein containing agents such as bovine serum or skimmed milk, and buffers (e.g. phosphate buffer).

The vaccine may or may not comprise an adjuvant. Adjuvants are non-specific stimulators of the immune system. They enhance the immune response of the host to the vaccine. Examples of adjuvants known in the art are Freunds Complete and Incomplete adjuvant, vitamin E, non-ionic block polymers, muramyldipeptides, ISCOMs (immune stimulating complexes), Saponins, mineral oil, vegetable oil, and Carbopol.

Vaccine formulations comprising the disclosed attenuated bacterium can be prepared in the form of a suspension or in a lyophilized form or, alternatively, in a frozen form. If the formulation is to be frozen, glycerol or other similar agents may be included in the formulation to enhance the stability of the bacterium when frozen.

Reconstitution is advantageously effected in a buffer at a suitable pH to ensure the viability of the bacteria.

The combined administration of several vaccines is desirable, in order to save time, effort, and money. Preferably, vaccine formulations comprising the disclosed attenuated bacterium may be used together with other vaccines, such as, for example, an inactivated, oil adjuvanted vaccine. The vaccines may be administered together, for example, in a single composition, or separately.

Vaccinated Species

The animal to which the vaccine comprising the disclosed attenuated bacterium is administered is preferably a fish. The vaccine may be administered to any species of fish that is susceptible to SRS infection.

Of particular note, the vaccine is suitable for treating fish of the order Samoniformes. For example, the claimed formulation may be used to treat salmon such as Atlantic and Pacific salmon, such as Coho salmon, and trout such as rainbow trout and brown trout.

Method of Vaccination

The present invention includes methods of vaccinating fish against *P. salmonis* infection, such as SRS.

The methods according to this aspect of the invention comprise administering to a fish an immunologically-effective amount of a vaccine composition comprising a live, attenuated *P. salmonis* bacterium of the invention. The expression "immunologically-effective amount" means the amount of vaccine composition required to invoke the production of protective levels of immunity in a host upon vaccination.

The vaccine composition may be administered to the host in any manner known in the art. In particular, the vaccine formulation may be suitable for parenteral administration, such as by intraperitoneal injection.

An infection caused by a microorganism, especially a pathogen, may therefore be prevented by administering an effective dose of a vaccine prepared according to the invention.

The dosage of the vaccine employed will be dependent on various factors including the size and weight of the host, the type of vaccine formulated, and the formulation.

For example, a dosage for Atlantic salmon, Coho salmon or rainbow trout, with an average weight of 25-30 grams, may comprise the administration of from $1\times10^2$ to $1\times10^{10}$, $1\times10^3$ to $1\times10^9$, or $1\times10^4$ to $1\times10^8$ $TCID_{50}$ per fish, such as from $1\times10^4$ to $1\times10^7$ $TCID_{50}$ per fish. As the skilled person will appreciate, the preferred dosage may depend on the age, weight and type of fish to be vaccinated, and the mode of administration. For example, dosages may need to be increased for larger, more robust fish, and decreased for smaller, more delicate fish.

EXAMPLES

The invention will now be explained in further detail in the following Examples, which demonstrate the development of the claimed live, attenuated bacterium, and its use in a vaccine.

Example 1: Isolation of the PHARMAQ 001 Strain and Attenuation of the Strain

The *P. salmonis* strain used as the starting bacterial population for the production of an attenuated bacterium was a strain originally isolated from an outbreak of SRS in Atlantic salmon in the X region in Chile.

The isolate was for the six first passages cultivated in the presence of eukaryotic cells.

For the next passages until passage 104, the *P. salmonis* isolate was cultivated in cell free insect cell medium at 20° C. To secure a homogenous culture, the passage 104 culture was serially diluted in insect cell medium and seeded into 96 well cell culture plates. Bacteria grown in chosen wells were further passed into new wells at an early stage when it was most likely that the growth originated from a single bacterium.

After a total of 111 passages, one clone from the wells was inoculated into a spinner flask and cultivated in insect cell medium. This passage was used as the origin of the putatively attenuated bacterial population, and the isolate was named "PHARMAQ 001", which corresponds to passage 113.

The bacterial isolate was verified to be *P. salmonis* using a commercial kit "SRS Fluorotest Directo" from Bios Chile, Chile.

PHARMAQ 001 has been deposited with the European Collection of Cell Cultures, Public health England, Culture Collections, Porton Down, Salisbury SP4 OJG, United Kingdom, on 9 Oct. 2014 and was assigned accession number 14100901.

Example 2: Analysis of PHARMAQ 001

The genomes of PHARMAQ 001 and the virulent starting strain were sequenced and the sequences were compared.

Genetic differences between the two strains, i.e. mutations accumulated by the PHARMAQ 001 strain during its production, were identified.

Because these genetic differences underpin the observed differences in the virulence of PHARMAQ 001 and the starting strain, mutations were identified in PHARMAQ 001 that resulted in a significant change in the amino acid sequence of the encoded protein. Specifically, four significant mutations in PHARMAQ 001 relative to the starting strain were identified. The identity of the four genes was determined, and the genes were found to be rpoD, ATP-grasp domain protein, and FtsH (all annotated by the IGS Prokaryotic Annotation Pipeline), and FecR (GenBank reference: KGB63484.1)

PCR primers were designed to allow the specific region of each of the rpoD, ATP-grasp domain protein, FtsH, and FecR genes containing the identified mutation to be amplified. In each of the gene sequences shown below, the mutation is shown in bold and underlined, and the primer binding sites are highlighted in grey and underlined.

PHARMAQ 001 rpoD gene sequence (Seq. ID No. 1):

ATGGATCAACAAGAAAAAAGGTCGCAGTTTAAAGAACTCATTGTTCGAG

GTAAACAGCAAGGCTTTTTAACGTTTACAGAGGTAAACGATCATCTTCC

GGATGATATGAGCAGCCCGGAAGAAGTTGAAGAGATCGTTGCAATGATT

AGCGACATGGGCATCCCCGTCTATGAAACTGCACCCGATCCTGACAGCT

-continued

TACTCATGAATGAGCATGCCAGCTCTGCCGAAGATGATGCTGACGATGC

CGTTGCAGCGCTCGATTCAGATGCTGAGTTTGGGCGAACAACCGACCCA

GTACGCATGTATATGCGCGAGATGGGCAGCGTTGAGCTATTAACGCGCC

AAGGTGAAATTGAGCTGGCTAAACGCATCGAGGAAGGCGTCAAACAAGC

CTTTGAGGCAATCGCCCATTACCCACAAAGCACAGCGATTATTCTTGAA

GAATATGCAAGATTTGAAGCCGAAGAAATCCGTTTAGATGATATTATCA

GTGGCTATATCACCGAAGAAGATGAAGCTCCGACAAGCAACATCGGCTC

CATGCTTGATGATGCCAATAAAGCCGATGATAATTTTGAAGCCGCCTTG

ACAGAAGACGACAGTACTGATGACGGTGAGGGTGAGGATGACAATGAAG

AAATCCCCGTCGATAACACATTGGATGTTGAGGAAGCGGCAGAGCGTTT

TGCCGAGCTAAAAGCTGCCTATGATGCGGTTATACAGGTTCAGGAAAAA

CACGGAATTCATCATAAAAAAACACAACAGCGTTGTGAAGAACTGTCTA

AAGTATTAATGACATTTCGCCTAAAGCCCAATATGATCGATAAAATCAC

CAACTACTTACATGGCTTACTCAGCCAAGTCCGCAAACATGAGCGTCAC

ATCATGGCTTTGTGCATTAATCAAGCGAAAATGCCCCGCAAGCTATTTA

TTGATATTTTCCCAGGCAATGAAACCAATCTAGAGTGGATAGAGTATCA

AATTAAAGCCGAGCAATCTTACTCTGAAGCACTACAGTCCCTGGCTCCA

GAAGTCACTCGTGCACAGAAAAAGCTCATCTCTCTTGAACAAGAATCAA

ACTTTGATGTCACTGCAATTAAAGAAGTCAATCGTAATATTTCTATTGG

TGAGGCCAAGGCCCATCGTGCTAAAAAAGAAATGGTCGAAGCTAACTTG

CGTCTGGTCATCTCCATTGCAAAAAAATACACCAATCGAGGCTTACAAT

TTCTCGACCTCATTCAAGAAGGCAATATTGGCCTAATGAAAGCGGTAGA

TAAATTCGAATACCGCCGTGGTTATAAATTCTCAACGTATGCAACATGG

TGGATTCGCCAGGCAATTACCCGCTCAATTGCTGATCAAGCGCGGACAA

TCCGGATTCCTGTACATATGATAGAGACAATTAACAAGCTTAACTGCGT

CTCACGTCAAATGATCCAAGAACTCGGCCGTGAAGCGACTCCTGAGGAG

CTTTCTGAACGCATGGAGATGCCAGAGCATAAAATCCGTAAAATCCTCA

AAATCGCTAAAGAGCCAATTTCTATGGAAACACCGATTGGCGATGACGA

AGATTCACACTTAGGTGATTTTATTGAAGATACCACCATGCAACTCCCC

GTTGACTCAACCATGGGTGATGCGTTAAAGCAAGCCACCAGTGATATTC

TCGAAAACCTCACGCCACGTGAAGCAAAAGTCCTTAGAATGCGCTTTGG

TATCGATATGAATACTGACCATACGCTAGAGGAAGTTGGCAAACAATTT

GACGTAACTCGCGAGCGTATTCGCCAAATTGAAGCCAAAGCCTTACGTA

AACTGCGCCACCCAACTCGCTCAGAAATTTTGAAGAGTTTTCTTGACTC

AGAAGAATAA

PCR Primers:

Forward rpoD (Seq. ID No. 2):
CCAGGCAATTACCCGCTCAA

Reverse rpoD (Seq. ID No. 3):
TCGCCAATCGGTGTTTCCAT

PHARMAQ 001 FecR gene sequence (Seq. ID No. 4):

ATGAAAATTAATCATCAGCCTGGCGGCATAATGTTGATAATGAATAATC

ATGGTGAAGTGATGACAAGCTACTCACATATGATGATTTTTTTTtCAAA

TTATGGCGAAAAAGTAAAGATTGAGAATCAGCGTATCTTAAATGATAAT

AAACTGCTATTTAGTAATAGAGTGAGTAGGGTGCGTTATCGGCCTTGTC

TTATTATTGATGCAAAAGATGCTTTATCAGTCTGTTCTGGCGTGTTTCA

TTAAGTAAAAAATGAATTCGGAGTTGTTGTTGCAAGCTCTCTTAATGTG

ATGATATACGATTATAAATCAATGTCAGATGAGGATATTATTCATATTT

TAAAGTCTGTCAAAAAACATCCAAAATTATCTTTAATAGAAAGCAAGAT

ACTTTTTTTAAAAGTGGTAATGAAAGGGATAAAATGTCGCCATATTGAG

TCGTTACTTAAGGTATCCGGAAGTACTGTGTATACGTATTGTATGAATA

TCAAGTCAAAAGCAAATATTTTtAGTTTTAAAGGGCAGTCCGTAATTCA

GGAATTAGAAAAAAGTCAATTTTTTAGTGATATTTCTATAAAGATAAAT

ATAGATTTCTATAACATTAATAATGGAGTAAATGAGAAAAATGTTTGCC

AAGTATATAGCCTAGCTTAA

Primers:

Forward FecR (Seq. ID No. 5):
TGGTGAAGTGATGACAAGCTAC

Reverse FecR (Seq. ID No. 6):
ACACAGTACTTCCGGATACCTT

PHARMAQ 001 ATP-grasp domain protein gene sequence (Seq. ID No. 7):

ATGATCAGCCTGTGGAAGACCTATCAGGCGCTTAAAACAAAGGGCATTT

TAGGCATTAATCAGCGTAATGCTGACTTTATTATTCGCTATAATCAGCG

CAAATACTACCCTTTAGTCGATGATAAAATCATGACAAAAACCCTTGCG

ATTAAAGATGGTATTGCCGTCCCTAAATTATATGCAACCCTTAAAACTG

ACCATGATACTCACCATCTGGAGCAAATTTTAGCCAATCGAACGGATTT

TGTCATTAAACCGGCCCGTGGTGCTGGCGGTGATGGTATTTTAGTCATT

ACCAACCGCCATGGTGAGCGTTTTCGCAAAGTCAGTGGTGCACTGTTAC

ACTTAGACGATATTCGTCATCACATTTCTAATATCTTAAGTGGGGTATA

CAGTCTTGGTGGCCAACGTGATCAGGCCATGATTGAATACCGCGTACAA

TTTGATCCATTATTTAAAAAAATCAGCTATCAAGGTGTGCCCGATATTC

GTATTATTGTCCTAAAAGGCTATCCTGCGATGGCGATGGTGCGTCTACC

CACTCGGCTCCCTGATGGCAAAGCCAACCTTCATCAAGGTGCAATTGGC

GTTGGCATTGACTTAACAACAGGCATCACCTTAGAAGGTGTTTGGATGA

ATGACCCAATTCATGAACATCCGGATACTGGCTATGCTGTACCAGGCTT

ACAGATTCCTCACTGGGATCAtTTTTTAAACCTTGCTGCACGCTGTTAC

GAGCTTACTCAACTAGGTTATTTAGGTGTGGATATTATCCTTGATAAAG

ACAAAGGCCCACTCATGCTTGAGCTTAATGCGCGTCCTGGTTTAAATAT

TCAAATTGCGAATAATAGCGGCTTATTGCATCGATTACGTTTCATTGAG

-continued

CAACAAAATCAACAACGCACAGCCGATGAACGCATTGCTTTCATCAAAC

ATCAGTTCGCAAAAATATAA

Primers:

Forward ATP-grasp domain protein (Seq. ID No. 8):
GGTGAGCGTTTTCGCAAAGT

Reverse ATP-grasp domain protein (Seq. ID No. 9):
TCAAGCATGAGTGGGCCTTT

PHARMAQ 001 FtsH gene sequence (Seq. ID No. 10):

ATGATTAAAAACATCATGCTATGGCTGGTCATTGCTTTGGTGTTGGTGA

CTGTGTTTAGTAATTTAGGCCCACGTCAGCAGTCGGTGAATCGGCTAGA

TTATTCAACATTTGTTAAAGACATCAATAATGGTCAAGTAAAAAGCGTT

ATCATTGATGGTTTGAATATTAAAGGACAAACCTCAAGTGGGACGCCAT

TTGCTACTTATATTCCGTGGAAAGATCCATTTTTAATGGATCAGATGCT

GGCGAAAAATGTCACAATTGCTGCTAAACCACCTGAGCAGCGGAGCTGG

TTATTGTCTGCATTAATCAGTTGGTTCCCTGGTATTTTATTAATTGCGA

TTTGGATTTTCTTCTTGCGGCAGATGCAAGGCGGTGGTGGTGGTAAGGG

CATGATGTCCTTTGGTTCCAGTAAGGCACGTCTGCTTGGTGAAGATCAA

ATTAAAGTTAACTTTGCTGATGTTGCTGGCTGTGAAGAGGCTAAAGAAG

AAGTAAAAGAACTGGTCGATTTTCTGCGTGACCCAACCAAATTCCAAAA

GTTAGGCGGCAAAATTCCGCAAGGGGTATTGATAGTTGGCCCACCTGGA

ACAGGTAAGACGCTATTAGCTAAAGCCATTGCAGGTGAGGCGAAAGTCC

CGTTCTTTTCTATTTCAGGCTCTGATTTTGTTGAAATGTTCGTCGGTGT

CGGTGCATCGCGGGTGCGTGATATGTTTGATCAGGCAAAAAAACGTGCA

CCGTGTATTATCTTTATCGATGAGATTGATGCAGTGGGCCGTCACCGTG

GCTCAGGTATGGGCGGTGGTCATGACGAACGTGAGCAGACCTTAAATCA

AATGCTGGTCGAGATGGATGGTTTTGAGGGAACCGAAGGGGTGATTGTC

ATTGCCGCGACGAATCGTCCGGATGTATTGGACCCGGCATTATTGCGTC

CCGGGCGTTTTGATCGCCAGGTCAGTGTCGGGCTTCCCGATGTCAAAGG

CCGTGAGCAGATTCTAAAAGTGCATATGCGTAAGGTGCCTTTGGGAGAT

GATGTTAAAGCGTCATTGATCGCCCGTGGTACGCCTGGGTTCTCAGGAG

CGGATTTGGCGAACTTGGTCAATGAAGCCGCACTCTTTGCCGCGCGTAA

AGATAAAACCGTGGTTGCTATGCGTGAGTTTGATGATGCCAAAGATAAA

ATTTTGATGGGCACTGAGCGCCGTTCGATGGCAATGACCGAAGAGCAAA

AACGTTTAACCGCCTTTCATGAGGCAGGGCACGCGATTGTCGGGTGTTT

GGTACCTGATCATGATCCGGTGTATAAAGTCTCGATTGTGCCGCGGGGT

CGTGCCTTAGGTGTGACCATGTATCTGCCTGAAGAGGATAGTTATGGTT

ATTCACGCGAGCGCTTGGAGAGCTTAATTTCGAGTATGTATGGCGGACG

TATTGCTGAAGCTTTAGTCTTTGGTGTTGAGAAAGTAACGACTGGGGCA

TCGAATGACATTGAAAAAGCCTCAGAAGTGGCGCGCAATATGGTGACAA

AGTGGGGGCTGTCTGAGCGCTTAGGGCCGATATTATATGGACAAGAAGG

-continued

```
CGGTGATCCGTTTGGTTATGGTGCGGGTAAAGGCACGCCGGAATTTTCA

GATCAAACCTCTGTTGCTATTGATGAGGAAGTACGTCAGATCATTGATC

GTAATTATACACGCGCTGAGAGCATTCTAATCAATAATCGGGATATTCT

TGATGCGATGGCGGATGCGTTGATGGTCTATGAGACGATTGATCGTGAC

CAAGTGGCTGATCTAATGGCGCGTCGGCCGGTGAAAGCACCGAAAGATT

GGGATCAGCCCTCTGATGAGAGTGGCTCATCAGCATCTGGTGATGAGTT

ACAACCTCTTGATGCTAATATCAATACTGATATTAATGAGACTAAGAGC

GCTGATCAAGAGACAGATCAGGGCGCGCCGTCACCAGAAATAAAGGGTA

AACCAGCGGATGATCCTACCTAA
```

Primers:

```
Forward FtsH (Seq. ID No. 11):
TGGTTCCAGTAAGGCACGTC

Reverse FtsH (Seq. ID No. 12):
ACAATCACCCCTTCGGTTCC
```

The mutations in the rpoD, FecR, ATP-grasp domain protein, and FtsH genes observed in PHARMAQ 001 have been found to be unique by comparison with DNA sequences from other strains of *P. salmonis*. For the purpose of the present disclosure, the mutations found in the *P. salmonis* strain PHARMAQ 001 are considered to represent single nucleotide polymorphisms and are located at positions corresponding to:

residue number 1417 of Seq. ID No. 1 (in the rpoD gene);

residue number 247 of Seq. ID No. 4 (in the FecR gene);

residue number 550 of Seq. ID No. 7 (in the ATP-grasp domain protein gene); and, residue number 573 of Seq. ID No. 10 (in the FtsH gene).

Table 1 shows the occurrence of the specific mutations in the rpoD, FecR, ATP-grasp domain protein, and FtsH genes observed in PHARMAQ 001 (described in Example 2) in 10 different wild-type virulent strains of *P. salmonis*.

TABLE 1

| | | | Gene | | | |
|---|---|---|---|---|---|---|
| Strain | Origin | Group | rpoD | FecR | ATP-gbp | FtsH |
| PHARMAQ 001 | Atlantic salmon, Chile | EM-90 like | X | X | X | X |
| AL 10 005 | Atlantic salmon, Chile | EM-90 like | n | n | n | n |
| AL 20 218 | Atlantic salmon, Chile | EM-90 like | n | n | n | n |
| AL 20 223 | Atlantic salmon, Chile | LF-89 like | n | n | n | n |
| AL 20 220 | Trout, Chile | LF-89 like | n | n | n | n |
| AL 20 471 | Trout, Chile | LF-89 like | n | n | n | n |
| AL 20 222 | Trout, Chile | LF-89 like | n | n | n | n |
| A1-15972 | Atlantic salmon, Chile | EM-90 like | n | n | n | n |
| B1-32597 | Coho salmon, Chile | LF-89 like | n | n | n | n |
| LF-89 | Coho salmon, Chile | LF-89 | n | n | n | n |
| EM-90 | Atlantic salmon, Chile | EM-90 | n | n | n | n |

In Table 1, "X" indicates that the specific mutation found in PHARMAQ 001 (described in Example 2) in each of the rpoD, ATP-grasp domain protein, FtsH, or FecR genes is present, and "n" indicates that the mutation is not present. As shown in Table 1, none of the strains of *P. salmonis* that were examined were found to possess any of the mutations described in Example 2 in the rpoD, FecR, ATP-grasp domain protein, and FtsH genes.

Thus, only PHARMAQ 001, and no other strains of *P. salmonis*, possesses the described mutations in the rpoD, FecR, ATP-grasp domain protein, and FtsH genes.

The presence of these mutations in the rpoD, FecR, ATP-grasp domain protein, and FtsH genes therefore provides a means of differentiating and distinguishing the PHARMAQ 001 strain from other *Piscirickettsia salmonis* strains.

A method of identifying the PHARMAQ 001 strain involves analysing the DNA sequence of the specific portions of each of the rpoD, FecR, ATP-grasp domain protein, and FtsH genes containing the identified mutation. The specific portions of the genes may be amplified by polymerase chain reaction (PCR) using specific DNA primers (shown above) followed by DNA sequencing using standard methods. When compared to the sequences of LF-89 (and other wild type strains) the sequences of each of the specific amplified portions of the rpoD, FecR, ATP-grasp domain protein, and FtsH genes harbors a DNA point mutation which is specific and unique for PHARMAQ 001.

Mutations in the rpoD, FecR, ATP-grasp domain protein, and FtsH genes were identified due to the fact that they are the four mutations in PHARMAQ 001 which result in a significant change in the amino acid sequence of a protein.

Amino acid sequence alignments between a number of virulent wild-type strains of *P. salmonis* and the PHARMAQ 001 attenuated strain for each of the rpoD, FecR, ATP-grasp domain protein, and FtsH gene products were investigated and are shown below.

The amino acid sequences of *P. salmonis* strains LF-89, EM-90, A1-15972, and B1-32597 were obtained from the published genome sequences of these strains (LF-89, DDBJ/EMBL/GenBank accession no. AMFF00000000.2; EM-90, GenBank accession no.: JRHP00000000.1; A1-15972, GenBank accession no.: JRAV00000000.2; and B1-32597, GenBank accession no.: JRAD00000000.2). The amino acid sequences for the other strains listed below were obtained from the relevant virulent wild-type strain by means of standard PCR and sequencing methods using the PCR primer pairs described above (Seq. ID No.s 2 and 3, 5 and 6, 8 and 9, 11 and 12).

```
PHARMAQ_001 MDQQEKRSQF KELIVRGKQQ GFLTFTEVND HLPDDMSSPE EVEEIVAMIS DMGIPVYETA
A1-15972    MDQQEKRSQF KELIVRGKQQ GFLTFTEVND HLPDDMSSPE EVEEIVAMIS DMGIPVYETA
B1-32597    MDQQEKKSQF KELIVRGKQQ GFLTFTEVND HLPDDMSSPE EVEEIVAMIS DMGIPVYETA
EM-90       MDQQEKRSQF KELIVRGKQQ GFLTFTEVND HLPDDMSSPE EVEEIVAMIS DMGIPVYETA
LF-89       MDQQEKRSQF KELIVRGKQQ GFLTFTEVND HLPDDMSSPE EVEEIVAMIS DMGIPVYETA
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
AL20223     ---------- ---------- ---------- ---------- ---------- ----------
AL20277     ---------- ---------- ---------- ---------- ---------- ----------

61
PHARMAQ_001 PDPDSLLMNE HASSAEDDAD DAVAALDSDA EFGRTTDPVR MYMREMGSVE LLTRQGEIEL
A1-15972    PDPDSLLMNE HASSAEDDAD DAVAALDSDA EFGRTTDPVR MYMREMGSVE LLTRQGEIEL
B1-32597    PDPDSLLMNE HASSAEDDAD DAVAALGSDA EFGRTTDPVR MYMREMGSVE LLTRQGEIEL
EM-90       PDPDSLLMNE HASSAEDDAD DAVAALDSDA EFGRTTDPVR MYMREMGSVE LLTRQGEIEL
LF-89       PDPDSLLMNE HASSAEDDAD DAVAALDSDA EFGRTTDPVR MYMREMGSVE LLTRQGEIEL
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
AL20223     ---------- ---------- ---------- ---------- ---------- ----------
AL20277     ---------- ---------- ---------- ---------- ---------- ----------

121
PHARMAQ_001 AKRIEEGVKQ AFEAIAHYPQ STAIILEEYA RFEAEEIRLD DIISGYITEE DEAPTSNIGS
A1-15972    AKRIEEGVKQ AFEAIAHYPQ STAIILEEYA RFEAEEIRLD DIISGYITEE DEAPTSNIGS
B1-32597    AKRIEEGVKQ AFEAIAHYPQ STAIILEEYA RFEAEEIRLD DIISGYITEE DEAPTSNIGS
EM-90       AKRIEEGVKQ AFEAIAHYPQ STAIILEEYA RFEAEEIRLD DIISGYITEE DEAPTSNIGS
LF-89       AKRIEEGVKQ AFEAIAHYPQ STAIILEEYA RFEAEEIRLD DIISGYITEE DEAPTSNIGS
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
AL20223     ---------- ---------- ---------- ---------- ---------- ----------
AL20277     ---------- ---------- ---------- ---------- ---------- ----------

181
PHARMAQ_001 MLDDANKADD NFEAALTEDD STDDGEGEDD NEEIPVDNTL DVEEAAERFA ELKAAYDAVI
A1-15972    MLDDANKADD NFEAALTEDD STDDGEGEDD NEEIPVDNTL DVEEAAERFA ELKAAYDAVI
B1-32597    MLHDANKADD NFEAALTEDD STDDAEDEGD NEEIPVDNTL DVEEAAERFA ELKAAYDAVI
EM-90       MLDDANKADD NFEAALTEDD STDDGEGEDD NEEIPVDNTL DVEEAAERFA ELKAAYDAVI
LF-89       MLDDANKADD NFEAALTEDD STDDGEGEDD NEEIPVDNTL DVEEAAERFA ELKAAYDAVI
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
AL20223     ---------- ---------- ---------- ---------- ---------- ----------
AL20277     ---------- ---------- ---------- ---------- ---------- ----------

241
PHARMAQ_001 QVQEKHGIHH KKTQQRCEEL SKVLMTFRLK PNMIDKITNY LHGLLSQVRK HERHIMALCI
A1-15972    QVQEKHGIHH KKTQQRCEEL SKVLMTFRLK PNMIDKITNY LHGLLSQVRK HERHIMALCI
B1-32597    QVQEKHGIHH KKTQQRCEEL SKVLMTFRLK PNMIDKITNY LHDLLSQVRK HERHIMALCI
EM-90       QVQEKHGIHH KKTQQRCEEL SKVLMTFRLK PNMIDKITNY LHGLLSQVRK HERHIMALCI
LF-89       QVQEKHGIHH KKTQQRCEEL SKVLMTFRLK PNMIDKITNY LHGLLSQVRK HERHIMALCI
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
AL20223     ---------- ---------- ---------- ---------- ---------- ----------
AL20277     ---------- ---------- ---------- ---------- ---------- ----------

301
PHARMAQ_001 NQAKMPRKLF IDIFPGNETN LEWIEYQIKA EQSYSEALQS LAPEVTRAQK KLISLEQESN
A1-15972    NQAKMPRKLF IDIFPGNETN LEWIEYQIKA EQSYSEALQS LAPEVTRAQK KLISLEQESN
B1-32597    NQAKMPRKLF IDIFPGNETN LDWIEYQIKA EQSYSEALQS LAPEVTRAQK KLISLEQESN
EM-90       NQAKMPRKLF IDIFPGNETN LEWIEYQIKA EQSYSEALQS LAPEVTRAQK KLISLEQESN
LF-89       NQAKMPRKLF IDIFPGNETN LEWIEYQIKA EQSYSEALQS LAPEVTRAQK KLISLEQESN
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
```

-continued

```
AL20223     ---------- ---------- ---------- ---------- ---------- ----------
AL20277     ---------- ---------- ---------- ---------- ---------- ----------

361
PHARMAQ_001 FDVTAIKEVN RNISIGEAKA HRAKKEMVEA NLRLVISIAK KYTNRGLQFL DLIQEGNIGL
A1-15972    FDVTAIKEVN RNISIGEAKA HRAKKEMVEA NLRLVISIAK KYTNRGLQFL DLIQEGNIGL
B1-32597    FDVTAIKEVN RNISIGEAKA HRAKKEMVEA NLRLVISIAK KYTNRGLQFL DLIQEGNIGL
EM-90       FDVTAIKEVN RNISIGEAKA HRAKKEMVEA NLRLVISIAK KYTNRGLQFL DLIQEGNIGL
LF-89       FDVTAIKEVN RNISIGEAKA HRAKKEMVEA NLRLVISIAK KYTNRGLQFL DLIQEGNIGL
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
AL20223     ---------- ---------- ---------- ---------- ---------- ----------
AL20277     ---------- ---------- ---------- ---------- ---------- ----------

421                                                                  *
PHARMAQ_001 MKAVDKFEYR RGYKFSTYAT WWIRQAITRS IADQARTIRI PVHMIETINK LNCVSRQMIQ
A1-15972    MKAVDKFEYR RGYKFSTYAT WWIRQAITRS IADQARTIRI PVHMIETINK LNRVSRQMIQ
B1-32597    MKAVDKFEYR RGYKFSTYAT WWIRQAITRS IADQARTIRI PVHMIETINK LNRVSRQMIQ
EM-90       MKAVDKFEYR RGYKFSTYAT WWIRQAITRS IADQARTIRI PVHMIETINK LNRVSRQMIQ
LF-89       MKAVDKFEYR RGYKFSTYAT WWIRQAITRS IADQARTIRI PVHMIETINK LNRVSRQMIQ
AL10016     ---------- ---------- ---------- ---------- -VHMIETINK LNRVSRQMIQ
AL10008     ---------- ---------- ---------- ---------- -VHMIETINK LNRVSRQMIQ
AL20218     ---------- ---------- ---------- ---------- -VHMIETINK LNRVSRQMIQ
AL20219     ---------- ---------- ---------- ---------- -VHMIETINK LNRVSRQMIQ
AL20222     ---------- ---------- ---------- ---------- -VHMIETINK LNRVSRQMIQ
AL20223     ---------- ---------- ---------- ---------- -VHMIETINK LNRVSRQMIQ
AL20277     ---------- ---------- ---------- ---------- -VHMIETINK LNRVSRQMIQ

481
PHARMAQ_001 ELGREATPEE LSERMEMPEH KIRKILKIAK EPISMETPIG DDEDSHLGDF IEDTTMQLPV
A1-15972    ELGREATPEE LSERMEMPEH KIRKILKIAK EPISMETPIG DDEDSHLGDF IEDTTMQLPV
B1-32597    ELGREATPEE LSERMEMPEH KIRKILKIAK EPISMETPIG DDEDSHLGDF IEDTTMQLPV
EM-90       ELGREATPEE LSERMEMPEH KIRKILKIAK EPISMETPIG DDEDSHLGDF IEDTTMQLPV
LF-89       ELGREATPEE LSERMEMPEH KIRKILKIAK EPISMETPIG DDEDSHLGDF IEDTTMQLPV
AL10016     ELGREATPEE LSERMEMPEH KIRK------ ---------- ---------- ----------
AL10008     ELGREATPEE LSERMEMPEH KIRK------ ---------- ---------- ----------
AL20218     ELGREATPEE LSERMEMPEH KIRK------ ---------- ---------- ----------
AL20219     ELGREATPEE LSERMEMPEH KIRK------ ---------- ---------- ----------
AL20222     ELGREATPEE LSERMEMPEH KIRK------ ---------- ---------- ----------
AL20223     ELGREATPEE LSERMEMPEH KIRK------ ---------- ---------- ----------
AL20277     ELGREATPEE LSERMEMPEH KIRK------ ---------- ---------- ----------

541
PHARMAQ_001 DSTMGDALKQ ATSDILENLT PREAEVLRMR FGIDMNTDHT LEEVGKQFDV TRERIRQIEA
A1-15972    DSTMGDALKQ ATSDILENLT PREAKVLRMR FGIDMNTDHT LEEVGKQFDV TRERIRQIEA
B1-32597    DSTMGDALKQ ATSDILENLT PREAKVLRMR FGIDMNTDHT LEEVGKQFDV TRERIRQIEA
EM-90       DSTMGDALKQ ATSDILENLT PREAKVLRMR FGIDMNTDHT LEEVGKQFDV TRERIRQIEA
LF-89       DSTMGDALKQ ATSDILENLT PREAKVLRMR FGIDMNTDHT LEEVGKQFDV TRERIRQIEA
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20222     ---------- ---------- ---------- ---------- ---------- ----------
AL20223     ---------- ---------- ---------- ---------- ---------- ----------
AL20277     ---------- ---------- ---------- ---------- ---------- ----------

601
PHARMAQ_001 KALRKLRHPT RSEILKSFLD SEE* (Seq. ID No. 13)
A1-15972    KALRKLRHPT RSEILKSFLD SEE* (Seq. ID No. 14)
B1-32597    KALRKLRHPT RSEILKSFLD SEE* (Seq. ID No. 15)
EM-90       KALRKLRHPT RSEILKSFLD SEE* (Seq. ID No. 16)
LF-89       KALRKLRHPT RSEILKSFLD SEE* (Seq. ID No. 17)
AL10016     ---------- ---------- ---- (Seq. ID No. 18)
AL10008     ---------- ---------- ---- (Seq. ID No. 19)
AL20218     ---------- ---------- ---- (Seq. ID No. 20)
AL20219     ---------- ---------- ---- (Seq. ID No. 21)
AL20222     ---------- ---------- ---- (Seq. ID No. 22)
AL20223     ---------- ---------- ---- (Seq. ID No. 23)
AL20277     ---------- ---------- ---- (Seq. ID No. 24)
```

The rpoD amino acid sequence alignment reveals that there are natural polymorphisms of the rpoD gene product between wild-type strains. However, all of the wild-type strains are virulent and therefore none of the differences between the wild-type sequences can be considered to affect virulence. PHARMAQ 001 has an arginine to cysteine mutation at position 473 of the amino acid sequence of the rpoD gene product and this mutation is not seen in any of the wild-type strains investigated, such as A1-15972, B1-32597, EM-90, and/or LF-89. The protein sequence of the rpoD gene product in PHARMAQ 001 is otherwise identical to that of wild-type strains including A1-15972, EM-90, and LF-89. The sequences of 11 wild-type strains were examined in the region of amino acid residues 462-504 of the rpoD gene product. All of the sequences were found to be identical in this region, but different to that of PHARMAQ 001.

FecR Amino Acid Sequence Alignment:

```
PHARMAQ_001 MKINHQPGGI MLIMNNHGEV MTSYSHMMIF FSNYGEKVKI ENQRILNDNK LLFSNRVSRV
LF-89       MKINHQPGGI MLIMNNHGEV MTSYSHMMSF FSNYGEKVKI ENQRILNDNK LLFSNRVSRV
EM-90       MKINHQPGGI MLIMNNHGEV MTSYSHMMSF FSNYGEKVKI ENQRILNDNK LLFSNRVSRV
B1-32597    MKINHQPGGI MLIMNNHGEV MTSYSHMMSF FSNYGEKVKI ENQRILNDNK LLFSNRVSEV
A1-15972    MKINHQPGGI MLIMNNHGEV MTSYSHMMIF FSNYGEKVKI ENQRILNDNK LLFSNRVSRV
AL10016     ---------- ---------- ---------- -------?KI ENQRILNDNK LLFSNRVSRV
AL10008     ---------- ---------- ---------- -------?KI ENQRILNDNK LLFSNRVSRV
AL20218     ---------- ---------- ---------- -------?KI ENQRILNDNK LLFSNRVSRV
AL20219     ---------- ---------- ---------- -------?KI ENQRILNDNK LLFSNRVSRV
AL20220     ---------- ---------- ---------- -------?KI ENQRILNDNK LLFSNRVSEV
AL20223     ---------- ---------- ---------- -------?KI ENQRILNDNK LLFSNRVSEV
AL20470     ---------- ---------- ---------- -------?KI ENQRILNDNK LLFSNRVSEV
AL20471     ---------- ---------- ---------- -------?KI ENQRILNDNK LLFSNRVSEV
AL20455     ---------- ---------- ---------- -------?KI ENQRILNDNK LLFSNRVSEV

61
PHARMAQ_001 RYRPCLIIDA KDALSVCSGV FH*------- ---------- ---------- ----------
LF-89       RYRPCLIIDA KDALSVCSGV FHQVKNEFGV VVASSLNVMI YDYKSMSDED IIHILKSVKK
EM-90       RYRPCLIIDA KDALSVCSGV FHQVKNEFGV VVASSLNVMI YDYKSMSDED IIHILKSVKK
B1-32597    RYRPCLIIDA KDAFSVCSGV FHQVKNEFGV VVANSLNVMI YDYKSMSDED IIHILKSVKK
A1-15972    RYRPCLIIDA KDALSVCSGV FHQVKNEFGV VVASSLNVMI YDYKSMSDED IIHILKSVKK
AL10016     RYRPCLIIDA KDALSVCSGV FHQVKNEFGV VVASSLNVMI YDYKSMSDED IIHILKSVKK
AL10008     RYRPCLIIDA KDALSVCSGV FHQVKNEFGV VVASSLNVMI YDYKSMSDED IIHILKSVKK
AL20218     RYRPCLIIDA KDALSVCSGV FHQVKNEFGV VVASSLNVMI YDYKSMSDED IIHILKSVKK
AL20219     RYRPCLIIDA KDALSVCSGV FHQVKNEFGV VVASSLNVMI YDYKSMSDED IIHILKSVKK
AL20220     RYRPCLIIDA KDAFSVCSGV FHQVKNEFGV VVANSLNVMI YDYKSMSDED IIHILKSVKK
AL20223     RYRPCLIIDA KDAFSVCSGV FHQVKNEFGV VVANSLNVMI YDYKSMSDED IIHILKSVKK
AL20470     RYRPCLIIDA KDAFSVCSGV FHQVKNEFGV VVANSLNVMI YDYKSMSDED IIHILKSVKK
AL20471     RYRPCLIIDA KDAFSVCSGV FHQVKNEFGV VVANSLNVMI YDYKSMSDED IIHILKSVKK
AL20455     RYRPCLIIDA KDAFSVCSGV FHQVKNEFGV VVANSLNVMI YDYKSMSDED IIHILKSVKK

121
PHARMAQ_001 ---------- ---------- ---------- ---------- ---------- ----------
LF-89       HPKLSLIESK ILFLKVVMKG IKCRHIESLL KVSGSTVYTY CMNIKSKANI FSFKGQSVIQ
EM-90       HPKLSLIESK ILFLKVVMKG IKCRHIESLL KVSGSTVYTY CMNIKSKANI FSFKGQSVIQ
B1-32597    HPKLSLIESK ILFLKVVMKG IKCRHIESLL KVSGSTVYTY CMNIKSKANI FSFKGQSVIQ
A1-15972    HPKLSLIESK ILFLKVVMKG IKCRHIESLL KVSGSTVYTY CMNIKSKANI FSFKGQSVIQ
AL10016     HPKLSLIESK ILFLKVV?-- ---------- ---------- ---------- ----------
AL10008     HPKLSLIESK ILFLKVV?-- ---------- ---------- ---------- ----------
AL20218     HPKLSLIESK ILFLKVV?-- ---------- ---------- ---------- ----------
AL20219     HPKLSLIESK ILFLKVV?-- ---------- ---------- ---------- ----------
AL20220     HPKLSLIESK ILFLKVV?-- ---------- ---------- ---------- ----------
AL20223     HPKLSLIESK ILFLKVV?-- ---------- ---------- ---------- ----------
AL20470     HPKLSLIESK ILFLKVV?-- ---------- ---------- ---------- ----------
AL20471     HPKLSLIESK ILFLKVV?-- ---------- ---------- ---------- ----------
AL20455     HPKLSLIESK ILFLKVV?-- ---------- ---------- ---------- ----------

181
PHARMAQ_001 ---------- ---------- ---------- --------- (Seq. ID No. 25)
LF-89       ELEKSQFFSD ISIKINIDFY NINNGVNEKN VCQVYSLA* (Seq. ID No. 26)
EM-90       ELEKSQFFSD ISIKINIDFY NINNGVNEKN VCQVYSLA* (Seq. ID No. 27)
B1-32597    ELEKSQFFSD IAMKINIDFY SINNEANEKN VCQVYSLA* (Seq. ID No. 28)
A1-15972    ELEKSQFFSD ISIKINIDFY NINNGVNEKN VCQVYSLA* (Seq. ID No. 29)
AL10016     ---------- ---------- ---------- --------- (Seq. ID No. 30)
AL10008     ---------- ---------- ---------- --------- (Seq. ID No. 31)
AL20218     ---------- ---------- ---------- --------- (Seq. ID No. 32)
AL20219     ---------- ---------- ---------- --------- (Seq. ID No. 33)
AL20220     ---------- ---------- ---------- --------- (Seq. ID No. 34)
AL20223     ---------- ---------- ---------- --------- (Seq. ID No. 35)
AL20470     ---------- ---------- ---------- --------- (Seq. ID No. 36)
AL20471     ---------- ---------- ---------- --------- (Seq. ID No. 37)
AL20455     ---------- ---------- ---------- --------- (Seq. ID No. 38)
```

introduced at position 83 of the amino acid, and this mutation is not seen in any of the wild-type strains investigated, such as A1-15972, B1-32597, EM-90, and/or LF-89. The protein sequence of the FecR gene product in PHARMAQ 001 is otherwise identical to that of wild-type strains including A1-15972, EM-90, and LF-89. The sequences of 13 wild-type strains were examined in the region of amino acid residues 39-137 of the FecR gene product. None of the wild-type sequences were found to be prematurely truncated, whereas in contrast, the FecR gene product of PHARMAQ 001 is terminated by a stop codon in position 83.

The FecR amino acid sequence alignment reveals that there are natural polymorphisms of the FecR gene product between wild-type strains. However, all of the wild-type strains are virulent and therefore none of the differences between the wild-type sequences can be considered to affect virulence. PHARMAQ 001 has a premature stop codon ATP-Grasp Domain Protein Amino Acid Sequence Alignment:

```
PHARMAQ001MISLWKTYQA LKTKGILGIN QRNADFIIRY NQRKYYPLVD DKIMTKTLAI KDGIAVPKLY
LF-89     MISLWKTYQA LKTKGILGIN QRNADFIIRY NQRKYYPLVD DKIMTKTLAI KDGIAVPKLY
EM-90     MISLWKTYQA LKTKGILGIN QRNADFIIRY NQRKYYPLVD DKIMTKTLAI KDGIAVPKLY
B1-32597  MISLWKTYQA LKTKGILGIN QRNADFIIRY NQRKYYPLVD DKIMTKTLAI KDGIAVPKLY
A1-15972  MISLWKTYQA LKTKGILGIN QRNADFIIRY NQRKYYPLVD DKIMTKTLAI KDGIAVPKLY
AL10016   ---------- ---------- ---------- ---------- ---------- ----------
AL10008   ---------- ---------- ---------- ---------- ---------- ----------
AL20218   ---------- ---------- ---------- ---------- ---------- ----------
AL20219   ---------- ---------- ---------- ---------- ---------- ----------
AL20220   ---------- ---------- ---------- ---------- ---------- ----------
AL20223   ---------- ---------- ---------- ---------- ---------- ----------
AL20470   ---------- ---------- ---------- ---------- ---------- ----------
AL20471   ---------- ---------- ---------- ---------- ---------- ----------
AL20455   ---------- ---------- ---------- ---------- ---------- ----------

61
PHARMAQ001ATLKTDHDTH HLEQILANRT DFVIKPARGA GGDGILVITN RHGERFRKVS GALLHLDDIR
LF-89     ATLKTDHDTH HLEQILANRT DFVIKPARGA GGDGILVITN RHGERFRKVS GALLHLDDIR
EM-90     ATLKTDHDTH HLEQILANRT DFVIKPARGA GGDGILVITN RHGERFRKVS GALLHLDDIR
B1-32597  ATLKTDHDTH HLEQILANRT DFVIKPARGA GGDGILVITN RHGERFRKVS GALLHLDDIR
A1-15972  ATLKTDHDTH HLEQILANRT DFVIKPARGA GGDGILVITN RHGERFRKVS GALLHLDDIR
AL10016   ---------- ---------- ---------- ---------- ---------- ------?DIR
AL10008   ---------- ---------- ---------- ---------- ---------- ------?DIR
AL20218   ---------- ---------- ---------- ---------- ---------- ------?DIR
AL20219   ---------- ---------- ---------- ---------- ---------- ------?DIR
AL20220   ---------- ---------- ---------- ---------- ---------- ------?DIR
AL20223   ---------- ---------- ---------- ---------- ---------- ------?DIR
AL20470   ---------- ---------- ---------- ---------- ---------- ------?DIR
AL20471   ---------- ---------- ---------- ---------- ---------- ------?DIR
AL20455   ---------- ---------- ---------- ---------- ---------- ------?DIR

121
PHARMAQ001HHISNILSGV YSLGGQRDQA MIEYRVQFDP LFKKISYQGV PDIRIIVLKG YPAMAMVRLP
LF-89     HHISNILSGV YSLGGQRDQA MIEYRVQFDP LFKKISYQGV PDIRIIVLKG YPAMAMVRLP
EM-90     HHISNILSGV YSLGGQRDQA MIEYRVQFDP LFKKISYQGV PDIRIIVLKG YPAMAMVRLP
B1-32597  HHISNILSGV YSLGGQRDQA MIEYRVQFDP LFKKISYQGV PDIRIIVLKG YPAMAMVRLP
A1-15972  HHISNILSGV YSLGGQRDQA MIEYRVQFDP LFKKISYQGV PDIRIIVLKG YPAMAMVRLP
AL10016   HHISNILSGV YSLGGQRDQA MIEYRVQFDP LFKKISYQGV PDIRIIVLKG YPAMAMVRLP
AL10008   HHISNILSGV YSLGGQRDQA MIEYRVQFDP LFKKISYQGV PDIRIIVLKG YPAMAMVRLP
AL20218   HHISNILSGV YSLGGQRDQA MIEYRVQFDP LFKKISYQGV PDIRIIVLKG YPAMAMVRLP
AL20219   HHISNILSGV YSLGGQRDQA MIEYRVQFDP LFKKISYQGV PDIRIIVLKG YPAMAMVRLP
AL20220   HHISNILSGV YSLGGQRDQA MIEYRVQFDP LFKKISYQGV PDIRIIVLKG YPAMAMVRLP
AL20223   HHISNILSGV YSLGGQRDQA MIEYRVQFDP LFKKISYQGV PDIRIIVLKG YPAMAMVRLP
AL20470   HHISNILSGV YSLGGQRDQA MIEYRVQFDP LFKKISYQGV PDIRIIVLKG YPAMAMVRLP
AL20471   HHISNILSGV YSLGGQRDQA MIEYRVQFDP LFKKISYQGV PDIRIIVLKG YPAMAMVRLP
AL20455   HHISNILSGV YSLGGQRDQA MIEYRVQFDP LFKKISYQGV PDIRIIVLKG YPAMAMVRLP

181          *
PHARMAQ001TRLPDGKANL HQGAIGVGID LTTGITLEGV WMNDPIHEHP DTGYAVPGLQ IPHWDHFLNL
LF-89     TRLSDGKANL HQGAIGVGID LTTGITLEGV WMNDPIHEHP DTGYAVPGLQ IPHWDHFLNL
EM-90     TRLSDGKANL HQGAIGVGID LTTGITLEGV WMNDPIHEHP DTGYAVPGLQ IPHWDHFLNL
B1-32597  TRLSDGKANL HQGAIGVGID LTTGITLEGV WMNDPIHEHP DTGYAVPGLQ IPHWDHFLNL
A1-15972  TRLSDGKANL HQGAIGVGID LTTGITLEGV WMNDPIHEHP DTGYAVPGLQ IPHWDHFLNL
AL10016   TRLSDGKANL HQGAIGVGID LTTGITLEGV WMNDPIHEHP DTGYAVPGLQ IPHWDHFLNL
AL10008   TRLSDGKANL HQGAIGVGID LTTGITLEGV WMNDPIHEHP DTGYAVPGLQ IPHWDHFLNL
AL20218   TRLSDGKANL HQGAIGVGID LTTGITLEGV WMNDPIHEHP DTGYAVPGLQ IPHWDHFLNL
AL20219   TRLSDGKANL HQGAIGVGID LTTGITLEGV WMNDPIHEHP DTGYAVPGLQ IPHWDHFLNL
AL20220   TRLSDGKANL HQGAIGVGID LTTGITLEGV WMNDPIHEHP DTGYAVPGLQ IPHWDHFLNL
AL20223   TRLSDGKANL HQGAIGVGID LTTGITLEGV WMNDPIHEHP DTGYAVPGLQ IPHWDHFLNL
AL20470   TRLSDGKANL HQGAIGVGID LTTGITLEGV WMNDPIHEHP DTGYAVPGLQ IPHWDHFLNL
AL20471   TRLSDGKANL HQGAIGVGID LTTGITLEGV WMNDPIHEHP DTGYAVPGLQ IPHWDHFLNL
AL20455   TRLSDGKANL HQGAIGVGID LTTGITLEGV WMNDPIHEHP DTGYAVPGLQ IPHWDHFLNL

241
PHARMAQ001AARCYELTQL GYLGVDIILD KDKGPLMLEL NARPGLNIQI ANNSGLLHRL RFIEQQNQQR
LF-89     AARCYELTQL GYLGVDIILD KDKGPLMLEL NARPGLNIQI ANNSGLLHRL RFIEQQNQQR
EM-90     AARCYELTQL GYLGVDIILD KDKGPLMLEL NARPGLNIQI ANNSGLLHRL RFIEQQNQQR
B1-32597  AARCYELTQL GYLGVDIILD KDKGPLMLEL NARPGLNIQI ANNSGLLHRL RFIEQQNQQR
A1-15972  AARCYELTQL GYLGVDIILD KDKGPLMLEL NARPGLNIQI ANNSGLLHRL RFIEQQNQQR
AL10016   AARCYELTQL G?-------- ---------- ---------- ---------- ----------
AL10008   AARCYELTQL G?-------- ---------- ---------- ---------- ----------
AL20218   AARCYELTQL G?-------- ---------- ---------- ---------- ----------
AL20219   AARCYELTQL G?-------- ---------- ---------- ---------- ----------
AL20220   AARCYELTQL G?-------- ---------- ---------- ---------- ----------
AL20223   AARCYELTQL G?-------- ---------- ---------- ---------- ----------
AL20470   AARCYELTQL G?-------- ---------- ---------- ---------- ----------
```

-continued

```
AL20471   AARCYELTQL G?-------- ---------- ---------- ---------- ----------
AL20455   AARCYELTQL G?-------- ---------- ---------- ---------- ----------

301
PHARMAQ001TADERIAFIK HQFAKI* (Seq. ID No. 39)
LF-89     TADERIAFIK HQFAKI* (Seq. ID No. 40)
EM-90     TADERIAFIK HQFAKI* (Seq. ID No. 41)
B1-32597  TADERIAFIK HQFAKI* (Seq. ID No. 42)
A1-15972  TADERIAFIK HQFAKI* (Seq. ID No. 43)
AL10016   ---------- ------- (Seq. ID No. 44)
AL10008   ---------- ------- (Seq. ID No. 45)
AL20218   ---------- ------- (Seq. ID No. 46)
AL20219   ---------- ------- (Seq. ID No. 47)
AL20220   ---------- ------- (Seq. ID No. 48)
AL20223   ---------- ------- (Seq. ID No. 49)
AL20470   ---------- ------- (Seq. ID No. 50)
AL20471   ---------- ------- (Seq. ID No. 51)
AL20455   ---------- ------- (Seq. ID No. 52)
```

All of the wild-type sequences of the ATP-grasp domain protein gene product that were investigated were found to be identical. However, PHARMAQ 001 has a serine to proline mutation at position 184 of the amino acid sequence of the ATP-grasp domain protein gene product which is not seen in the wild-type sequence. The sequences of 13 wild-type strains were examined in the region of amino acid residues 118-251 of the ATP-grasp domain protein gene product. All of the sequences were found to be identical in this region, but different to that of PHARMAQ 001.

FtsH Amino Acid Sequence Alignment:

```
PHARMAQ001  MIKNIMLWLV IALVLVTVFS NLGPRQQSVN RLDYSTFVKD INNGQVKSVI IDGLNIKGQT
LF-89       MIKNIMLWLV IALVLVTVFS NLGPRQQSVN RLDYSTFVKD INNGQVKSVI IDGLNIKGQT
EM-90       MIKNIMLWLV IALVLVTVFS NLGPRQQSVN RLDYSTFVKD INNGQVKSVI IDGLNIKGQT
B1_32597    MIKNIMLWLV IALVLVTVFS NLGPRQQSVN RLDYSTFVKD INNGQVKSVI IDGLNIKGQT
A1_15972    MIKNIMLWLV IALVLVTVFS NLGPRQQSVN RLDYSTFVKD INNGQVKSVI IDGLNIKGQT
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
AL20471     ---------- ---------- ---------- ---------- ---------- ----------
AL20455     ---------- ---------- ---------- ---------- ---------- ----------

61
PHARMAQ001  SSGTPFATYI PWKDPFLMDQ MLAKNVTIAA KPPEQRSWLL SALISWFPGI LLIAIWIFFL
LF-89       SSGTPFATYI PWKDPFLMDQ MLAKNVTIAA KPPEQRSWLL SALISWFPGI LLIAIWIFFL
EM-90       SSGTPFATYI PWKDPFLMDQ MLAKNVTIAA KPPEQRSWLL SALISWFPGI LLIAIWIFFL
B1_32597    SSGTPFATYI PWKDPFLMDQ MLSKNVTIAA KPPEQRSWLL SALISWFPGI LLIAIWIFFL
A1_15972    SSGTPFATYI PWKDPFLMDQ MLAKNVTIAA KPPEQRSWLL SALISWFPGI LLIAIWIFFL
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
AL20471     ---------- ---------- ---------- ---------- ---------- ----------
AL20455     ---------- ---------- ---------- ---------- ---------- ----------

121
PHARMAQ001  RQMQGGGGGK GMMSFGSSKA RLLGEDQIKV NFADVAGCEE AKEEVKELVD FLRDPTKFQK
LF-89       RQMQGGGGGK GMMSFGSSKA RLLGEDQIKV NFADVAGCEE AKEEVKELVD FLRDPTKFQK
EM-90       RQMQGGGGGK GMMSFGSSKA RLLGEDQIKV NFADVAGCEE AKEEVKELVD FLRDPTKFQK
B1_32597    RQMQGGGGGK GMMSFGSSKA RLLGEDQIKV NFADVAGCEE AKEEVKELVD FLRDPTKFQK
A1_15972    RQMQGGGGGK GMMSFGSSKA RLLGEDQIKV NFADVAGCEE AKEEVKELVD FLRDPTKFQK
AL10016     ---------- ---------- ---------- -FADVAGCEE AKEEVKELVD FLRDPTKFQK
AL10008     ---------- ---------- ---------- -FADVAGCEE AKEEVKELVD FLRDPTKFQK
AL20218     ---------- ---------- ---------- -FADVAGCEE AKEEVKELVD FLRDPTKFQK
AL20219     ---------- ---------- ---------- -FADVAGCEE AKEEVKELVD FLRDPTKFQK
AL20220     ---------- ---------- ---------- -FADVAGCEE AKEEVKELVD FLRDPTKFQK
AL20223     ---------- ---------- ---------- -FADVAGCEE AKEEVKELVD FLRDPTKFQK
AL20470     ---------- ---------- ---------- -FADVAGCEE AKEEVKELVD FLRDPTKFQK
AL20471     ---------- ---------- ---------- -FADVAGCEE AKEEVKELVD FLRDPTKFQK
AL20455     ---------- ---------- ---------- -FADVAGCEE AKEEVKELVD FLRDPTKFQK
```

-continued

```
181
                                 *
PHARMAQ001  LGGKIPQGVL IVGPPGTGKT LLAKAIAGEA KVPFFSISGS DFVEMFVGVG ASRVRDMFDQ
LF-89       LGGKIPQGVL MVGPPGTGKT LLAKAIAGEA KVPFFSISGS DFVEMFVGVG ASRVRDMFDQ
EM-90       LGGKIPQGVL MVGPPGTGKT LLAKAIAGEA KVPFFSISGS DFVEMFVGVG ASRVRDMFDQ
B1_32597    LGGKIPQGVL MVGPPGTGKT LLAKAIAGEA KVPFFSISGS DFVEMFVGVG ASRVRDMFDQ
A1_15972    LGGKIPQGVL MVGPPGTGKT LLAKAIAGEA KVPFFSISGS DFVEMFVGVG ASRVRDMFDQ
AL10016     LGGKIPQGVL MVGPPGTGKT LLAKAIAGEA KVPFFSISGS DFVEMFVGVG ASRVRDMFDQ
AL10008     LGGKIPQGVL MVGPPGTGKT LLAKAIAGEA KVPFFSISGS DFVEMFVGVG ASRVRDMFDQ
AL20218     LGGKIPQGVL MVGPPGTGKT LLAKAIAGEA KVPFFSISGS DFVEMFVGVG ASRVRDMFDQ
AL20219     LGGKIPQGVL MVGPPGTGKT LLAKAIAGEA KVPFFSISGS DFVEMFVGVG ASRVRDMFDQ
AL20220     LGGKIPQGVL MVGPPGTGKT LLAKAIAGEA KVPFFSISGS DFVEMFVGVG ASRVRDMFDQ
AL20223     LGGKIPQGVL MVGPPGTGKT LLAKAIAGEA KVPFFSISGS DFVEMFVGVG ASRVRDMFDQ
AL20470     LGGKIPQGVL MVGPPGTGKT LLAKAIAGEA KVPFFSISGS DFVEMFVGVG ASRVRDMFDQ
AL20471     LGGKIPQGVL MVGPPGTGKT LLAKAIAGEA KVPFFSISGS DFVEMFVGVG ASRVRDMFDQ
AL20455     LGGKIPQGVL MVGPPGTGKT LLAKAIAGEA KVPFFSISGS DFVEMFVGVG ASRVRDMFDQ

241
PHARMAQ001  AKKRAPCIIF IDEIDAVGRH RGSGMGGGHD EREQTLNQML VEMDGFEGTE GVIVIAATNR
LF-89       AKKRAPCIIF IDEIDAVGRH RGSGMGGGHD EREQTLNQML VEMDGFEGTE GVIVIAATNR
EM-90       AKKRAPCIIF IDEIDAVGRH RGSGMGGGHD EREQTLNQML VEMDGFEGTE GVIVIAATNR
B1_32597    AKKRAPCIIF IDEIDAVGRH RGSGMGGGHD EREQTLNQML VEMDGFEGTE GVIVIAATNR
A1_15972    AKKRAPCIIF IDEIDAVGRH RGSGMGGGHD EREQTLNQML VEMDGFEGTE GVIVIAATNR
AL10016     AKKRAPCIIF IDEIDAVGRH RGSGMGGGHD EREQ?----- ---------- ----------
AL10008     AKKRAPCIIF IDEIDAVGRH RGSGMGGGHD EREQ?----- ---------- ----------
AL20218     AKKRAPCIIF IDEIDAVGRH RGSGMGGGHD EREQ?----- ---------- ----------
AL20219     AKKRAPCIIF IDEIDAVGRH RGSGMGGGHD EREQ?----- ---------- ----------
AL20220     AKKRAPCIIF IDEIDAVGRH RGSGMGGGHD EREQ?----- ---------- ----------
AL20223     AKKRAPCIIF IDEIDAVGRH RGSGMGGGHD EREQ?----- ---------- ----------
AL20470     AKKRAPCIIF IDEIDAVGRH RGSGMGGGHD EREQ?----- ---------- ----------
AL20471     AKKRAPCIIF IDEIDAVGRH RGSGMGGGHD EREQ?----- ---------- ----------
AL20455     AKKRAPCIIF IDEIDAVGRH RGSGMGGGHD EREQ?----- ---------- ----------

301
PHARMAQ001  PDVLDPALLR PGRFDRQVSV GLPDVKGREQ ILKVHMRKVP LGDDVKASLI ARGTPGFSGA
LF-89       PDVLDPALLR PGRFDRQVSV GLPDVKGREQ ILKVHMRKVP LGDDVKASLI ARGTPGFSGA
EM-90       PDVLDPALLR PGRFDRQVSV GLPDVKGREQ ILKVHMRKVP LGDDVKASLI ARGTPGFSGA
B1_32597    PDVLDPALLR PGRFDRQVSV GLPDVKGREQ ILKVHMRKVP LGDDVKASLI ARGTPGFSGA
A1_15972    PDVLDPALLR PGRFDRQVSV GLPDVKGREQ ILKVHMRKVP LGDDVKASLI ARGTPGFSGA
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
AL20471     ---------- ---------- ---------- ---------- ---------- ----------
AL20455     ---------- ---------- ---------- ---------- ---------- ----------

361
PHARMAQ001  DLANLVNEAA LFAARKDKTV VAMREFDDAK DKILMGTERR SMAMTEEQKR LTAFHEAGHA
LF-89       DLANLVNEAA LFAARKDKTV VAMREFDDAK DKILMGTERR SMAMTEEQKR LTAFHEAGHA
EM-90       DLANLVNEAA LFAARKDKTV VAMREFDDAK DKILMGTERR SMAMTEEQKR LTAFHEAGHA
B1_32597    DLANLVNEAA LFAARKDKTV VAMREFDDAK DKILMGTERR SMAMTEEQKR LTAFHEAGHA
A1_15972    DLANLVNEAA LFAARKDKTV VAMREFDDAK DKILMGTERR SMAMTEEQKR LTAFHEAGHA
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
AL20471     ---------- ---------- ---------- ---------- ---------- ----------
AL20455     ---------- ---------- ---------- ---------- ---------- ----------

421
PHARMAQ001  IVGCLVPDHD PVYKVSIVPR GRALGVTMYL PEEDSYGYSR ERLESLISSM YGGRIAEALV
LF-89       IVGCLVPDHD PVYKVSIVPR GRALGVTMYL PEEDSYGYSR ERLESLISSM YGGRIAEALV
EM-90       IVGCLVPDHD PVYKVSIVPR GRALGVTMYL PEEDSYGYSR ERLESLISSM YGGRIAEALV
B1_32597    IVGCLVPDHD PVYKVSIVPR GRALGVTMYL PEEDSYGYSR ERLESLISSM YGGRIAEALV
A1_15972    IVGCLVPDHD PVYKVSIVPR GRALGVTMYL PEEDSYGYSR ERLESLISSM YGGRIAEALV
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
```

-continued

```
AL20471     ---------- ---------- ---------- ---------- ---------- ----------
AL20455     ---------- ---------- ---------- ---------- ---------- ----------

481
PHARMAQ001  FGVEKVTTGA SNDIEKASEV ARNMVTKWGL SERLGPILYG QEGGDPFGYG AGKGTPEFSD
LF-89       FGVEKVTTGA SNDIEKASEV ARNMVTKWGL SERLGPILYG QEGGDPFGYG AGKGTPEFSD
EM-90       FGVEKVTTGA SNDIEKASEV ARNMVTKWGL SERLGPILYG QEGGDPFGYG AGKGTPEFSD
B1_32597    FGVEKVTTGA SNDIEKASEV ARNMVTKWGL SERLGPILYG QEGGDPFGYG AGKGTPEFSD
A1_15972    FGVEKVTTGA SNDIEKASEV ARNMVTKWGL SERLGPILYG QEGGDPFGYG AGKGTPEFSD
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
AL20471     ---------- ---------- ---------- ---------- ---------- ----------
AL20455     ---------- ---------- ---------- ---------- ---------- ----------

541
PHARMAQ001  QTSVAIDEEV RQIIDRNYTR AESILINNRD ILDAMADALM VYETIDRDQV ADLMARRPVK
LF-89       QTSVAIDEEV RQIIDRNYTR AESILINNRD ILDAMADALM VYETIDRDQV ADLMARRPVK
EM-90       QTSVAIDEEV RQIIDRNYTR AESILINNRD ILDAMADALM VYETIDRDQV ADLMARRPVK
B1_32597    QTSVAIDEEV RQIIDRNYTR AESILIDNRD ILDAMADALM VYETIDREQV ADLMARRPVK
A1_15972    QTSVAIDEEV RQIIDRNYTR AESILINNRD ILDAMADALM VYETIDRDQV ADLMARRPVK
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
AL20471     ---------- ---------- ---------- ---------- ---------- ----------
AL20455     ---------- ---------- ---------- ---------- ---------- ----------

601
PHARMAQ001  APKDWDQPSD ESGSSASGDE LQPLDANINT DINETKSADQ ETDQGAPSPE IKGKPADDPT
LF-89       APKDWDQPSD ESGSSASGDE LQPLDANINT DINETKSADQ ETDQGAPSPE IKGKPADDPT
EM-90       APKDWDQPSD ESGSSASGDE LQPLDANINT DINETKSADQ ETDQGAPSPE IKGKPADDPT
B1_32597    APKDWDQPSD ESGSSASGDE LQPLDANINT DINDTKSADQ EIDQGAPSPE IKGKPADDPT
A1_15972    APKDWDQPSD ESGSSASGDE LQPLDANINT DINETKSADQ ETDQGAPSPE IKGKPADDPT
AL10016     ---------- ---------- ---------- ---------- ---------- ----------
AL10008     ---------- ---------- ---------- ---------- ---------- ----------
AL20218     ---------- ---------- ---------- ---------- ---------- ----------
AL20219     ---------- ---------- ---------- ---------- ---------- ----------
AL20220     ---------- ---------- ---------- ---------- ---------- ----------
AL20223     ---------- ---------- ---------- ---------- ---------- ----------
AL20470     ---------- ---------- ---------- ---------- ---------- ----------
AL20471     ---------- ---------- ---------- ---------- ---------- ----------
AL20455     ---------- ---------- ---------- ---------- ---------- ----------

661
PHARMAQ001  * (Seq. ID No. 53)
LF-89       * (Seq. ID No. 54)
EM-90       * (Seq. ID No. 55)
B1_32597    * (Seq. ID No. 56)
A1_15972    * (Seq. ID No. 57)
AL10016     - (Seq. ID No. 58)
AL10008     - (Seq. ID No. 59)
AL20218     - (Seq. ID No. 60)
AL20219     - (Seq. ID No. 61)
AL20220     - (Seq. ID No. 62)
AL20223     - (Seq. ID No. 63)
AL20470     - (Seq. ID No. 64)
AL20471     - (Seq. ID No. 65)
AL20455     - (Seq. ID No. 66)
```

The FtsH amino acid sequence alignment reveals that there are natural polymorphisms of the FtsH gene product between wild-type strains. However, all of the wild-type strains are virulent and therefore none of the differences between the wild-type sequences can be considered to affect virulence. PHARMAQ 001 has a methionine to isoleucine mutation at position 191 of the amino acid sequence which is not seen in any of the wild-type strains investigated, such as A1-15972, B1-32597, EM-90, and/or LF-89. The protein sequence of the FtsH gene product in PHARMAQ 001 is otherwise identical to that of wild-type strains including A1-15972, EM-90, and LF-89. The sequences of 13 wild-type strains were examined in the region of amino acid residues 152-274 of the FtsH gene product. All of the sequences were found to be identical in this region, but different to that of PHARMAQ 001.

It is clear from the alignments that *P. salmonis* gene products are very highly conserved in all of the strains investigated. As would be expected, there are natural polymorphisms in the genes wherein some of the wild-type strains have a sequence that is different from that of other wild-type strains. However, since all the strains except PHARMAQ 001 are virulent, these differences cannot contribute to the loss of virulence and consequent attenuated phenotype observed in PHARMAQ 001.

PHARMAQ 001 has mutations in the amino acid sequence of the rpoD, FecR, ATP-grasp domain protein, and FtsH gene products relative to the wild-type sequence, and also has an attenuated phenotype. These mutations are the only mutations observed in PHARMAQ 001 which lead to a significant alteration in the amino acid sequence of a protein, and they are not observed in any of the virulent strains investigated.

In a *P. salmonis* strain with an attenuated phenotype, if a mutation is observed in one of the rpoD, FecR, ATP-grasp domain protein, or FtsH genes which is also present in a virulent wild-type strain, then the mutation cannot be responsible for the attenuated phenotype. Mutations, and in particular attenuating mutations, in the rpoD, FecR, ATP-grasp domain protein, or FtsH genes are therefore only significant if they lead to a difference in the amino acid sequence of the gene product relative to the protein sequence of one of the virulent wild-type strains, such as A1-15972, B1-32597, EM-90, and/or LF-89.

Example 3: Phylogeny of *Piscirickettsia salmonis*

To classify the *Piscirickettsia salmonis* isolates in Table 1, a simplified MLSA-scheme was used employing the genetic information within the arginine N-succinyltransferase (ast), glutamate-1-semialdehyde aminotransferase (hemL), L-serine dehydratase (sdhL), and UDP-glucose-4-epimerase (galE) genes for phylogenetic predictions (as annotated in the genome of A1-15972). Sequence information was obtained by standard PCR and sequencing. DNA sequences were assembled, quality checked and trimmed using Vector NTI® software. Sequences for the strains A1-15972, B1-32597, LF-89 and EM-90 were retrieved from GenBank. Sequence information from the four genes for each strain were trimmed and concatenated before alignment.

Sequence alignments and phylogenetic predictions were performed in MEGA5, as described in Tamura et al. (Mol Biol Evol. 2011 October; 28(10): 2731-9, incorporated herein by reference), with the following parameters:

Statistical Method: Maximum Likelihood (100 Bootstrap Replications)

Substitution Model: Tamura-Nei model

Rates: Gamma distributed with Invariant sites (16 Discrete Gamma Categories)

Figure 2:
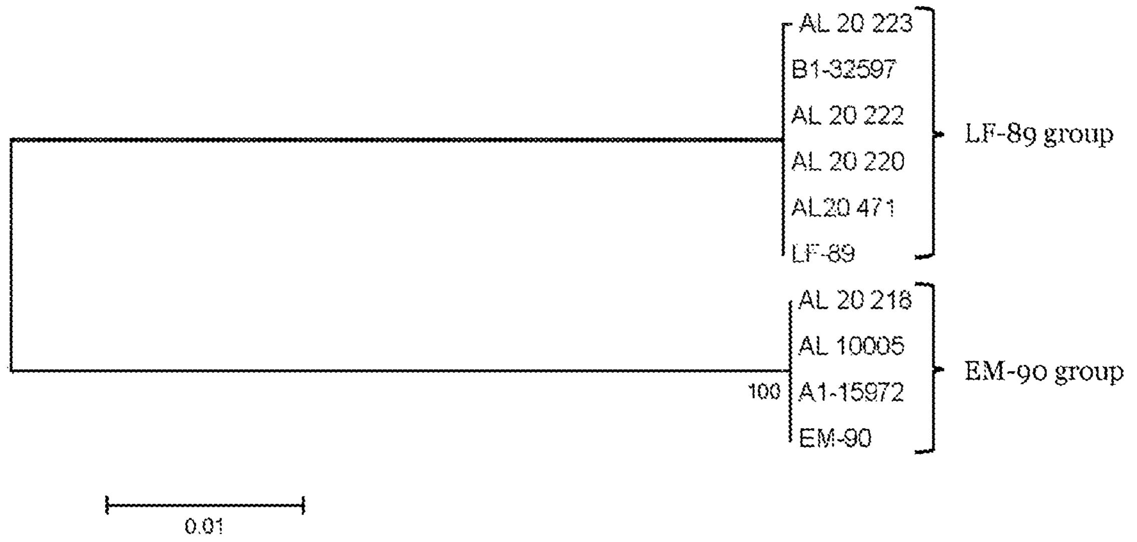
FIG. 2 illustrates phylogeny of *Piscirickettsia salmonis.*

Upon phylogenetic analysis of DNA sequences from the four genes above, two distinct and separate genotypes were identified. The two genotypes are here referred to as the LF-89 group and the EM-90 group. PHARMAQ 001 was found to group together with the EM-90 group. The LF-89 sequence used in the preparation of the phylogenetic tree was the genomic sequence deposited under GenBank accession no. AMGC00000000.1. See FIG. 2.

Example 4: Avirulence of Isolate PHARMAQ 001 when Used as a Live Attenuated Vaccine PHARMAQ 001 was cultivated in insect cell medium to an $OD_{600\ nm}$=3.0 before the addition of a cryoprotectant and storage at −80° C. The bacterial content was determined to be $2.6\times10^8$ $TCID_{50}$/ml by end-point titration.

An ampoule of frozen isolate PHARMAQ 001 was thawed at room temperature and a 0.1 ml dose containing $1.3\times10^7$ $TCID_{50}$/ml was injected intraperitoneally into Atlantic salmon with an average weight of 25-30 grams.

The fish were held at 15° C. for 44 days in freshwater. No fish died or showed any clinical signs of SRS.

Tissue samples (from head kidney and spleen) from vaccinated fish were taken every week for three weeks after vaccination. The presence of bacterial genomes in the tissue samples was analyzed by real time quantitative-PCR. The results are shown in Table 2.

TABLE 2

| | Mean Ct values (9 fish per group) | |
|---|---|---|
| Days post-vaccination | head kidney | Spleen |
| 7 | 28.54 | 28.72 |
| 14 | 30.17 | 29.42 |
| 21 | 31.69 | 29.80 |

As shown in Table 2, the presence of PHARMAQ 001 genomes was generally found to peak at 7 days post vaccination with Ct values around 28.

This experiment demonstrates that PHARMAQ 001 is avirulent and does not induce any symptoms of SRS. Therefore, PHARMAQ 001 is safe and suitable for use as an attenuated live vaccine.

Example 5: Vaccination with PHARMAQ 001 and Challenge with a Virulent *P. salmonis* Isolate To examine the efficacy of the *P. salmonis* isolate PHARMAQ 001 as a vaccine against SRS, Rainbow trout (*Oncorhynchus mykiss*) with an average weight of 30 grams were injected with different doses of the vaccine isolate. The vaccine isolate was either preserved as a frozen vaccine and then diluted in PBS for use at a concentration of $2\times10^5$ $TCID_{50}$, or as a lyophilized vaccine and then diluted in PBS for use at a concentration of $5.2\times10^6$ $TCID_{50}$ per fish.

After an immunization period in fresh water for 504 degree days, the trout were challenged with a highly virulent wild-type strain of *P. salmonis*. The virulent wild-type strain was injected intraperitoneally and the fish were observed for 34 days, as shown in FIG. 1.

FIG. 1 shows the accumulated mortality following challenge with a virulent *P. salmonis* strain.

The attenuated *P. salmonis* strain PHARMAQ 001 was found to work well as a live attenuated vaccine, and provided 100% protection against SRS.

In addition, the study shows that PHARMAQ 001 can be either frozen or lyophilized prior to being used as a vaccine.

Example 6: Passage of Attenuated *P. salmonis* Strain PHARMAQ 001 in Fish Shows Safety of the Vaccine Strain To investigate the potential for reversion to virulence, the isolate PHARMAQ 001 was serially passaged through Atlantic salmon. The trial was performed in fresh water at 15° C. Atlantic salmon were injected with isolate PHARMAQ 001. Homogenates were prepared from head kidneys 7 days after injection, and new Atlantic salmon were injected with the homogenate.

After a further 7 days, homogenates were prepared from the head kidneys of the second fish, and further Atlantic salmon were injected with the homogenate.

No mortality or clinical signs of SRS were observed in any fish during the trial.

The liver from fish from each passage was homogenized, and homogenates were tested for the presence of live *P. salmonis* by plating onto CHAB agar plates. Bacteria were only detected after the first passage.

The bacterial loads in liver and spleen were investigated by measuring the presence of *P. salmonis* genomes by real time quantitative PCR one week after injection of PHARMAQ 001 or homogenate. The results (shown in Table 3) demonstrate that the bacterial loads in spleen and liver were reduced when head kidney homogenates were passaged from the first injected fish into passages 2 and 3 of fish.

TABLE 3

| | Initial injection | Passage 2 | Passage 3 |
|---|---|---|---|
| Liver | 28.9 | nd | nd |
| Spleen | 28.2 | 32.8 | nd |

Nd = not detected

This experiment shows that PHARMAQ 001 does not revert to a virulent strain after serial passage in Atlantic salmon. PHARMAQ 001 is therefore suitable for use as a live attenuated vaccine.

Example 7: Culturing PHARMAQ 001 in Spinner Flask

Bacterial cultures were grown in ExCell Titer High medium from Sigma with no supplements. The cultures were incubated in ventilated spinner flasks at 75 rpm and 20° C., 2 passages after thawing. The growth was monitored by $OD_{600\ nm}$ measurement.

TABLE 4

| Step | Media | pH | Ventilation | Stirring | Temp | Vol. of Inoculum | Time | End $OD_{600}$ |
|---|---|---|---|---|---|---|---|---|
| 1. Spinner flask | ExCell TiterHigh | Not controlled | Ventilated cap | 75 rpm | 20° C. | 1% | 3 days | 3.3 |
| 2. Spinner flask | ExCell TiterHigh | Not controlled | Ventilated cap | 75 rpm | 20° C. | 1% | 2 days | 4.4 |

The results shown in Table 4 demonstrate the cultivation of *P. salmonis* in spinner flasks as the $OD_{600}$ reached 3-4 after 3-4 days of incubation.

Example 8: Culturing PHARMAQ 001 in Spinner Flask

*P. salmonis* strain PHARMAQ 001 was grown in spinner flasks in Sf-900 medium.

PHARMAQ 001 was harvested from the spinner flask and 20% skimmed milk in water (made from dry skimmed milk and heated for 15 minutes at 80° C.) was added 1:1 to the *P. salmonis* culture to a final concentration of 10% skimmed milk. 2 ml of this mixture (*P. salmonis* and 10% skimmed milk) was placed into 10 ml glass vials and then freeze dried in a Labconco FreeZone Triad freeze dryer.

Freeze Drying Cycle:

Freezing: 3 hours hold at −75° C.

Segment 1: ramping rate: 0.1° C./min; holding time: 1 hour; shelf temperature: −40° C.

Segment 2: ramping rate: 0.1° C./min; holding time: 8 hours; shelf temperature: −25° C.

Segment 3: ramping rate: 0.1° C./min; holding time: 24 hours; shelf temperature: −10° C.

Segment 4: ramping rate: 0.1° C./min; holding time: indefinite; shelf temperature: 4° C.

Vacuum was set to 0 μBar in step 1-4

The vials were sealed under vacuum and the process was stopped. The freeze-dried materials were stored at 2-8° C.

To determine the viability of the samples, titration ($TCID_{50}$/ml) was performed on the culture at harvest and after freeze drying. The freeze-dried cake was rehydrated with 2 ml PBS before titration.

Titer ($TCID_{50}$/ml) at harvest: $8.7\times10^9$ cells/ml

Titer ($TCID_{50}$/ml) after freeze drying: $3.2\times10^7$ cells/ml

Thus, after freeze drying, the samples are sufficiently viable for use as a vaccine.

Example 8: Detecting PHARMAQ 001 Strain

The attenuated live strain of *P. salmonis* (rpoD/FecR/ATP-grasp domain protein/FtsH) has been shown to be well tolerated in healthy fish hosts and to colonise the host in a manner consistent with its utility as an effective vaccine to protect against SRS. It has also been demonstrated to elicit a specific immune response. The PHARMAQ 001 live attenuated *P. salmonis* strain has been found to be particularly effective for this purpose.

An assay was developed for identifying and detecting the PHARMAQ 001 strain of *P. salmonis*. The genome of the PHARMAQ 001 strain contains single nucleotide polymorphisms (SNP) in each of the rpoD, FecR, ATP-grasp domain protein, and FtsH genes, each of which results in a chemically significant alteration of the amino acid sequence of the resulting gene product. The assay involves typing each of these single nucleotide polymorphisms, and determining whether the wild-type or mutant allele is present.

Specifically, the assay involves using target-specific PCR primers to amplify the nucleic acid sequence in the region of the SNP. Separate probes specific for each of the wild-type and mutant alleles are included in the reaction mix. Each probe is labelled with a different detectable marker such as a fluorescent dye. In the example described below, the probe specific for the wild-type sequence was labelled with the FAM fluorophore, and the probe specific for the mutant sequence was labelled with the VIC fluorescent dye. An overview of the primers and probes used for each SNP analysis is shown in Table 5. In the present example, the SNP analysis was performed using the ABI PRISM® 7900 HT Sequence Detection System.

TABLE 5

| Target Gene | Primer/Probe | Sequence | Seq. ID No. |
|---|---|---|---|
| rpoD | Fwd | GGACAATCCGGATTCCTGTACATAT | 67 |
| | VProbe1-VIC Mutant Allele | ACAAGCTTACC**T**GCGTCTC | 68 |
| | MProbe2-FAM Wild-Type Allele | AAGCTTAAC**C**GCGTCTC | 69 |
| | Rev | GCCGAGTTCTTGGATCATTTGAC | 70 |
| ATP-grasp domain protein | Fwd | TGGCGATGGTGCGTCTAC | 71 |
| | VProbe1-VIC Mutant Allele | CCATCAG**G**GAGCCGAG | 72 |
| | MProbe2-FAM Wild-Type Allele | CCATCAG**A**GAGCCGAG | 73 |
| | Rev | CGCCAATTGCACCTTGATGAAG | 74 |
| FtsH | Fwd | CCAAAAGTTAGGCGGCAAAATTCC | 75 |
| | VProbe1-VIC Mutant Allele | TGGGCCAAC**T**ATCA | 76 |
| | MProbe2-FAM Wild-Type Allele | TGGGCCAAC**C**ATCA | 77 |
| | Rev | GCTAATAGCGTCTTACCTGTTCCA | 78 |

RNA was isolated from cultures of *P. salmonis*, including PHARMAQ 001 and wild type strains including the virulent starting strain. The samples were prepared as shown in Table 6. All tests were performed using QuantiTect Probe RT-PCR kit (Qiagen).

TABLE 6

| Reagent | Final concentration |
|---|---|
| 2X Master mix (Recommended by kit supplier, contains dNTPs, MgCl2 (final concentration 4 mM), HotStartTaq DNA Polymerase, and passive reference dye (ROX) | 1x |
| Forward primer | 900 nM (0.9 µl of 1.0 µM solution) |
| Reverse Primer | 900 nM (0.9 µl of 1.0 µM solution) |
| VProbe-VIC | 200 nM (0.2 µl of 1.0 µM solution) |
| MProbe-FAM | 175 nM (0.175 µl of 1.0 µM solution) |
| RT-Enzyme mix (QuantiTect) | 0.1 µl |
| Template | 1 pg to 1 µg per reaction |
| $dH_2O$ | To 10 µl |

Samples were analysed in triplicates on 384-well plates. Each plate was subjected to a pre-read, for determination of background fluorescence in each well prior to the real-time RT-PCR step. The real-time RT-PCR was performed using standard enzymes and buffers, with the parameters shown in Table 7.

TABLE 7

| Step | Temperature | Time | Cycles |
|---|---|---|---|
| 1) Reverse transcription | 50° C. | 30 minutes | 1 |
| 2) DNA polymerase activation | 95° C. | 15 minutes | 1 |
| 3) Denaturation, Annealing and extension | 94° C.<br>60° C. | 15 seconds<br>1 minute | 45 |

All primers and probes were optimized to allow annealing and extension at 60° C. This temperature is also believed to be significant for the competition between the two probes in the SNP assay, as it leads to binding and cleavage of the correct probe as well as destabilization of the incorrect probe, depending on the SNP at the probe site.

After the real-time RT-PCR reaction had been performed, the plate was subjected to an end-point analysis, by performing a post-read of the fluorescence in each well, and comparing the result to the data stored from the pre-read. The results are shown in Table 8 (in which a plus sign indicates a cycle threshold of less than or equal to 30 and a minus sign indicates no detectable fluorescent signal).

TABLE 8

| | rpoD | | ATP-grasp domain protein | | FtsH | |
|---|---|---|---|---|---|---|
| | VProbe1-VIC Mutant Allele | MProbe2-FAM Wild-Type Allele | VProbe1-VIC Mutant Allele | MProbe2-FAM Wild-Type Allele | VProbe1-VIC Mutant Allele | MProbe2-FAM Wild-Type Allele |
| PHARMAQ 001, attenuated vaccine strain | + | − | + | − | + | − |
| Virulent starting strain | − | + | − | + | − | + |
| Wild type *P. salmonis* strain A | − | + | − | + | − | + |
| Wild type *P. salmonis* strain B | − | + | − | + | − | + |
| Wild type *P. salmonis* strain C | − | + | − | + | − | + |

The assay clearly identified each of the mutant alleles in the PHARMAQ 001 strain, and also identified the presence of the wild-type allele in all wild type strains tested. For all tests, the discrimination between the two allelic variants was very good. The assay permits clear distinction between wild type and PHARMAQ 001 *P. salmonis* strains.

In order to address various issues and advance the art, the entirety of this disclosure shows by way of illustration various embodiments in which the claimed invention may be practiced and provide for an attenuated *P. salmonis* bacterium and an improved *P. salmonis* vaccine. The advantages and features of the disclosure are of a representative sample of embodiments only, and are not exhaustive and/or exclusive. They are presented only to assist in understanding and teach the claimed features. It is to be understood that advantages, embodiments, examples, functions, features, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An attenuated *Piscirickettsia salmonis* bacterium comprising: a) an arginine to cysteine mutation at position 473 of the rpoD gene product, provided as Seq. ID No. 17; b) a premature stop codon at the position corresponding to a residue at a position between residue 39 and residue 83 of the FecR gene product, provided as Seq. ID No. 26; c) a serine to proline mutation at position 184 of the ATP-grasp domain protein gene product, provided as Seq. ID No. 40; and, d) a methionine to isoleucine mutation at position 191 of the FtsH gene product, provided as Seq. ID No. 54.

2. The attenuated bacterium of claim 1, comprising a premature stop codon at the position corresponding to residue 83 of the FecR gene product, provided as Seq. ID No. 26.

3. An attenuated *Piscirickettsia salmonis* bacterium comprises the strain PHARMAQ 001 deposited with the European Collection of Cell Cultures, Public health England, Culture Collections, Porton Down, Salisbury SP4 OJG, United Kingdom, on 9 Oct. 2014 with accession number 14100901.

4. A live, attenuated vaccine composition comprising: (a) an attenuated *Piscirickettsia salmonis* bacterium as claimed in either claim 1 or 3; and (b) a pharmaceutically acceptable carrier or diluent.

5. A live, attenuated vaccine composition as claimed in claim 4, in freeze-dried form.

6. A method of producing the attenuated bacterium of claim 1, the method comprising:

a) subjecting an initial population of *P. salmonis* bacteria to attenuating conditions to produce a putatively attenuated bacterial population;

b) identifying clones of the putatively attenuated bacterial population that have mutations in the amino add sequences of all of the rpoD, FecR, ATP-grasp domain protein, and FtsH gene products; and, c) identifying and selecting clones that have mutations in the amino add sequence of all of the rpoD, FecR, ATP-grasp domain protein, and FtsH gene products and that also exhibit reduced virulence relative to wild-type bacteria of the genus *Piscirickettsia*, wherein said mutations comprise: i) an arginine to cysteine mutation at position 473 of the rpoD gene product, provided as Seq. ID No. 17; ii) a premature stop codon at the position corresponding to a residue at a position between residue 39 and residue 83 of the FecR gene product, provided as Seq. ID No. 26; iii) a serine to proline mutation at position 184 of the ATP-grasp domain protein gene product, provided as Seq. ID No. 40; and, iv) a methionine to isoleucine mutation at position 191 of the FtsH gene product, provided as Seq. ID No. 54.

7. A method of raising an immune response in a fish, the method comprising administering to the fish the attenuated *Piscirickettsia salmonis* bacterium either one of claim 1 or 3.

* * * * *

SEQUENCE LISTING

```
<160> NUMBER OF SEQ ID NOS: 78

<210> SEQ ID NO 1
<211> LENGTH: 1872
<212> TYPE: DNA
<213> ORGANISM: Piscirickettsia salmonis

<400> SEQUENCE: 1

atggatcaac aagaaaaaag gtcgcagttt aaagaactca ttgttcgagg taaacagcaa     60

ggctttttaa cgtttacaga ggtaaacgat catcttccgg atgatatgag cagcccggaa    120

gaagttgaag agatcgttgc aatgattagc gacatgggca tccccgtcta tgaaactgca    180

cccgatcctg acagcttact catgaatgag catgccagct ctgccgaaga tgatgctgac    240

gatgccgttg cagcgctcga ttcagatgct gagtttgggc gaacaaccga cccagtacgc    300

atgtatatgc gcgagatggg cagcgttgag ctattaacgc gccaaggtga aattgagctg    360

gctaaacgca tcgaggaagg cgtcaaacaa gcctttgagg caatcgccca ttacccacaa    420

agcacagcga ttattcttga agaatatgca agatttgaag ccgaagaaat ccgtttagat    480

gatattatca gtggctatat caccgaagaa gatgaagctc cgacaagcaa catcggctcc    540

atgcttgatg atgccaataa agccgatgat aattttgaag ccgccttgac agaagacgac    600

agtactgatg acggtgaggg tgaggatgac aatgaagaaa tccccgtcga taacacattg    660

gatgttgagg aagcggcaga gcgttttgcc gagctaaaag ctgcctatga tgcggttata    720

caggttcagg aaaaacacgg aattcatcat aaaaaaacac aacagcgttg tgaagaactg    780

tctaaagtat taatgacatt tcgcctaaag cccaatatga tcgataaaat caccaactac    840

ttacatggct tactcagcca agtccgcaaa catgagcgtc acatcatggc tttgtgcatt    900

aatcaagcga aaatgccccg caagctattt attgatattt tcccaggcaa tgaaaccaat    960

ctagagtgga tagagtatca aattaaagcc gagcaatctt actctgaagc actacagtcc   1020

ctggctccag aagtcactcg tgcacagaaa aagctcatct ctcttgaaca agaatcaaac   1080

tttgatgtca ctgcaattaa agaagtcaat cgtaatattt ctattggtga ggccaaggcc   1140

catcgtgcta aaaaagaaat ggtcgaagct aacttgcgtc tggtcatctc cattgcaaaa   1200

aaatacacca atcgaggctt acaatttctc gacctcattc aagaaggcaa tattggccta   1260

atgaaagcgg tagataaatt cgaataccgc cgtggttata aattctcaac gtatgcaaca   1320

tggtggattc gccaggcaat tacccgctca attgctgatc aagcgcggac aatccggatt   1380

cctgtacata tgatagagac aattaacaag cttaactgcg tctcacgtca aatgatccaa   1440

gaactcggcc gtgaagcgac tcctgaggag ctttctgaac gcatggagat gccagagcat   1500

aaaatccgta aaatcctcaa aatcgctaaa gagccaattt ctatggaaac accgattggc   1560
```

gatgacgaag attcacactt aggtgatttt attgaagata ccaccatgca actccccgtt 1620
gactcaacca tgggtgatgc gttaaagcaa gccaccagtg atattctcga aaacctcacg 1680
ccacgtgaag caaaagtcct tagaatgcgc tttggtatcg atatgaatac tgaccatacg 1740
ctagaggaag ttggcaaaca atttgacgta actcgcgagc gtattcgcca aattgaagcc 1800
aaagccttac gtaaactgcg ccacccaact cgctcagaaa ttttgaagag ttttcttgac 1860
tcagaagaat aa 1872

<210> SEQ ID NO 2
<211> LENGTH: 20
<212> TYPE: DNA
<213> ORGANISM: Artificial Sequence
<220> FEATURE:
<223> OTHER INFORMATION: PCR Primer: Forward rpoD

<400> SEQUENCE: 2
ccaggcaatt acccgctcaa 20

<210> SEQ ID NO 3
<211> LENGTH: 20
<212> TYPE: DNA
<213> ORGANISM: Artificial Sequence
<220> FEATURE:
<223> OTHER INFORMATION: PCR primer: Reverse rpoD

<400> SEQUENCE: 3
tcgccaatcg gtgtttccat 20

<210> SEQ ID NO 4
<211> LENGTH: 657
<212> TYPE: DNA
<213> ORGANISM: Piscirickettsia salmonis

<400> SEQUENCE: 4
atgaaaatta atcatcagcc tggcggcata atgttgataa tgaataatca tggtgaagtg 60
atgacaagct actcacatat gatgattttt ttttcaaatt atggcgaaaa agtaaagatt 120
gagaatcagc gtatcttaaa tgataataaa ctgctattta gtaatagagt gagtagggtg 180
cgttatcggc cttgtcttat tattgatgca aaagatgctt tatcagtctg ttctggcgtg 240
tttcattaag taaaaaatga attcggagtt gttgttgcaa gctctcttaa tgtgatgata 300
tacgattata aatcaatgtc agatgaggat attattcata ttttaaagtc tgtcaaaaaa 360
catccaaaat tatctttaat agaaagcaag atactttttt taaaagtggt aatgaaaggg 420
ataaaatgtc gccatattga gtcgttactt aaggtatccg gaagtactgt gtatacgtat 480
tgtatgaata tcaagtcaaa agcaaatatt tttagtttta aagggcagtc cgtaattcag 540
gaattagaaa aaagtcaatt ttttagtgat atttctataa agataaatat agatttctat 600
aacattaata atggagtaaa tgagaaaaat gtttgccaag tatatagcct agcttaa 657

<210> SEQ ID NO 5
<211> LENGTH: 22
<212> TYPE: DNA
<213> ORGANISM: Artificial Sequence
<220> FEATURE:
<223> OTHER INFORMATION: PCR Primer: Forward FecR

<400> SEQUENCE: 5
tggtgaagtg atgacaagct ac 22

-continued

<210> SEQ ID NO 6
<211> LENGTH: 22
<212> TYPE: DNA
<213> ORGANISM: Artificial Sequence
<220> FEATURE:
<223> OTHER INFORMATION: PCR Primer: Reverse FecR

<400> SEQUENCE: 6
acacagtact tccggatacc tt 22

<210> SEQ ID NO 7
<211> LENGTH: 951
<212> TYPE: DNA
<213> ORGANISM: Piscirickettsia salmonis

<400> SEQUENCE: 7
atgatcagcc tgtggaagac ctatcaggcg cttaaaacaa agggcatttt aggcattaat 60
cagcgtaatg ctgactttat tattcgctat aatcagcgca aatactaccc tttagtcgat 120
gataaaatca tgacaaaaac ccttgcgatt aaagatggta ttgccgtccc taaattatat 180
gcaaccctta aaactgacca tgatactcac catctggagc aaattttagc caatcgaacg 240
gattttgtca ttaaaccggc ccgtggtgct ggcggtgatg gtattttagt cattaccaac 300
cgccatggtg agcgttttcg caaagtcagt ggtgcactgt tacacttaga cgatattcgt 360
catcacattt ctaatatctt aagtggggta tacagtcttg gtggccaacg tgatcaggcc 420
atgattgaat accgcgtaca atttgatcca ttatttaaaa aaatcagcta tcaaggtgtg 480
cccgatattc gtattattgt cctaaaaggc tatcctgcga tggcgatggt gcgtctaccc 540
actcggctcc ctgatggcaa agccaacctt catcaaggtg caattggcgt tggcattgac 600
ttaacaacag gcatcacctt agaaggtgtt tggatgaatg acccaattca tgaacatccg 660
gatactggct atgctgtacc aggcttacag attcctcact gggatcattt tttaaacctt 720
gctgcacgct gttacgagct tactcaacta ggttatttag gtgtggatat tatccttgat 780
aaagacaaag gcccactcat gcttgagctt aatgcgcgtc ctggtttaaa tattcaaatt 840
gcgaataata gcggcttatt gcatcgatta cgtttcattg agcaacaaaa tcaacaacgc 900
acagccgatg aacgcattgc tttcatcaaa catcagttcg caaaaatata a 951

<210> SEQ ID NO 8
<211> LENGTH: 20
<212> TYPE: DNA
<213> ORGANISM: Artificial Sequence
<220> FEATURE:
<223> OTHER INFORMATION: PCR Primer: Forward ATP-grasp domain protein

<400> SEQUENCE: 8
ggtgagcgtt ttcgcaaagt 20

<210> SEQ ID NO 9
<211> LENGTH: 20
<212> TYPE: DNA
<213> ORGANISM: Artificial Sequence
<220> FEATURE:
<223> OTHER INFORMATION: PCR Primer: Reverse ATP-grasp domain protein

<400> SEQUENCE: 9
tcaagcatga gtgggccttt 20

<210> SEQ ID NO 10
<211> LENGTH: 1983

<212> TYPE: DNA
<213> ORGANISM: Piscirickettsia salmonis

<400> SEQUENCE: 10
atgattaaaa acatcatgct atggctggtc attgctttgg tgttggtgac tgtgtttagt 60
aatttaggcc cacgtcagca gtcggtgaat cggctagatt attcaacatt tgttaaagac 120
atcaataatg gtcaagtaaa aagcgttatc attgatggtt tgaatattaa aggacaaacc 180
tcaagtggga cgccatttgc tacttatatt ccgtggaaag atccattttt aatggatcag 240
atgctggcga aaaatgtcac aattgctgct aaaccacctg agcagcggag ctggttattg 300
tctgcattaa tcagttggtt ccctggtatt ttattaattg cgatttggat tttcttcttg 360
cggcagatgc aaggcggtgg tggtggtaag ggcatgatgt cctttggttc cagtaaggca 420
cgtctgcttg gtgaagatca aattaaagtt aactttgctg atgttgctgg ctgtgaagag 480
gctaaagaag aagtaaaaga actggtcgat tttctgcgtg acccaaccaa attccaaaag 540
ttaggcggca aaattccgca aggggtattg atagttggcc cacctggaac aggtaagacg 600
ctattagcta aagccattgc aggtgaggcg aaagtcccgt tcttttctat ttcaggctct 660
gattttgttg aaatgttcgt cggtgtcggt gcatcgcggg tgcgtgatat gtttgatcag 720
gcaaaaaaac gtgcaccgtg tattatcttt atcgatgaga ttgatgcagt gggccgtcac 780
cgtggctcag gtatgggcgg tggtcatgac gaacgtgagc agaccttaaa tcaaatgctg 840
gtcgagatgg atggttttga gggaaccgaa ggggtgattg tcattgccgc gacgaatcgt 900
ccggatgtat tggacccggc attattgcgt cccgggcgtt ttgatcgcca ggtcagtgtc 960
gggcttcccg atgtcaaagg ccgtgagcag attctaaaag tgcatatgcg taaggtgcct 1020
ttgggagatg atgttaaagc gtcattgatc gcccgtggta cgcctgggtt ctcaggagcg 1080
gatttggcga acttggtcaa tgaagccgca ctctttgccg cgcgtaaaga taaaaccgtg 1140
gttgctatgc gtgagtttga tgatgccaaa gataaaattt tgatgggcac tgagcgccgt 1200
tcgatggcaa tgaccgaaga gcaaaaacgt ttaaccgcct ttcatgaggc agggcacgcg 1260
attgtcgggt gtttggtacc tgatcatgat ccggtgtata aagtctcgat tgtgccgcgg 1320
ggtcgtgcct taggtgtgac catgtatctg cctgaagagg atagttatgg ttattcacgc 1380
gagcgcttgg agagcttaat ttcgagtatg tatggcggac gtattgctga agctttagtc 1440
tttggtgttg agaaagtaac gactggggca tcgaatgaca ttgaaaaagc ctcagaagtg 1500
gcgcgcaata tggtgacaaa gtgggggctg tctgagcgct tagggccgat attatatgga 1560
caagaaggcg gtgatccgtt tggttatggt gcgggtaaag gcacgccgga attttcagat 1620
caaacctctg ttgctattga tgaggaagta cgtcagatca ttgatcgtaa ttatacacgc 1680
gctgagagca ttctaatcaa taatcgggat attcttgatg cgatggcgga tgcgttgatg 1740
gtctatgaga cgattgatcg tgaccaagtg gctgatctaa tggcgcgtcg gccggtgaaa 1800
gcaccgaaag attgggatca gccctctgat gagagtggct catcagcatc tggtgatgag 1860
ttacaacctc ttgatgctaa tatcaatact gatattaatg agactaagag cgctgatcaa 1920
gagacagatc agggcgcgcc gtcaccagaa ataaagggta aaccagcgga tgatcctacc 1980
taa 1983

<210> SEQ ID NO 11
<211> LENGTH: 20
<212> TYPE: DNA
<213> ORGANISM: Artificial Sequence
<220> FEATURE:

-continued

<223> OTHER INFORMATION: PCR Primer: Forward FtsH

<400> SEQUENCE: 11
tggttccagt aaggcacgtc 20

<210> SEQ ID NO 12
<211> LENGTH: 20
<212> TYPE: DNA
<213> ORGANISM: Artificial Sequence
<220> FEATURE:
<223> OTHER INFORMATION: PCR Primer: Reverse FtsH

<400> SEQUENCE: 12
acaatcaccc cttcggttcc 20

<210> SEQ ID NO 13
<211> LENGTH: 623
<212> TYPE: PRT
<213> ORGANISM: Piscirickettsia salmonis

<400> SEQUENCE: 13

Met Asp Gln Gln Glu Lys Arg Ser Gln Phe Lys Glu Leu Ile Val Arg
1 5 10 15

Gly Lys Gln Gln Gly Phe Leu Thr Phe Thr Glu Val Asn Asp His Leu
20 25 30

Pro Asp Asp Met Ser Ser Pro Glu Glu Val Glu Glu Ile Val Ala Met
35 40 45

Ile Ser Asp Met Gly Ile Pro Val Tyr Glu Thr Ala Pro Asp Pro Asp
50 55 60

Ser Leu Leu Met Asn Glu His Ala Ser Ser Ala Glu Asp Asp Ala Asp
65 70 75 80

Asp Ala Val Ala Ala Leu Asp Ser Asp Ala Glu Phe Gly Arg Thr Thr
85 90 95

Asp Pro Val Arg Met Tyr Met Arg Glu Met Gly Ser Val Glu Leu Leu
100 105 110

Thr Arg Gln Gly Glu Ile Glu Leu Ala Lys Arg Ile Glu Glu Gly Val
115 120 125

Lys Gln Ala Phe Glu Ala Ile Ala His Tyr Pro Gln Ser Thr Ala Ile
130 135 140

Ile Leu Glu Glu Tyr Ala Arg Phe Glu Ala Glu Glu Ile Arg Leu Asp
145 150 155 160

Asp Ile Ile Ser Gly Tyr Ile Thr Glu Glu Asp Glu Ala Pro Thr Ser
165 170 175

Asn Ile Gly Ser Met Leu Asp Asp Ala Asn Lys Ala Asp Asp Asn Phe
180 185 190

Glu Ala Ala Leu Thr Glu Asp Asp Ser Thr Asp Asp Gly Glu Gly Glu
195 200 205

Asp Asp Asn Glu Glu Ile Pro Val Asp Asn Thr Leu Asp Val Glu Glu
210 215 220

Ala Ala Glu Arg Phe Ala Glu Leu Lys Ala Ala Tyr Asp Ala Val Ile
225 230 235 240

Gln Val Gln Glu Lys His Gly Ile His His Lys Lys Thr Gln Gln Arg
245 250 255

Cys Glu Glu Leu Ser Lys Val Leu Met Thr Phe Arg Leu Lys Pro Asn
260 265 270

Met Ile Asp Lys Ile Thr Asn Tyr Leu His Gly Leu Leu Ser Gln Val
275 280 285

```
Arg Lys His Glu Arg His Ile Met Ala Leu Cys Ile Asn Gln Ala Lys
    290                 295                 300

Met Pro Arg Lys Leu Phe Ile Asp Ile Phe Pro Gly Asn Glu Thr Asn
305                 310                 315                 320

Leu Glu Trp Ile Glu Tyr Gln Ile Lys Ala Glu Gln Ser Tyr Ser Glu
                325                 330                 335

Ala Leu Gln Ser Leu Ala Pro Glu Val Thr Arg Ala Gln Lys Lys Leu
            340                 345                 350

Ile Ser Leu Glu Gln Glu Ser Asn Phe Asp Val Thr Ala Ile Lys Glu
        355                 360                 365

Val Asn Arg Asn Ile Ser Ile Gly Glu Ala Lys Ala His Arg Ala Lys
    370                 375                 380

Lys Glu Met Val Glu Ala Asn Leu Arg Leu Val Ile Ser Ile Ala Lys
385                 390                 395                 400

Lys Tyr Thr Asn Arg Gly Leu Gln Phe Leu Asp Leu Ile Gln Glu Gly
                405                 410                 415

Asn Ile Gly Leu Met Lys Ala Val Asp Lys Phe Glu Tyr Arg Arg Gly
            420                 425                 430

Tyr Lys Phe Ser Thr Tyr Ala Thr Trp Trp Ile Arg Gln Ala Ile Thr
        435                 440                 445

Arg Ser Ile Ala Asp Gln Ala Arg Thr Ile Arg Ile Pro Val His Met
    450                 455                 460

Ile Glu Thr Ile Asn Lys Leu Asn Cys Val Ser Arg Gln Met Ile Gln
465                 470                 475                 480

Glu Leu Gly Arg Glu Ala Thr Pro Glu Glu Leu Ser Glu Arg Met Glu
                485                 490                 495

Met Pro Glu His Lys Ile Arg Lys Ile Leu Lys Ile Ala Lys Glu Pro
            500                 505                 510

Ile Ser Met Glu Thr Pro Ile Gly Asp Asp Glu Asp Ser His Leu Gly
        515                 520                 525

Asp Phe Ile Glu Asp Thr Thr Met Gln Leu Pro Val Asp Ser Thr Met
    530                 535                 540

Gly Asp Ala Leu Lys Gln Ala Thr Ser Asp Ile Leu Glu Asn Leu Thr
545                 550                 555                 560

Pro Arg Glu Ala Lys Val Leu Arg Met Arg Phe Gly Ile Asp Met Asn
                565                 570                 575

Thr Asp His Thr Leu Glu Glu Val Gly Lys Gln Phe Asp Val Thr Arg
            580                 585                 590

Glu Arg Ile Arg Gln Ile Glu Ala Lys Ala Leu Arg Lys Leu Arg His
        595                 600                 605

Pro Thr Arg Ser Glu Ile Leu Lys Ser Phe Leu Asp Ser Glu Glu
    610                 615                 620


<210> SEQ ID NO 14
<211> LENGTH: 623
<212> TYPE: PRT
<213> ORGANISM: Piscirickettsia salmonis

<400> SEQUENCE: 14

Met Asp Gln Gln Glu Lys Arg Ser Gln Phe Lys Glu Leu Ile Val Arg
1               5                   10                  15

Gly Lys Gln Gln Gly Phe Leu Thr Phe Thr Glu Val Asn Asp His Leu
            20                  25                  30

Pro Asp Asp Met Ser Ser Pro Glu Glu Val Glu Glu Ile Val Ala Met
```

-continued

```
        35                  40                  45

Ile Ser Asp Met Gly Ile Pro Val Tyr Glu Thr Ala Pro Asp Pro Asp
    50                  55                  60

Ser Leu Leu Met Asn Glu His Ala Ser Ser Ala Glu Asp Asp Ala Asp
65                  70                  75                  80

Asp Ala Val Ala Ala Leu Asp Ser Asp Ala Glu Phe Gly Arg Thr Thr
                85                  90                  95

Asp Pro Val Arg Met Tyr Met Arg Glu Met Gly Ser Val Glu Leu Leu
            100                 105                 110

Thr Arg Gln Gly Glu Ile Glu Leu Ala Lys Arg Ile Glu Glu Gly Val
        115                 120                 125

Lys Gln Ala Phe Glu Ala Ile Ala His Tyr Pro Gln Ser Thr Ala Ile
    130                 135                 140

Ile Leu Glu Glu Tyr Ala Arg Phe Glu Ala Glu Glu Ile Arg Leu Asp
145                 150                 155                 160

Asp Ile Ile Ser Gly Tyr Ile Thr Glu Glu Asp Glu Ala Pro Thr Ser
                165                 170                 175

Asn Ile Gly Ser Met Leu Asp Asp Ala Asn Lys Ala Asp Asp Asn Phe
            180                 185                 190

Glu Ala Ala Leu Thr Glu Asp Asp Ser Thr Asp Asp Gly Glu Gly Glu
        195                 200                 205

Asp Asp Asn Glu Glu Ile Pro Val Asp Asn Thr Leu Asp Val Glu Glu
    210                 215                 220

Ala Ala Glu Arg Phe Ala Glu Leu Lys Ala Ala Tyr Asp Ala Val Ile
225                 230                 235                 240

Gln Val Gln Glu Lys His Gly Ile His His Lys Lys Thr Gln Gln Arg
                245                 250                 255

Cys Glu Glu Leu Ser Lys Val Leu Met Thr Phe Arg Leu Lys Pro Asn
            260                 265                 270

Met Ile Asp Lys Ile Thr Asn Tyr Leu His Gly Leu Leu Ser Gln Val
        275                 280                 285

Arg Lys His Glu Arg His Ile Met Ala Leu Cys Ile Asn Gln Ala Lys
    290                 295                 300

Met Pro Arg Lys Leu Phe Ile Asp Ile Phe Pro Gly Asn Glu Thr Asn
305                 310                 315                 320

Leu Glu Trp Ile Glu Tyr Gln Ile Lys Ala Glu Gln Ser Tyr Ser Glu
                325                 330                 335

Ala Leu Gln Ser Leu Ala Pro Glu Val Thr Arg Ala Gln Lys Lys Leu
            340                 345                 350

Ile Ser Leu Glu Gln Glu Ser Asn Phe Asp Val Thr Ala Ile Lys Glu
        355                 360                 365

Val Asn Arg Asn Ile Ser Ile Gly Glu Ala Lys Ala His Arg Ala Lys
    370                 375                 380

Lys Glu Met Val Glu Ala Asn Leu Arg Leu Val Ile Ser Ile Ala Lys
385                 390                 395                 400

Lys Tyr Thr Asn Arg Gly Leu Gln Phe Leu Asp Leu Ile Gln Glu Gly
                405                 410                 415

Asn Ile Gly Leu Met Lys Ala Val Asp Lys Phe Glu Tyr Arg Arg Gly
            420                 425                 430

Tyr Lys Phe Ser Thr Tyr Ala Thr Trp Trp Ile Arg Gln Ala Ile Thr
        435                 440                 445

Arg Ser Ile Ala Asp Gln Ala Arg Thr Ile Arg Ile Pro Val His Met
    450                 455                 460
```

-continued

Ile Glu Thr Ile Asn Lys Leu Asn Arg Val Ser Arg Gln Met Ile Gln
465 470 475 480

Glu Leu Gly Arg Glu Ala Thr Pro Glu Glu Leu Ser Glu Arg Met Glu
485 490 495

Met Pro Glu His Lys Ile Arg Lys Ile Leu Lys Ile Ala Lys Glu Pro
500 505 510

Ile Ser Met Glu Thr Pro Ile Gly Asp Asp Glu Asp Ser His Leu Gly
515 520 525

Asp Phe Ile Glu Asp Thr Thr Met Gln Leu Pro Val Asp Ser Thr Met
530 535 540

Gly Asp Ala Leu Lys Gln Ala Thr Ser Asp Ile Leu Glu Asn Leu Thr
545 550 555 560

Pro Arg Glu Ala Lys Val Leu Arg Met Arg Phe Gly Ile Asp Met Asn
565 570 575

Thr Asp His Thr Leu Glu Glu Val Gly Lys Gln Phe Asp Val Thr Arg
580 585 590

Glu Arg Ile Arg Gln Ile Glu Ala Lys Ala Leu Arg Lys Leu Arg His
595 600 605

Pro Thr Arg Ser Glu Ile Leu Lys Ser Phe Leu Asp Ser Glu Glu
610 615 620

<210> SEQ ID NO 15
<211> LENGTH: 623
<212> TYPE: PRT
<213> ORGANISM: Piscirickettsia salmonis

<400> SEQUENCE: 15

Met Asp Gln Gln Glu Lys Lys Ser Gln Phe Lys Glu Leu Ile Val Arg
1 5 10 15

Gly Lys Gln Gln Gly Phe Leu Thr Phe Thr Glu Val Asn Asp His Leu
20 25 30

Pro Asp Asp Met Ser Ser Pro Glu Glu Val Glu Glu Ile Val Ala Met
35 40 45

Ile Ser Asp Met Gly Ile Pro Val Tyr Glu Thr Ala Pro Asp Pro Asp
50 55 60

Ser Leu Leu Met Asn Glu His Ala Ser Ser Ala Glu Asp Asp Ala Asp
65 70 75 80

Asp Ala Val Ala Ala Leu Gly Ser Asp Ala Glu Phe Gly Arg Thr Thr
85 90 95

Asp Pro Val Arg Met Tyr Met Arg Glu Met Gly Ser Val Glu Leu Leu
100 105 110

Thr Arg Gln Gly Glu Ile Glu Leu Ala Lys Arg Ile Glu Glu Gly Val
115 120 125

Lys Gln Ala Phe Glu Ala Ile Ala His Tyr Pro Gln Ser Thr Ala Ile
130 135 140

Ile Leu Glu Glu Tyr Ala Arg Phe Glu Ala Glu Glu Ile Arg Leu Asp
145 150 155 160

Asp Ile Ile Ser Gly Tyr Ile Thr Glu Glu Asp Glu Ala Pro Thr Ser
165 170 175

Asn Ile Gly Ser Met Leu His Asp Ala Asn Lys Ala Asp Asp Asn Phe
180 185 190

Glu Ala Ala Leu Thr Glu Asp Asp Ser Thr Asp Asp Ala Glu Asp Glu
195 200 205

Gly Asp Asn Glu Glu Ile Pro Val Asp Asn Thr Leu Asp Val Glu Glu

-continued

```
    210                 215                 220

Ala Ala Glu Arg Phe Ala Glu Leu Lys Ala Ala Tyr Asp Ala Val Ile
225                 230                 235                 240

Gln Val Gln Glu Lys His Gly Ile His His Lys Lys Thr Gln Gln Arg
                245                 250                 255

Cys Glu Glu Leu Ser Lys Val Leu Met Thr Phe Arg Leu Lys Pro Asn
            260                 265                 270

Met Ile Asp Lys Ile Thr Asn Tyr Leu His Asp Leu Leu Ser Gln Val
        275                 280                 285

Arg Lys His Glu Arg His Ile Met Ala Leu Cys Ile Asn Gln Ala Lys
    290                 295                 300

Met Pro Arg Lys Leu Phe Ile Asp Ile Phe Pro Gly Asn Glu Thr Asn
305                 310                 315                 320

Leu Asp Trp Ile Glu Tyr Gln Ile Lys Ala Glu Gln Ser Tyr Ser Glu
                325                 330                 335

Ala Leu Gln Ser Leu Ala Pro Glu Val Thr Arg Ala Gln Lys Lys Leu
            340                 345                 350

Ile Ser Leu Glu Gln Glu Ser Asn Phe Asp Val Thr Ala Ile Lys Glu
        355                 360                 365

Val Asn Arg Asn Ile Ser Ile Gly Glu Ala Lys Ala His Arg Ala Lys
    370                 375                 380

Lys Glu Met Val Glu Ala Asn Leu Arg Leu Val Ile Ser Ile Ala Lys
385                 390                 395                 400

Lys Tyr Thr Asn Arg Gly Leu Gln Phe Leu Asp Leu Ile Gln Glu Gly
                405                 410                 415

Asn Ile Gly Leu Met Lys Ala Val Asp Lys Phe Glu Tyr Arg Arg Gly
            420                 425                 430

Tyr Lys Phe Ser Thr Tyr Ala Thr Trp Trp Ile Arg Gln Ala Ile Thr
        435                 440                 445

Arg Ser Ile Ala Asp Gln Ala Arg Thr Ile Arg Ile Pro Val His Met
    450                 455                 460

Ile Glu Thr Ile Asn Lys Leu Asn Arg Val Ser Arg Gln Met Ile Gln
465                 470                 475                 480

Glu Leu Gly Arg Glu Ala Thr Pro Glu Glu Leu Ser Glu Arg Met Glu
                485                 490                 495

Met Pro Glu His Lys Ile Arg Lys Ile Leu Lys Ile Ala Lys Glu Pro
            500                 505                 510

Ile Ser Met Glu Thr Pro Ile Gly Asp Asp Glu Asp Ser His Leu Gly
        515                 520                 525

Asp Phe Ile Glu Asp Thr Thr Met Gln Leu Pro Val Asp Ser Thr Met
    530                 535                 540

Gly Asp Ala Leu Lys Gln Ala Thr Ser Asp Ile Leu Glu Asn Leu Thr
545                 550                 555                 560

Pro Arg Glu Ala Lys Val Leu Arg Met Arg Phe Gly Ile Asp Met Asn
                565                 570                 575

Thr Asp His Thr Leu Glu Glu Val Gly Lys Gln Phe Asp Val Thr Arg
            580                 585                 590

Glu Arg Ile Arg Gln Ile Glu Ala Lys Ala Leu Arg Lys Leu Arg His
        595                 600                 605

Pro Thr Arg Ser Glu Ile Leu Lys Ser Phe Leu Asp Ser Glu Glu
    610                 615                 620
```

<210> SEQ ID NO 16

<211> LENGTH: 623
<212> TYPE: PRT
<213> ORGANISM: Piscirickettsia salmonis

<400> SEQUENCE: 16

```
Met Asp Gln Gln Glu Lys Arg Ser Gln Phe Lys Glu Leu Ile Val Arg
1               5                   10                  15

Gly Lys Gln Gln Gly Phe Leu Thr Phe Thr Glu Val Asn Asp His Leu
            20                  25                  30

Pro Asp Asp Met Ser Ser Pro Glu Glu Val Glu Glu Ile Val Ala Met
        35                  40                  45

Ile Ser Asp Met Gly Ile Pro Val Tyr Glu Thr Ala Pro Asp Pro Asp
    50                  55                  60

Ser Leu Leu Met Asn Glu His Ala Ser Ser Ala Glu Asp Asp Ala Asp
65                  70                  75                  80

Asp Ala Val Ala Ala Leu Asp Ser Asp Ala Glu Phe Gly Arg Thr Thr
                85                  90                  95

Asp Pro Val Arg Met Tyr Met Arg Glu Met Gly Ser Val Glu Leu Leu
            100                 105                 110

Thr Arg Gln Gly Glu Ile Glu Leu Ala Lys Arg Ile Glu Glu Gly Val
        115                 120                 125

Lys Gln Ala Phe Glu Ala Ile Ala His Tyr Pro Gln Ser Thr Ala Ile
    130                 135                 140

Ile Leu Glu Glu Tyr Ala Arg Phe Glu Ala Glu Glu Ile Arg Leu Asp
145                 150                 155                 160

Asp Ile Ile Ser Gly Tyr Ile Thr Glu Glu Asp Glu Ala Pro Thr Ser
                165                 170                 175

Asn Ile Gly Ser Met Leu Asp Asp Ala Asn Lys Ala Asp Asp Asn Phe
            180                 185                 190

Glu Ala Ala Leu Thr Glu Asp Asp Ser Thr Asp Asp Gly Glu Gly Glu
        195                 200                 205

Asp Asp Asn Glu Glu Ile Pro Val Asp Asn Thr Leu Asp Val Glu Glu
    210                 215                 220

Ala Ala Glu Arg Phe Ala Glu Leu Lys Ala Ala Tyr Asp Ala Val Ile
225                 230                 235                 240

Gln Val Gln Glu Lys His Gly Ile His His Lys Lys Thr Gln Gln Arg
                245                 250                 255

Cys Glu Glu Leu Ser Lys Val Leu Met Thr Phe Arg Leu Lys Pro Asn
            260                 265                 270

Met Ile Asp Lys Ile Thr Asn Tyr Leu His Gly Leu Leu Ser Gln Val
        275                 280                 285

Arg Lys His Glu Arg His Ile Met Ala Leu Cys Ile Asn Gln Ala Lys
    290                 295                 300

Met Pro Arg Lys Leu Phe Ile Asp Ile Phe Pro Gly Asn Glu Thr Asn
305                 310                 315                 320

Leu Glu Trp Ile Glu Tyr Gln Ile Lys Ala Glu Gln Ser Tyr Ser Glu
                325                 330                 335

Ala Leu Gln Ser Leu Ala Pro Glu Val Thr Arg Ala Gln Lys Lys Leu
            340                 345                 350

Ile Ser Leu Glu Gln Glu Ser Asn Phe Asp Val Thr Ala Ile Lys Glu
        355                 360                 365

Val Asn Arg Asn Ile Ser Ile Gly Glu Ala Lys Ala His Arg Ala Lys
    370                 375                 380

Lys Glu Met Val Glu Ala Asn Leu Arg Leu Val Ile Ser Ile Ala Lys
```

```
385                 390                 395                 400

Lys Tyr Thr Asn Arg Gly Leu Gln Phe Leu Asp Leu Ile Gln Glu Gly
                405                 410                 415

Asn Ile Gly Leu Met Lys Ala Val Asp Lys Phe Glu Tyr Arg Arg Gly
            420                 425                 430

Tyr Lys Phe Ser Thr Tyr Ala Thr Trp Trp Ile Arg Gln Ala Ile Thr
        435                 440                 445

Arg Ser Ile Ala Asp Gln Ala Arg Thr Ile Arg Ile Pro Val His Met
    450                 455                 460

Ile Glu Thr Ile Asn Lys Leu Asn Arg Val Ser Arg Gln Met Ile Gln
465                 470                 475                 480

Glu Leu Gly Arg Glu Ala Thr Pro Glu Glu Leu Ser Glu Arg Met Glu
                485                 490                 495

Met Pro Glu His Lys Ile Arg Lys Ile Leu Lys Ile Ala Lys Glu Pro
            500                 505                 510

Ile Ser Met Glu Thr Pro Ile Gly Asp Asp Glu Asp Ser His Leu Gly
        515                 520                 525

Asp Phe Ile Glu Asp Thr Thr Met Gln Leu Pro Val Asp Ser Thr Met
    530                 535                 540

Gly Asp Ala Leu Lys Gln Ala Thr Ser Asp Ile Leu Glu Asn Leu Thr
545                 550                 555                 560

Pro Arg Glu Ala Lys Val Leu Arg Met Arg Phe Gly Ile Asp Met Asn
                565                 570                 575

Thr Asp His Thr Leu Glu Glu Val Gly Lys Gln Phe Asp Val Thr Arg
            580                 585                 590

Glu Arg Ile Arg Gln Ile Glu Ala Lys Ala Leu Arg Lys Leu Arg His
        595                 600                 605

Pro Thr Arg Ser Glu Ile Leu Lys Ser Phe Leu Asp Ser Glu Glu
    610                 615                 620


<210> SEQ ID NO 17
<211> LENGTH: 623
<212> TYPE: PRT
<213> ORGANISM: Piscirickettsia salmonis

<400> SEQUENCE: 17

Met Asp Gln Gln Glu Lys Arg Ser Gln Phe Lys Glu Leu Ile Val Arg
1               5                   10                  15

Gly Lys Gln Gln Gly Phe Leu Thr Phe Thr Glu Val Asn Asp His Leu
            20                  25                  30

Pro Asp Asp Met Ser Ser Pro Glu Glu Val Glu Glu Ile Val Ala Met
        35                  40                  45

Ile Ser Asp Met Gly Ile Pro Val Tyr Glu Thr Ala Pro Asp Pro Asp
    50                  55                  60

Ser Leu Leu Met Asn Glu His Ala Ser Ser Ala Glu Asp Asp Ala Asp
65                  70                  75                  80

Asp Ala Val Ala Ala Leu Asp Ser Asp Ala Glu Phe Gly Arg Thr Thr
                85                  90                  95

Asp Pro Val Arg Met Tyr Met Arg Glu Met Gly Ser Val Glu Leu Leu
            100                 105                 110

Thr Arg Gln Gly Glu Ile Glu Leu Ala Lys Arg Ile Glu Glu Gly Val
        115                 120                 125

Lys Gln Ala Phe Glu Ala Ile Ala His Tyr Pro Gln Ser Thr Ala Ile
    130                 135                 140
```

Ile Leu Glu Glu Tyr Ala Arg Phe Glu Ala Glu Glu Ile Arg Leu Asp
145 150 155 160

Asp Ile Ile Ser Gly Tyr Ile Thr Glu Glu Asp Glu Ala Pro Thr Ser
165 170 175

Asn Ile Gly Ser Met Leu Asp Asp Ala Asn Lys Ala Asp Asp Asn Phe
180 185 190

Glu Ala Ala Leu Thr Glu Asp Asp Ser Thr Asp Asp Gly Glu Gly Glu
195 200 205

Asp Asp Asn Glu Glu Ile Pro Val Asp Asn Thr Leu Asp Val Glu Glu
210 215 220

Ala Ala Glu Arg Phe Ala Glu Leu Lys Ala Ala Tyr Asp Ala Val Ile
225 230 235 240

Gln Val Gln Glu Lys His Gly Ile His His Lys Lys Thr Gln Gln Arg
245 250 255

Cys Glu Glu Leu Ser Lys Val Leu Met Thr Phe Arg Leu Lys Pro Asn
260 265 270

Met Ile Asp Lys Ile Thr Asn Tyr Leu His Gly Leu Leu Ser Gln Val
275 280 285

Arg Lys His Glu Arg His Ile Met Ala Leu Cys Ile Asn Gln Ala Lys
290 295 300

Met Pro Arg Lys Leu Phe Ile Asp Ile Phe Pro Gly Asn Glu Thr Asn
305 310 315 320

Leu Glu Trp Ile Glu Tyr Gln Ile Lys Ala Glu Gln Ser Tyr Ser Glu
325 330 335

Ala Leu Gln Ser Leu Ala Pro Glu Val Thr Arg Ala Gln Lys Lys Leu
340 345 350

Ile Ser Leu Glu Gln Glu Ser Asn Phe Asp Val Thr Ala Ile Lys Glu
355 360 365

Val Asn Arg Asn Ile Ser Ile Gly Glu Ala Lys Ala His Arg Ala Lys
370 375 380

Lys Glu Met Val Glu Ala Asn Leu Arg Leu Val Ile Ser Ile Ala Lys
385 390 395 400

Lys Tyr Thr Asn Arg Gly Leu Gln Phe Leu Asp Leu Ile Gln Glu Gly
405 410 415

Asn Ile Gly Leu Met Lys Ala Val Asp Lys Phe Glu Tyr Arg Arg Gly
420 425 430

Tyr Lys Phe Ser Thr Tyr Ala Thr Trp Trp Ile Arg Gln Ala Ile Thr
435 440 445

Arg Ser Ile Ala Asp Gln Ala Arg Thr Ile Arg Ile Pro Val His Met
450 455 460

Ile Glu Thr Ile Asn Lys Leu Asn Arg Val Ser Arg Gln Met Ile Gln
465 470 475 480

Glu Leu Gly Arg Glu Ala Thr Pro Glu Glu Leu Ser Glu Arg Met Glu
485 490 495

Met Pro Glu His Lys Ile Arg Lys Ile Leu Lys Ile Ala Lys Glu Pro
500 505 510

Ile Ser Met Glu Thr Pro Ile Gly Asp Asp Glu Asp Ser His Leu Gly
515 520 525

Asp Phe Ile Glu Asp Thr Thr Met Gln Leu Pro Val Asp Ser Thr Met
530 535 540

Gly Asp Ala Leu Lys Gln Ala Thr Ser Asp Ile Leu Glu Asn Leu Thr
545 550 555 560

Pro Arg Glu Ala Lys Val Leu Arg Met Arg Phe Gly Ile Asp Met Asn

```
                565                 570                 575

Thr Asp His Thr Leu Glu Glu Val Gly Lys Gln Phe Asp Val Thr Arg
            580                 585                 590

Glu Arg Ile Arg Gln Ile Glu Ala Lys Ala Leu Arg Lys Leu Arg His
        595                 600                 605

Pro Thr Arg Ser Glu Ile Leu Lys Ser Phe Leu Asp Ser Glu Glu
    610                 615                 620


<210> SEQ ID NO 18
<211> LENGTH: 43
<212> TYPE: PRT
<213> ORGANISM: Piscirickettsia salmonis

<400> SEQUENCE: 18

Val His Met Ile Glu Thr Ile Asn Lys Leu Asn Arg Val Ser Arg Gln
1               5                   10                  15

Met Ile Gln Glu Leu Gly Arg Glu Ala Thr Pro Glu Glu Leu Ser Glu
            20                  25                  30

Arg Met Glu Met Pro Glu His Lys Ile Arg Lys
        35                  40


<210> SEQ ID NO 19
<211> LENGTH: 43
<212> TYPE: PRT
<213> ORGANISM: Piscirickettsia salmonis

<400> SEQUENCE: 19

Val His Met Ile Glu Thr Ile Asn Lys Leu Asn Arg Val Ser Arg Gln
1               5                   10                  15

Met Ile Gln Glu Leu Gly Arg Glu Ala Thr Pro Glu Glu Leu Ser Glu
            20                  25                  30

Arg Met Glu Met Pro Glu His Lys Ile Arg Lys
        35                  40


<210> SEQ ID NO 20
<211> LENGTH: 43
<212> TYPE: PRT
<213> ORGANISM: Piscirickettsia salmonis

<400> SEQUENCE: 20

Val His Met Ile Glu Thr Ile Asn Lys Leu Asn Arg Val Ser Arg Gln
1               5                   10                  15

Met Ile Gln Glu Leu Gly Arg Glu Ala Thr Pro Glu Glu Leu Ser Glu
            20                  25                  30

Arg Met Glu Met Pro Glu His Lys Ile Arg Lys
        35                  40


<210> SEQ ID NO 21
<211> LENGTH: 43
<212> TYPE: PRT
<213> ORGANISM: Piscirickettsia salmonis

<400> SEQUENCE: 21

Val His Met Ile Glu Thr Ile Asn Lys Leu Asn Arg Val Ser Arg Gln
1               5                   10                  15

Met Ile Gln Glu Leu Gly Arg Glu Ala Thr Pro Glu Glu Leu Ser Glu
            20                  25                  30

Arg Met Glu Met Pro Glu His Lys Ile Arg Lys
        35                  40
```

<210> SEQ ID NO 22
<211> LENGTH: 43
<212> TYPE: PRT
<213> ORGANISM: Piscirickettsia salmonis

<400> SEQUENCE: 22

```
Val His Met Ile Glu Thr Ile Asn Lys Leu Asn Arg Val Ser Arg Gln
1               5                   10                  15

Met Ile Gln Glu Leu Gly Arg Glu Ala Thr Pro Glu Glu Leu Ser Glu
            20                  25                  30

Arg Met Glu Met Pro Glu His Lys Ile Arg Lys
        35                  40
```

<210> SEQ ID NO 23
<211> LENGTH: 43
<212> TYPE: PRT
<213> ORGANISM: Piscirickettsia salmonis

<400> SEQUENCE: 23

```
Val His Met Ile Glu Thr Ile Asn Lys Leu Asn Arg Val Ser Arg Gln
1               5                   10                  15

Met Ile Gln Glu Leu Gly Arg Glu Ala Thr Pro Glu Glu Leu Ser Glu
            20                  25                  30

Arg Met Glu Met Pro Glu His Lys Ile Arg Lys
        35                  40
```

<210> SEQ ID NO 24
<211> LENGTH: 43
<212> TYPE: PRT
<213> ORGANISM: Piscirickettsia salmonis

<400> SEQUENCE: 24

```
Val His Met Ile Glu Thr Ile Asn Lys Leu Asn Arg Val Ser Arg Gln
1               5                   10                  15

Met Ile Gln Glu Leu Gly Arg Glu Ala Thr Pro Glu Glu Leu Ser Glu
            20                  25                  30

Arg Met Glu Met Pro Glu His Lys Ile Arg Lys
        35                  40
```

<210> SEQ ID NO 25
<211> LENGTH: 82
<212> TYPE: PRT
<213> ORGANISM: Piscirickettsia salmonis

<400> SEQUENCE: 25

```
Met Lys Ile Asn His Gln Pro Gly Gly Ile Met Leu Ile Met Asn Asn
1               5                   10                  15

His Gly Glu Val Met Thr Ser Tyr Ser His Met Met Ile Phe Phe Ser
            20                  25                  30

Asn Tyr Gly Glu Lys Val Lys Ile Glu Asn Gln Arg Ile Leu Asn Asp
        35                  40                  45

Asn Lys Leu Leu Phe Ser Asn Arg Val Ser Arg Val Arg Tyr Arg Pro
    50                  55                  60

Cys Leu Ile Ile Asp Ala Lys Asp Ala Leu Ser Val Cys Ser Gly Val
65                  70                  75                  80

Phe His
```

<210> SEQ ID NO 26
<211> LENGTH: 218

<212> TYPE: PRT
<213> ORGANISM: Piscirickettsia salmonis

<400> SEQUENCE: 26

```
Met Lys Ile Asn His Gln Pro Gly Gly Ile Met Leu Ile Met Asn Asn
1               5                   10                  15

His Gly Glu Val Met Thr Ser Tyr Ser His Met Met Ser Phe Phe Ser
            20                  25                  30

Asn Tyr Gly Glu Lys Val Lys Ile Glu Asn Gln Arg Ile Leu Asn Asp
        35                  40                  45

Asn Lys Leu Leu Phe Ser Asn Arg Val Ser Arg Val Arg Tyr Arg Pro
    50                  55                  60

Cys Leu Ile Ile Asp Ala Lys Asp Ala Leu Ser Val Cys Ser Gly Val
65                  70                  75                  80

Phe His Gln Val Lys Asn Glu Phe Gly Val Val Val Ala Ser Ser Leu
                85                  90                  95

Asn Val Met Ile Tyr Asp Tyr Lys Ser Met Ser Asp Glu Asp Ile Ile
            100                 105                 110

His Ile Leu Lys Ser Val Lys Lys His Pro Lys Leu Ser Leu Ile Glu
        115                 120                 125

Ser Lys Ile Leu Phe Leu Lys Val Val Met Lys Gly Ile Lys Cys Arg
    130                 135                 140

His Ile Glu Ser Leu Leu Lys Val Ser Gly Ser Thr Val Tyr Thr Tyr
145                 150                 155                 160

Cys Met Asn Ile Lys Ser Lys Ala Asn Ile Phe Ser Phe Lys Gly Gln
                165                 170                 175

Ser Val Ile Gln Glu Leu Glu Lys Ser Gln Phe Phe Ser Asp Ile Ser
            180                 185                 190

Ile Lys Ile Asn Ile Asp Phe Tyr Asn Ile Asn Asn Gly Val Asn Glu
        195                 200                 205

Lys Asn Val Cys Gln Val Tyr Ser Leu Ala
    210                 215
```

<210> SEQ ID NO 27
<211> LENGTH: 218
<212> TYPE: PRT
<213> ORGANISM: Piscirickettsia salmonis

<400> SEQUENCE: 27

```
Met Lys Ile Asn His Gln Pro Gly Gly Ile Met Leu Ile Met Asn Asn
1               5                   10                  15

His Gly Glu Val Met Thr Ser Tyr Ser His Met Met Ser Phe Phe Ser
            20                  25                  30

Asn Tyr Gly Glu Lys Val Lys Ile Glu Asn Gln Arg Ile Leu Asn Asp
        35                  40                  45

Asn Lys Leu Leu Phe Ser Asn Arg Val Ser Arg Val Arg Tyr Arg Pro
    50                  55                  60

Cys Leu Ile Ile Asp Ala Lys Asp Ala Leu Ser Val Cys Ser Gly Val
65                  70                  75                  80

Phe His Gln Val Lys Asn Glu Phe Gly Val Val Val Ala Ser Ser Leu
                85                  90                  95

Asn Val Met Ile Tyr Asp Tyr Lys Ser Met Ser Asp Glu Asp Ile Ile
            100                 105                 110

His Ile Leu Lys Ser Val Lys Lys His Pro Lys Leu Ser Leu Ile Glu
        115                 120                 125
```

-continued

```
Ser Lys Ile Leu Phe Leu Lys Val Val Met Lys Gly Ile Lys Cys Arg
    130                 135                 140

His Ile Glu Ser Leu Leu Lys Val Ser Gly Ser Thr Val Tyr Thr Tyr
145                 150                 155                 160

Cys Met Asn Ile Lys Ser Lys Ala Asn Ile Phe Ser Phe Lys Gly Gln
                165                 170                 175

Ser Val Ile Gln Glu Leu Glu Lys Ser Gln Phe Phe Ser Asp Ile Ser
            180                 185                 190

Ile Lys Ile Asn Ile Asp Phe Tyr Asn Ile Asn Asn Gly Val Asn Glu
        195                 200                 205

Lys Asn Val Cys Gln Val Tyr Ser Leu Ala
    210                 215


<210> SEQ ID NO 28
<211> LENGTH: 218
<212> TYPE: PRT
<213> ORGANISM: Piscirickettsia salmonis

<400> SEQUENCE: 28

Met Lys Ile Asn His Gln Pro Gly Gly Ile Met Leu Ile Met Asn Asn
1               5                   10                  15

His Gly Glu Val Met Thr Ser Tyr Ser His Met Met Ser Phe Phe Ser
            20                  25                  30

Asn Tyr Gly Glu Lys Val Lys Ile Glu Asn Gln Arg Ile Leu Asn Asp
        35                  40                  45

Asn Lys Leu Leu Phe Ser Asn Arg Val Ser Glu Val Arg Tyr Arg Pro
    50                  55                  60

Cys Leu Ile Ile Asp Ala Lys Asp Ala Phe Ser Val Cys Ser Gly Val
65                  70                  75                  80

Phe His Gln Val Lys Asn Glu Phe Gly Val Val Val Ala Asn Ser Leu
                85                  90                  95

Asn Val Met Ile Tyr Asp Tyr Lys Ser Met Ser Asp Glu Asp Ile Ile
            100                 105                 110

His Ile Leu Lys Ser Val Lys Lys His Pro Lys Leu Ser Leu Ile Glu
        115                 120                 125

Ser Lys Ile Leu Phe Leu Lys Val Val Met Lys Gly Ile Lys Cys Arg
    130                 135                 140

His Ile Glu Ser Leu Leu Lys Val Ser Gly Ser Thr Val Tyr Thr Tyr
145                 150                 155                 160

Cys Met Asn Ile Lys Ser Lys Ala Asn Ile Phe Ser Phe Lys Gly Gln
                165                 170                 175

Ser Val Ile Gln Glu Leu Glu Lys Ser Gln Phe Phe Ser Asp Ile Ala
            180                 185                 190

Met Lys Ile Asn Ile Asp Phe Tyr Ser Ile Asn Asn Glu Ala Asn Glu
        195                 200                 205

Lys Asn Val Cys Gln Val Tyr Ser Leu Ala
    210                 215


<210> SEQ ID NO 29
<211> LENGTH: 218
<212> TYPE: PRT
<213> ORGANISM: Piscirickettsia salmonis

<400> SEQUENCE: 29

Met Lys Ile Asn His Gln Pro Gly Gly Ile Met Leu Ile Met Asn Asn
1               5                   10                  15
```

```
His Gly Glu Val Met Thr Ser Tyr Ser His Met Met Ile Phe Phe Ser
            20                  25                  30

Asn Tyr Gly Glu Lys Val Lys Ile Glu Asn Gln Arg Ile Leu Asn Asp
        35                  40                  45

Asn Lys Leu Leu Phe Ser Asn Arg Val Ser Arg Val Arg Tyr Arg Pro
    50                  55                  60

Cys Leu Ile Ile Asp Ala Lys Asp Ala Leu Ser Val Cys Ser Gly Val
65                  70                  75                  80

Phe His Gln Val Lys Asn Glu Phe Gly Val Val Val Ala Ser Ser Leu
                85                  90                  95

Asn Val Met Ile Tyr Asp Tyr Lys Ser Met Ser Asp Glu Asp Ile Ile
            100                 105                 110

His Ile Leu Lys Ser Val Lys Lys His Pro Lys Leu Ser Leu Ile Glu
        115                 120                 125

Ser Lys Ile Leu Phe Leu Lys Val Val Met Lys Gly Ile Lys Cys Arg
    130                 135                 140

His Ile Glu Ser Leu Leu Lys Val Ser Gly Ser Thr Val Tyr Thr Tyr
145                 150                 155                 160

Cys Met Asn Ile Lys Ser Lys Ala Asn Ile Phe Ser Phe Lys Gly Gln
                165                 170                 175

Ser Val Ile Gln Glu Leu Glu Lys Ser Gln Phe Phe Ser Asp Ile Ser
            180                 185                 190

Ile Lys Ile Asn Ile Asp Phe Tyr Asn Ile Asn Asn Gly Val Asn Glu
        195                 200                 205

Lys Asn Val Cys Gln Val Tyr Ser Leu Ala
    210                 215


<210> SEQ ID NO 30
<211> LENGTH: 99
<212> TYPE: PRT
<213> ORGANISM: Piscirickettsia salmonis

<400> SEQUENCE: 30

Lys Ile Glu Asn Gln Arg Ile Leu Asn Asp Asn Lys Leu Leu Phe Ser
1               5                   10                  15

Asn Arg Val Ser Arg Val Arg Tyr Arg Pro Cys Leu Ile Ile Asp Ala
            20                  25                  30

Lys Asp Ala Leu Ser Val Cys Ser Gly Val Phe His Gln Val Lys Asn
        35                  40                  45

Glu Phe Gly Val Val Val Ala Ser Ser Leu Asn Val Met Ile Tyr Asp
    50                  55                  60

Tyr Lys Ser Met Ser Asp Glu Asp Ile Ile His Ile Leu Lys Ser Val
65                  70                  75                  80

Lys Lys His Pro Lys Leu Ser Leu Ile Glu Ser Lys Ile Leu Phe Leu
                85                  90                  95

Lys Val Val


<210> SEQ ID NO 31
<211> LENGTH: 99
<212> TYPE: PRT
<213> ORGANISM: Piscirickettsia salmonis

<400> SEQUENCE: 31

Lys Ile Glu Asn Gln Arg Ile Leu Asn Asp Asn Lys Leu Leu Phe Ser
1               5                   10                  15

Asn Arg Val Ser Arg Val Arg Tyr Arg Pro Cys Leu Ile Ile Asp Ala
```

```
            20                  25                  30

Lys Asp Ala Leu Ser Val Cys Ser Gly Val Phe His Gln Val Lys Asn
        35                  40                  45

Glu Phe Gly Val Val Val Ala Ser Ser Leu Asn Val Met Ile Tyr Asp
    50                  55                  60

Tyr Lys Ser Met Ser Asp Glu Asp Ile Ile His Ile Leu Lys Ser Val
65                  70                  75                  80

Lys Lys His Pro Lys Leu Ser Leu Ile Glu Ser Lys Ile Leu Phe Leu
                85                  90                  95

Lys Val Val


<210> SEQ ID NO 32
<211> LENGTH: 99
<212> TYPE: PRT
<213> ORGANISM: Piscirickettsia salmonis

<400> SEQUENCE: 32

Lys Ile Glu Asn Gln Arg Ile Leu Asn Asp Asn Lys Leu Leu Phe Ser
1               5                   10                  15

Asn Arg Val Ser Arg Val Arg Tyr Arg Pro Cys Leu Ile Ile Asp Ala
            20                  25                  30

Lys Asp Ala Leu Ser Val Cys Ser Gly Val Phe His Gln Val Lys Asn
        35                  40                  45

Glu Phe Gly Val Val Val Ala Ser Ser Leu Asn Val Met Ile Tyr Asp
    50                  55                  60

Tyr Lys Ser Met Ser Asp Glu Asp Ile Ile His Ile Leu Lys Ser Val
65                  70                  75                  80

Lys Lys His Pro Lys Leu Ser Leu Ile Glu Ser Lys Ile Leu Phe Leu
                85                  90                  95

Lys Val Val


<210> SEQ ID NO 33
<211> LENGTH: 99
<212> TYPE: PRT
<213> ORGANISM: Piscirickettsia salmonis

<400> SEQUENCE: 33

Lys Ile Glu Asn Gln Arg Ile Leu Asn Asp Asn Lys Leu Leu Phe Ser
1               5                   10                  15

Asn Arg Val Ser Arg Val Arg Tyr Arg Pro Cys Leu Ile Ile Asp Ala
            20                  25                  30

Lys Asp Ala Leu Ser Val Cys Ser Gly Val Phe His Gln Val Lys Asn
        35                  40                  45

Glu Phe Gly Val Val Val Ala Ser Ser Leu Asn Val Met Ile Tyr Asp
    50                  55                  60

Tyr Lys Ser Met Ser Asp Glu Asp Ile Ile His Ile Leu Lys Ser Val
65                  70                  75                  80

Lys Lys His Pro Lys Leu Ser Leu Ile Glu Ser Lys Ile Leu Phe Leu
                85                  90                  95

Lys Val Val


<210> SEQ ID NO 34
<211> LENGTH: 99
<212> TYPE: PRT
<213> ORGANISM: Piscirickettsia salmonis

<400> SEQUENCE: 34
```

Lys Ile Glu Asn Gln Arg Ile Leu Asn Asp Asn Lys Leu Leu Phe Ser
1 5 10 15

Asn Arg Val Ser Glu Val Arg Tyr Arg Pro Cys Leu Ile Ile Asp Ala
20 25 30

Lys Asp Ala Phe Ser Val Cys Ser Gly Val Phe His Gln Val Lys Asn
35 40 45

Glu Phe Gly Val Val Val Ala Asn Ser Leu Asn Val Met Ile Tyr Asp
50 55 60

Tyr Lys Ser Met Ser Asp Glu Asp Ile Ile His Ile Leu Lys Ser Val
65 70 75 80

Lys Lys His Pro Lys Leu Ser Leu Ile Glu Ser Lys Ile Leu Phe Leu
85 90 95

Lys Val Val

<210> SEQ ID NO 35
<211> LENGTH: 99
<212> TYPE: PRT
<213> ORGANISM: Piscirickettsia salmonis

<400> SEQUENCE: 35

Lys Ile Glu Asn Gln Arg Ile Leu Asn Asp Asn Lys Leu Leu Phe Ser
1 5 10 15

Asn Arg Val Ser Glu Val Arg Tyr Arg Pro Cys Leu Ile Ile Asp Ala
20 25 30

Lys Asp Ala Phe Ser Val Cys Ser Gly Val Phe His Gln Val Lys Asn
35 40 45

Glu Phe Gly Val Val Val Ala Asn Ser Leu Asn Val Met Ile Tyr Asp
50 55 60

Tyr Lys Ser Met Ser Asp Glu Asp Ile Ile His Ile Leu Lys Ser Val
65 70 75 80

Lys Lys His Pro Lys Leu Ser Leu Ile Glu Ser Lys Ile Leu Phe Leu
85 90 95

Lys Val Val

<210> SEQ ID NO 36
<211> LENGTH: 99
<212> TYPE: PRT
<213> ORGANISM: Piscirickettsia salmonis

<400> SEQUENCE: 36

Lys Ile Glu Asn Gln Arg Ile Leu Asn Asp Asn Lys Leu Leu Phe Ser
1 5 10 15

Asn Arg Val Ser Glu Val Arg Tyr Arg Pro Cys Leu Ile Ile Asp Ala
20 25 30

Lys Asp Ala Phe Ser Val Cys Ser Gly Val Phe His Gln Val Lys Asn
35 40 45

Glu Phe Gly Val Val Val Ala Asn Ser Leu Asn Val Met Ile Tyr Asp
50 55 60

Tyr Lys Ser Met Ser Asp Glu Asp Ile Ile His Ile Leu Lys Ser Val
65 70 75 80

Lys Lys His Pro Lys Leu Ser Leu Ile Glu Ser Lys Ile Leu Phe Leu
85 90 95

Lys Val Val

<210> SEQ ID NO 37

<211> LENGTH: 99
<212> TYPE: PRT
<213> ORGANISM: Piscirickettsia salmonis

<400> SEQUENCE: 37

Lys Ile Glu Asn Gln Arg Ile Leu Asn Asp Asn Lys Leu Leu Phe Ser
1               5                   10                  15

Asn Arg Val Ser Glu Val Arg Tyr Arg Pro Cys Leu Ile Ile Asp Ala
            20                  25                  30

Lys Asp Ala Phe Ser Val Cys Ser Gly Val Phe His Gln Val Lys Asn
        35                  40                  45

Glu Phe Gly Val Val Val Ala Asn Ser Leu Asn Val Met Ile Tyr Asp
    50                  55                  60

Tyr Lys Ser Met Ser Asp Glu Asp Ile Ile His Ile Leu Lys Ser Val
65                  70                  75                  80

Lys Lys His Pro Lys Leu Ser Leu Ile Glu Ser Lys Ile Leu Phe Leu
                85                  90                  95

Lys Val Val

<210> SEQ ID NO 38
<211> LENGTH: 99
<212> TYPE: PRT
<213> ORGANISM: Piscirickettsia salmonis

<400> SEQUENCE: 38

Lys Ile Glu Asn Gln Arg Ile Leu Asn Asp Asn Lys Leu Leu Phe Ser
1               5                   10                  15

Asn Arg Val Ser Glu Val Arg Tyr Arg Pro Cys Leu Ile Ile Asp Ala
            20                  25                  30

Lys Asp Ala Phe Ser Val Cys Ser Gly Val Phe His Gln Val Lys Asn
        35                  40                  45

Glu Phe Gly Val Val Val Ala Asn Ser Leu Asn Val Met Ile Tyr Asp
    50                  55                  60

Tyr Lys Ser Met Ser Asp Glu Asp Ile Ile His Ile Leu Lys Ser Val
65                  70                  75                  80

Lys Lys His Pro Lys Leu Ser Leu Ile Glu Ser Lys Ile Leu Phe Leu
                85                  90                  95

Lys Val Val

<210> SEQ ID NO 39
<211> LENGTH: 316
<212> TYPE: PRT
<213> ORGANISM: Piscirickettsia salmonis

<400> SEQUENCE: 39

Met Ile Ser Leu Trp Lys Thr Tyr Gln Ala Leu Lys Thr Lys Gly Ile
1               5                   10                  15

Leu Gly Ile Asn Gln Arg Asn Ala Asp Phe Ile Ile Arg Tyr Asn Gln
            20                  25                  30

Arg Lys Tyr Tyr Pro Leu Val Asp Asp Lys Ile Met Thr Lys Thr Leu
        35                  40                  45

Ala Ile Lys Asp Gly Ile Ala Val Pro Lys Leu Tyr Ala Thr Leu Lys
    50                  55                  60

Thr Asp His Asp Thr His His Leu Glu Gln Ile Leu Ala Asn Arg Thr
65                  70                  75                  80

Asp Phe Val Ile Lys Pro Ala Arg Gly Ala Gly Gly Asp Gly Ile Leu
                85                  90                  95

-continued

```
Val Ile Thr Asn Arg His Gly Glu Arg Phe Arg Lys Val Ser Gly Ala
            100                 105                 110

Leu Leu His Leu Asp Asp Ile Arg His His Ile Ser Asn Ile Leu Ser
        115                 120                 125

Gly Val Tyr Ser Leu Gly Gly Gln Arg Asp Gln Ala Met Ile Glu Tyr
    130                 135                 140

Arg Val Gln Phe Asp Pro Leu Phe Lys Lys Ile Ser Tyr Gln Gly Val
145                 150                 155                 160

Pro Asp Ile Arg Ile Ile Val Leu Lys Gly Tyr Pro Ala Met Ala Met
                165                 170                 175

Val Arg Leu Pro Thr Arg Leu Pro Asp Gly Lys Ala Asn Leu His Gln
            180                 185                 190

Gly Ala Ile Gly Val Gly Ile Asp Leu Thr Thr Gly Ile Thr Leu Glu
        195                 200                 205

Gly Val Trp Met Asn Asp Pro Ile His Glu His Pro Asp Thr Gly Tyr
    210                 215                 220

Ala Val Pro Gly Leu Gln Ile Pro His Trp Asp His Phe Leu Asn Leu
225                 230                 235                 240

Ala Ala Arg Cys Tyr Glu Leu Thr Gln Leu Gly Tyr Leu Gly Val Asp
                245                 250                 255

Ile Ile Leu Asp Lys Asp Lys Gly Pro Leu Met Leu Glu Leu Asn Ala
            260                 265                 270

Arg Pro Gly Leu Asn Ile Gln Ile Ala Asn Asn Ser Gly Leu Leu His
        275                 280                 285

Arg Leu Arg Phe Ile Glu Gln Gln Asn Gln Gln Arg Thr Ala Asp Glu
    290                 295                 300

Arg Ile Ala Phe Ile Lys His Gln Phe Ala Lys Ile
305                 310                 315


<210> SEQ ID NO 40
<211> LENGTH: 316
<212> TYPE: PRT
<213> ORGANISM: Piscirickettsia salmonis

<400> SEQUENCE: 40

Met Ile Ser Leu Trp Lys Thr Tyr Gln Ala Leu Lys Thr Lys Gly Ile
1               5                   10                  15

Leu Gly Ile Asn Gln Arg Asn Ala Asp Phe Ile Ile Arg Tyr Asn Gln
            20                  25                  30

Arg Lys Tyr Tyr Pro Leu Val Asp Asp Lys Ile Met Thr Lys Thr Leu
        35                  40                  45

Ala Ile Lys Asp Gly Ile Ala Val Pro Lys Leu Tyr Ala Thr Leu Lys
    50                  55                  60

Thr Asp His Asp Thr His His Leu Glu Gln Ile Leu Ala Asn Arg Thr
65                  70                  75                  80

Asp Phe Val Ile Lys Pro Ala Arg Gly Ala Gly Gly Asp Gly Ile Leu
                85                  90                  95

Val Ile Thr Asn Arg His Gly Glu Arg Phe Arg Lys Val Ser Gly Ala
            100                 105                 110

Leu Leu His Leu Asp Asp Ile Arg His His Ile Ser Asn Ile Leu Ser
        115                 120                 125

Gly Val Tyr Ser Leu Gly Gly Gln Arg Asp Gln Ala Met Ile Glu Tyr
    130                 135                 140

Arg Val Gln Phe Asp Pro Leu Phe Lys Lys Ile Ser Tyr Gln Gly Val
```

-continued

```
145                 150                 155                 160

Pro Asp Ile Arg Ile Ile Val Leu Lys Gly Tyr Pro Ala Met Ala Met
                165                 170                 175

Val Arg Leu Pro Thr Arg Leu Ser Asp Gly Lys Ala Asn Leu His Gln
            180                 185                 190

Gly Ala Ile Gly Val Gly Ile Asp Leu Thr Thr Gly Ile Thr Leu Glu
        195                 200                 205

Gly Val Trp Met Asn Asp Pro Ile His Glu His Pro Asp Thr Gly Tyr
    210                 215                 220

Ala Val Pro Gly Leu Gln Ile Pro His Trp Asp His Phe Leu Asn Leu
225                 230                 235                 240

Ala Ala Arg Cys Tyr Glu Leu Thr Gln Leu Gly Tyr Leu Gly Val Asp
                245                 250                 255

Ile Ile Leu Asp Lys Asp Lys Gly Pro Leu Met Leu Glu Leu Asn Ala
            260                 265                 270

Arg Pro Gly Leu Asn Ile Gln Ile Ala Asn Asn Ser Gly Leu Leu His
        275                 280                 285

Arg Leu Arg Phe Ile Glu Gln Gln Asn Gln Gln Arg Thr Ala Asp Glu
    290                 295                 300

Arg Ile Ala Phe Ile Lys His Gln Phe Ala Lys Ile
305                 310                 315


<210> SEQ ID NO 41
<211> LENGTH: 316
<212> TYPE: PRT
<213> ORGANISM: Piscirickettsia salmonis

<400> SEQUENCE: 41

Met Ile Ser Leu Trp Lys Thr Tyr Gln Ala Leu Lys Thr Lys Gly Ile
1               5                   10                  15

Leu Gly Ile Asn Gln Arg Asn Ala Asp Phe Ile Ile Arg Tyr Asn Gln
            20                  25                  30

Arg Lys Tyr Tyr Pro Leu Val Asp Asp Lys Ile Met Thr Lys Thr Leu
        35                  40                  45

Ala Ile Lys Asp Gly Ile Ala Val Pro Lys Leu Tyr Ala Thr Leu Lys
    50                  55                  60

Thr Asp His Asp Thr His His Leu Glu Gln Ile Leu Ala Asn Arg Thr
65                  70                  75                  80

Asp Phe Val Ile Lys Pro Ala Arg Gly Ala Gly Gly Asp Gly Ile Leu
                85                  90                  95

Val Ile Thr Asn Arg His Gly Glu Arg Phe Arg Lys Val Ser Gly Ala
            100                 105                 110

Leu Leu His Leu Asp Asp Ile Arg His His Ile Ser Asn Ile Leu Ser
        115                 120                 125

Gly Val Tyr Ser Leu Gly Gly Gln Arg Asp Gln Ala Met Ile Glu Tyr
    130                 135                 140

Arg Val Gln Phe Asp Pro Leu Phe Lys Lys Ile Ser Tyr Gln Gly Val
145                 150                 155                 160

Pro Asp Ile Arg Ile Ile Val Leu Lys Gly Tyr Pro Ala Met Ala Met
                165                 170                 175

Val Arg Leu Pro Thr Arg Leu Ser Asp Gly Lys Ala Asn Leu His Gln
            180                 185                 190

Gly Ala Ile Gly Val Gly Ile Asp Leu Thr Thr Gly Ile Thr Leu Glu
        195                 200                 205
```

Gly Val Trp Met Asn Asp Pro Ile His Glu His Pro Asp Thr Gly Tyr
    210                 215                 220

Ala Val Pro Gly Leu Gln Ile Pro His Trp Asp His Phe Leu Asn Leu
225                 230                 235                 240

Ala Ala Arg Cys Tyr Glu Leu Thr Gln Leu Gly Tyr Leu Gly Val Asp
                245                 250                 255

Ile Ile Leu Asp Lys Asp Lys Gly Pro Leu Met Leu Glu Leu Asn Ala
            260                 265                 270

Arg Pro Gly Leu Asn Ile Gln Ile Ala Asn Asn Ser Gly Leu Leu His
        275                 280                 285

Arg Leu Arg Phe Ile Glu Gln Gln Asn Gln Gln Arg Thr Ala Asp Glu
    290                 295                 300

Arg Ile Ala Phe Ile Lys His Gln Phe Ala Lys Ile
305                 310                 315

<210> SEQ ID NO 42
<211> LENGTH: 316
<212> TYPE: PRT
<213> ORGANISM: Piscirickettsia salmonis

<400> SEQUENCE: 42

Met Ile Ser Leu Trp Lys Thr Tyr Gln Ala Leu Lys Thr Lys Gly Ile
1               5                   10                  15

Leu Gly Ile Asn Gln Arg Asn Ala Asp Phe Ile Ile Arg Tyr Asn Gln
            20                  25                  30

Arg Lys Tyr Tyr Pro Leu Val Asp Asp Lys Ile Met Thr Lys Thr Leu
        35                  40                  45

Ala Ile Lys Asp Gly Ile Ala Val Pro Lys Leu Tyr Ala Thr Leu Lys
    50                  55                  60

Thr Asp His Asp Thr His His Leu Glu Gln Ile Leu Ala Asn Arg Thr
65                  70                  75                  80

Asp Phe Val Ile Lys Pro Ala Arg Gly Ala Gly Gly Asp Gly Ile Leu
                85                  90                  95

Val Ile Thr Asn Arg His Gly Glu Arg Phe Arg Lys Val Ser Gly Ala
            100                 105                 110

Leu Leu His Leu Asp Asp Ile Arg His His Ile Ser Asn Ile Leu Ser
        115                 120                 125

Gly Val Tyr Ser Leu Gly Gly Gln Arg Asp Gln Ala Met Ile Glu Tyr
    130                 135                 140

Arg Val Gln Phe Asp Pro Leu Phe Lys Lys Ile Ser Tyr Gln Gly Val
145                 150                 155                 160

Pro Asp Ile Arg Ile Ile Val Leu Lys Gly Tyr Pro Ala Met Ala Met
                165                 170                 175

Val Arg Leu Pro Thr Arg Leu Ser Asp Gly Lys Ala Asn Leu His Gln
            180                 185                 190

Gly Ala Ile Gly Val Gly Ile Asp Leu Thr Thr Gly Ile Thr Leu Glu
        195                 200                 205

Gly Val Trp Met Asn Asp Pro Ile His Glu His Pro Asp Thr Gly Tyr
    210                 215                 220

Ala Val Pro Gly Leu Gln Ile Pro His Trp Asp His Phe Leu Asn Leu
225                 230                 235                 240

Ala Ala Arg Cys Tyr Glu Leu Thr Gln Leu Gly Tyr Leu Gly Val Asp
                245                 250                 255

Ile Ile Leu Asp Lys Asp Lys Gly Pro Leu Met Leu Glu Leu Asn Ala
            260                 265                 270

-continued

```
Arg Pro Gly Leu Asn Ile Gln Ile Ala Asn Asn Ser Gly Leu Leu His
        275                 280                 285

Arg Leu Arg Phe Ile Glu Gln Gln Asn Gln Gln Arg Thr Ala Asp Glu
    290                 295                 300

Arg Ile Ala Phe Ile Lys His Gln Phe Ala Lys Ile
305                 310                 315


<210> SEQ ID NO 43
<211> LENGTH: 316
<212> TYPE: PRT
<213> ORGANISM: Piscirickettsia salmonis

<400> SEQUENCE: 43

Met Ile Ser Leu Trp Lys Thr Tyr Gln Ala Leu Lys Thr Lys Gly Ile
1               5                   10                  15

Leu Gly Ile Asn Gln Arg Asn Ala Asp Phe Ile Ile Arg Tyr Asn Gln
            20                  25                  30

Arg Lys Tyr Tyr Pro Leu Val Asp Asp Lys Ile Met Thr Lys Thr Leu
        35                  40                  45

Ala Ile Lys Asp Gly Ile Ala Val Pro Lys Leu Tyr Ala Thr Leu Lys
    50                  55                  60

Thr Asp His Asp Thr His His Leu Glu Gln Ile Leu Ala Asn Arg Thr
65                  70                  75                  80

Asp Phe Val Ile Lys Pro Ala Arg Gly Ala Gly Gly Asp Gly Ile Leu
                85                  90                  95

Val Ile Thr Asn Arg His Gly Glu Arg Phe Arg Lys Val Ser Gly Ala
            100                 105                 110

Leu Leu His Leu Asp Asp Ile Arg His His Ile Ser Asn Ile Leu Ser
        115                 120                 125

Gly Val Tyr Ser Leu Gly Gly Gln Arg Asp Gln Ala Met Ile Glu Tyr
    130                 135                 140

Arg Val Gln Phe Asp Pro Leu Phe Lys Lys Ile Ser Tyr Gln Gly Val
145                 150                 155                 160

Pro Asp Ile Arg Ile Ile Val Leu Lys Gly Tyr Pro Ala Met Ala Met
                165                 170                 175

Val Arg Leu Pro Thr Arg Leu Ser Asp Gly Lys Ala Asn Leu His Gln
            180                 185                 190

Gly Ala Ile Gly Val Gly Ile Asp Leu Thr Thr Gly Ile Thr Leu Glu
        195                 200                 205

Gly Val Trp Met Asn Asp Pro Ile His Glu His Pro Asp Thr Gly Tyr
    210                 215                 220

Ala Val Pro Gly Leu Gln Ile Pro His Trp Asp His Phe Leu Asn Leu
225                 230                 235                 240

Ala Ala Arg Cys Tyr Glu Leu Thr Gln Leu Gly Tyr Leu Gly Val Asp
                245                 250                 255

Ile Ile Leu Asp Lys Asp Lys Gly Pro Leu Met Leu Glu Leu Asn Ala
            260                 265                 270

Arg Pro Gly Leu Asn Ile Gln Ile Ala Asn Asn Ser Gly Leu Leu His
        275                 280                 285

Arg Leu Arg Phe Ile Glu Gln Gln Asn Gln Gln Arg Thr Ala Asp Glu
    290                 295                 300

Arg Ile Ala Phe Ile Lys His Gln Phe Ala Lys Ile
305                 310                 315
```

<210> SEQ ID NO 44
<211> LENGTH: 134
<212> TYPE: PRT
<213> ORGANISM: Piscirickettsia salmonis

<400> SEQUENCE: 44

```
Asp Ile Arg His His Ile Ser Asn Ile Leu Ser Gly Val Tyr Ser Leu
1               5                   10                  15

Gly Gly Gln Arg Asp Gln Ala Met Ile Glu Tyr Arg Val Gln Phe Asp
            20                  25                  30

Pro Leu Phe Lys Lys Ile Ser Tyr Gln Gly Val Pro Asp Ile Arg Ile
        35                  40                  45

Ile Val Leu Lys Gly Tyr Pro Ala Met Ala Met Val Arg Leu Pro Thr
    50                  55                  60

Arg Leu Ser Asp Gly Lys Ala Asn Leu His Gln Gly Ala Ile Gly Val
65                  70                  75                  80

Gly Ile Asp Leu Thr Thr Gly Ile Thr Leu Glu Gly Val Trp Met Asn
                85                  90                  95

Asp Pro Ile His Glu His Pro Asp Thr Gly Tyr Ala Val Pro Gly Leu
            100                 105                 110

Gln Ile Pro His Trp Asp His Phe Leu Asn Leu Ala Ala Arg Cys Tyr
        115                 120                 125

Glu Leu Thr Gln Leu Gly
    130
```

<210> SEQ ID NO 45
<211> LENGTH: 134
<212> TYPE: PRT
<213> ORGANISM: Piscirickettsia salmonis

<400> SEQUENCE: 45

```
Asp Ile Arg His His Ile Ser Asn Ile Leu Ser Gly Val Tyr Ser Leu
1               5                   10                  15

Gly Gly Gln Arg Asp Gln Ala Met Ile Glu Tyr Arg Val Gln Phe Asp
            20                  25                  30

Pro Leu Phe Lys Lys Ile Ser Tyr Gln Gly Val Pro Asp Ile Arg Ile
        35                  40                  45

Ile Val Leu Lys Gly Tyr Pro Ala Met Ala Met Val Arg Leu Pro Thr
    50                  55                  60

Arg Leu Ser Asp Gly Lys Ala Asn Leu His Gln Gly Ala Ile Gly Val
65                  70                  75                  80

Gly Ile Asp Leu Thr Thr Gly Ile Thr Leu Glu Gly Val Trp Met Asn
                85                  90                  95

Asp Pro Ile His Glu His Pro Asp Thr Gly Tyr Ala Val Pro Gly Leu
            100                 105                 110

Gln Ile Pro His Trp Asp His Phe Leu Asn Leu Ala Ala Arg Cys Tyr
        115                 120                 125

Glu Leu Thr Gln Leu Gly
    130
```

<210> SEQ ID NO 46
<211> LENGTH: 134
<212> TYPE: PRT
<213> ORGANISM: Piscirickettsia salmonis

<400> SEQUENCE: 46

```
Asp Ile Arg His His Ile Ser Asn Ile Leu Ser Gly Val Tyr Ser Leu
1               5                   10                  15
```

```
Gly Gly Gln Arg Asp Gln Ala Met Ile Glu Tyr Arg Val Gln Phe Asp
            20                  25                  30

Pro Leu Phe Lys Lys Ile Ser Tyr Gln Gly Val Pro Asp Ile Arg Ile
        35                  40                  45

Ile Val Leu Lys Gly Tyr Pro Ala Met Ala Met Val Arg Leu Pro Thr
    50                  55                  60

Arg Leu Ser Asp Gly Lys Ala Asn Leu His Gln Gly Ala Ile Gly Val
65                  70                  75                  80

Gly Ile Asp Leu Thr Thr Gly Ile Thr Leu Glu Gly Val Trp Met Asn
                85                  90                  95

Asp Pro Ile His Glu His Pro Asp Thr Gly Tyr Ala Val Pro Gly Leu
            100                 105                 110

Gln Ile Pro His Trp Asp His Phe Leu Asn Leu Ala Ala Arg Cys Tyr
        115                 120                 125

Glu Leu Thr Gln Leu Gly
    130


<210> SEQ ID NO 47
<211> LENGTH: 134
<212> TYPE: PRT
<213> ORGANISM: Piscirickettsia salmonis

<400> SEQUENCE: 47

Asp Ile Arg His His Ile Ser Asn Ile Leu Ser Gly Val Tyr Ser Leu
1               5                   10                  15

Gly Gly Gln Arg Asp Gln Ala Met Ile Glu Tyr Arg Val Gln Phe Asp
            20                  25                  30

Pro Leu Phe Lys Lys Ile Ser Tyr Gln Gly Val Pro Asp Ile Arg Ile
        35                  40                  45

Ile Val Leu Lys Gly Tyr Pro Ala Met Ala Met Val Arg Leu Pro Thr
    50                  55                  60

Arg Leu Ser Asp Gly Lys Ala Asn Leu His Gln Gly Ala Ile Gly Val
65                  70                  75                  80

Gly Ile Asp Leu Thr Thr Gly Ile Thr Leu Glu Gly Val Trp Met Asn
                85                  90                  95

Asp Pro Ile His Glu His Pro Asp Thr Gly Tyr Ala Val Pro Gly Leu
            100                 105                 110

Gln Ile Pro His Trp Asp His Phe Leu Asn Leu Ala Ala Arg Cys Tyr
        115                 120                 125

Glu Leu Thr Gln Leu Gly
    130


<210> SEQ ID NO 48
<211> LENGTH: 134
<212> TYPE: PRT
<213> ORGANISM: Piscirickettsia salmonis

<400> SEQUENCE: 48

Asp Ile Arg His His Ile Ser Asn Ile Leu Ser Gly Val Tyr Ser Leu
1               5                   10                  15

Gly Gly Gln Arg Asp Gln Ala Met Ile Glu Tyr Arg Val Gln Phe Asp
            20                  25                  30

Pro Leu Phe Lys Lys Ile Ser Tyr Gln Gly Val Pro Asp Ile Arg Ile
        35                  40                  45

Ile Val Leu Lys Gly Tyr Pro Ala Met Ala Met Val Arg Leu Pro Thr
    50                  55                  60
```

Arg Leu Ser Asp Gly Lys Ala Asn Leu His Gln Gly Ala Ile Gly Val
65 70 75 80

Gly Ile Asp Leu Thr Thr Gly Ile Thr Leu Glu Gly Val Trp Met Asn
85 90 95

Asp Pro Ile His Glu His Pro Asp Thr Gly Tyr Ala Val Pro Gly Leu
100 105 110

Gln Ile Pro His Trp Asp His Phe Leu Asn Leu Ala Ala Arg Cys Tyr
115 120 125

Glu Leu Thr Gln Leu Gly
130

<210> SEQ ID NO 49
<211> LENGTH: 134
<212> TYPE: PRT
<213> ORGANISM: Piscirickettsia salmonis

<400> SEQUENCE: 49

Asp Ile Arg His His Ile Ser Asn Ile Leu Ser Gly Val Tyr Ser Leu
1 5 10 15

Gly Gly Gln Arg Asp Gln Ala Met Ile Glu Tyr Arg Val Gln Phe Asp
20 25 30

Pro Leu Phe Lys Lys Ile Ser Tyr Gln Gly Val Pro Asp Ile Arg Ile
35 40 45

Ile Val Leu Lys Gly Tyr Pro Ala Met Ala Met Val Arg Leu Pro Thr
50 55 60

Arg Leu Ser Asp Gly Lys Ala Asn Leu His Gln Gly Ala Ile Gly Val
65 70 75 80

Gly Ile Asp Leu Thr Thr Gly Ile Thr Leu Glu Gly Val Trp Met Asn
85 90 95

Asp Pro Ile His Glu His Pro Asp Thr Gly Tyr Ala Val Pro Gly Leu
100 105 110

Gln Ile Pro His Trp Asp His Phe Leu Asn Leu Ala Ala Arg Cys Tyr
115 120 125

Glu Leu Thr Gln Leu Gly
130

<210> SEQ ID NO 50
<211> LENGTH: 134
<212> TYPE: PRT
<213> ORGANISM: Piscirickettsia salmonis

<400> SEQUENCE: 50

Asp Ile Arg His His Ile Ser Asn Ile Leu Ser Gly Val Tyr Ser Leu
1 5 10 15

Gly Gly Gln Arg Asp Gln Ala Met Ile Glu Tyr Arg Val Gln Phe Asp
20 25 30

Pro Leu Phe Lys Lys Ile Ser Tyr Gln Gly Val Pro Asp Ile Arg Ile
35 40 45

Ile Val Leu Lys Gly Tyr Pro Ala Met Ala Met Val Arg Leu Pro Thr
50 55 60

Arg Leu Ser Asp Gly Lys Ala Asn Leu His Gln Gly Ala Ile Gly Val
65 70 75 80

Gly Ile Asp Leu Thr Thr Gly Ile Thr Leu Glu Gly Val Trp Met Asn
85 90 95

Asp Pro Ile His Glu His Pro Asp Thr Gly Tyr Ala Val Pro Gly Leu
100 105 110

```
Gln Ile Pro His Trp Asp His Phe Leu Asn Leu Ala Ala Arg Cys Tyr
        115                 120                 125

Glu Leu Thr Gln Leu Gly
    130


<210> SEQ ID NO 51
<211> LENGTH: 134
<212> TYPE: PRT
<213> ORGANISM: Piscirickettsia salmonis

<400> SEQUENCE: 51

Asp Ile Arg His His Ile Ser Asn Ile Leu Ser Gly Val Tyr Ser Leu
1               5                   10                  15

Gly Gly Gln Arg Asp Gln Ala Met Ile Glu Tyr Arg Val Gln Phe Asp
            20                  25                  30

Pro Leu Phe Lys Lys Ile Ser Tyr Gln Gly Val Pro Asp Ile Arg Ile
        35                  40                  45

Ile Val Leu Lys Gly Tyr Pro Ala Met Ala Met Val Arg Leu Pro Thr
    50                  55                  60

Arg Leu Ser Asp Gly Lys Ala Asn Leu His Gln Gly Ala Ile Gly Val
65                  70                  75                  80

Gly Ile Asp Leu Thr Thr Gly Ile Thr Leu Glu Gly Val Trp Met Asn
                85                  90                  95

Asp Pro Ile His Glu His Pro Asp Thr Gly Tyr Ala Val Pro Gly Leu
            100                 105                 110

Gln Ile Pro His Trp Asp His Phe Leu Asn Leu Ala Ala Arg Cys Tyr
        115                 120                 125

Glu Leu Thr Gln Leu Gly
    130


<210> SEQ ID NO 52
<211> LENGTH: 134
<212> TYPE: PRT
<213> ORGANISM: Piscirickettsia salmonis

<400> SEQUENCE: 52

Asp Ile Arg His His Ile Ser Asn Ile Leu Ser Gly Val Tyr Ser Leu
1               5                   10                  15

Gly Gly Gln Arg Asp Gln Ala Met Ile Glu Tyr Arg Val Gln Phe Asp
            20                  25                  30

Pro Leu Phe Lys Lys Ile Ser Tyr Gln Gly Val Pro Asp Ile Arg Ile
        35                  40                  45

Ile Val Leu Lys Gly Tyr Pro Ala Met Ala Met Val Arg Leu Pro Thr
    50                  55                  60

Arg Leu Ser Asp Gly Lys Ala Asn Leu His Gln Gly Ala Ile Gly Val
65                  70                  75                  80

Gly Ile Asp Leu Thr Thr Gly Ile Thr Leu Glu Gly Val Trp Met Asn
                85                  90                  95

Asp Pro Ile His Glu His Pro Asp Thr Gly Tyr Ala Val Pro Gly Leu
            100                 105                 110

Gln Ile Pro His Trp Asp His Phe Leu Asn Leu Ala Ala Arg Cys Tyr
        115                 120                 125

Glu Leu Thr Gln Leu Gly
    130


<210> SEQ ID NO 53
```

<211> LENGTH: 660
<212> TYPE: PRT
<213> ORGANISM: Piscirickettsia salmonis

<400> SEQUENCE: 53

```
Met Ile Lys Asn Ile Met Leu Trp Leu Val Ile Ala Leu Val Leu Val
1               5                   10                  15

Thr Val Phe Ser Asn Leu Gly Pro Arg Gln Gln Ser Val Asn Arg Leu
            20                  25                  30

Asp Tyr Ser Thr Phe Val Lys Asp Ile Asn Asn Gly Gln Val Lys Ser
        35                  40                  45

Val Ile Ile Asp Gly Leu Asn Ile Lys Gly Gln Thr Ser Ser Gly Thr
    50                  55                  60

Pro Phe Ala Thr Tyr Ile Pro Trp Lys Asp Pro Phe Leu Met Asp Gln
65                  70                  75                  80

Met Leu Ala Lys Asn Val Thr Ile Ala Ala Lys Pro Pro Glu Gln Arg
                85                  90                  95

Ser Trp Leu Leu Ser Ala Leu Ile Ser Trp Phe Pro Gly Ile Leu Leu
            100                 105                 110

Ile Ala Ile Trp Ile Phe Phe Leu Arg Gln Met Gln Gly Gly Gly Gly
        115                 120                 125

Gly Lys Gly Met Met Ser Phe Gly Ser Ser Lys Ala Arg Leu Leu Gly
    130                 135                 140

Glu Asp Gln Ile Lys Val Asn Phe Ala Asp Val Ala Gly Cys Glu Glu
145                 150                 155                 160

Ala Lys Glu Glu Val Lys Glu Leu Val Asp Phe Leu Arg Asp Pro Thr
                165                 170                 175

Lys Phe Gln Lys Leu Gly Gly Lys Ile Pro Gln Gly Val Leu Ile Val
            180                 185                 190

Gly Pro Pro Gly Thr Gly Lys Thr Leu Leu Ala Lys Ala Ile Ala Gly
        195                 200                 205

Glu Ala Lys Val Pro Phe Phe Ser Ile Ser Gly Ser Asp Phe Val Glu
    210                 215                 220

Met Phe Val Gly Val Gly Ala Ser Arg Val Arg Asp Met Phe Asp Gln
225                 230                 235                 240

Ala Lys Lys Arg Ala Pro Cys Ile Ile Phe Ile Asp Glu Ile Asp Ala
                245                 250                 255

Val Gly Arg His Arg Gly Ser Gly Met Gly Gly Gly His Asp Glu Arg
            260                 265                 270

Glu Gln Thr Leu Asn Gln Met Leu Val Glu Met Asp Gly Phe Glu Gly
        275                 280                 285

Thr Glu Gly Val Ile Val Ile Ala Ala Thr Asn Arg Pro Asp Val Leu
    290                 295                 300

Asp Pro Ala Leu Leu Arg Pro Gly Arg Phe Asp Arg Gln Val Ser Val
305                 310                 315                 320

Gly Leu Pro Asp Val Lys Gly Arg Glu Gln Ile Leu Lys Val His Met
                325                 330                 335

Arg Lys Val Pro Leu Gly Asp Asp Val Lys Ala Ser Leu Ile Ala Arg
            340                 345                 350

Gly Thr Pro Gly Phe Ser Gly Ala Asp Leu Ala Asn Leu Val Asn Glu
        355                 360                 365

Ala Ala Leu Phe Ala Ala Arg Lys Asp Lys Thr Val Val Ala Met Arg
    370                 375                 380

Glu Phe Asp Asp Ala Lys Asp Lys Ile Leu Met Gly Thr Glu Arg Arg
```

385 390 395 400

Ser Met Ala Met Thr Glu Glu Gln Lys Arg Leu Thr Ala Phe His Glu
405 410 415

Ala Gly His Ala Ile Val Gly Cys Leu Val Pro Asp His Asp Pro Val
420 425 430

Tyr Lys Val Ser Ile Val Pro Arg Gly Arg Ala Leu Gly Val Thr Met
435 440 445

Tyr Leu Pro Glu Glu Asp Ser Tyr Gly Tyr Ser Arg Glu Arg Leu Glu
450 455 460

Ser Leu Ile Ser Ser Met Tyr Gly Gly Arg Ile Ala Glu Ala Leu Val
465 470 475 480

Phe Gly Val Glu Lys Val Thr Thr Gly Ala Ser Asn Asp Ile Glu Lys
485 490 495

Ala Ser Glu Val Ala Arg Asn Met Val Thr Lys Trp Gly Leu Ser Glu
500 505 510

Arg Leu Gly Pro Ile Leu Tyr Gly Gln Glu Gly Gly Asp Pro Phe Gly
515 520 525

Tyr Gly Ala Gly Lys Gly Thr Pro Glu Phe Ser Asp Gln Thr Ser Val
530 535 540

Ala Ile Asp Glu Glu Val Arg Gln Ile Ile Asp Arg Asn Tyr Thr Arg
545 550 555 560

Ala Glu Ser Ile Leu Ile Asn Asn Arg Asp Ile Leu Asp Ala Met Ala
565 570 575

Asp Ala Leu Met Val Tyr Glu Thr Ile Asp Arg Asp Gln Val Ala Asp
580 585 590

Leu Met Ala Arg Arg Pro Val Lys Ala Pro Lys Asp Trp Asp Gln Pro
595 600 605

Ser Asp Glu Ser Gly Ser Ser Ala Ser Gly Asp Glu Leu Gln Pro Leu
610 615 620

Asp Ala Asn Ile Asn Thr Asp Ile Asn Glu Thr Lys Ser Ala Asp Gln
625 630 635 640

Glu Thr Asp Gln Gly Ala Pro Ser Pro Glu Ile Lys Gly Lys Pro Ala
645 650 655

Asp Asp Pro Thr
660

<210> SEQ ID NO 54
<211> LENGTH: 660
<212> TYPE: PRT
<213> ORGANISM: Piscirickettsia salmonis

<400> SEQUENCE: 54

Met Ile Lys Asn Ile Met Leu Trp Leu Val Ile Ala Leu Val Leu Val
1 5 10 15

Thr Val Phe Ser Asn Leu Gly Pro Arg Gln Gln Ser Val Asn Arg Leu
20 25 30

Asp Tyr Ser Thr Phe Val Lys Asp Ile Asn Asn Gly Gln Val Lys Ser
35 40 45

Val Ile Ile Asp Gly Leu Asn Ile Lys Gly Gln Thr Ser Ser Gly Thr
50 55 60

Pro Phe Ala Thr Tyr Ile Pro Trp Lys Asp Pro Phe Leu Met Asp Gln
65 70 75 80

Met Leu Ala Lys Asn Val Thr Ile Ala Ala Lys Pro Pro Glu Gln Arg
85 90 95

-continued

```
Ser Trp Leu Leu Ser Ala Leu Ile Ser Trp Phe Pro Gly Ile Leu Leu
            100                 105                 110

Ile Ala Ile Trp Ile Phe Phe Leu Arg Gln Met Gln Gly Gly Gly Gly
        115                 120                 125

Gly Lys Gly Met Met Ser Phe Gly Ser Ser Lys Ala Arg Leu Leu Gly
    130                 135                 140

Glu Asp Gln Ile Lys Val Asn Phe Ala Asp Val Ala Gly Cys Glu Glu
145                 150                 155                 160

Ala Lys Glu Glu Val Lys Glu Leu Val Asp Phe Leu Arg Asp Pro Thr
                165                 170                 175

Lys Phe Gln Lys Leu Gly Gly Lys Ile Pro Gln Gly Val Leu Met Val
            180                 185                 190

Gly Pro Pro Gly Thr Gly Lys Thr Leu Leu Ala Lys Ala Ile Ala Gly
        195                 200                 205

Glu Ala Lys Val Pro Phe Phe Ser Ile Ser Gly Ser Asp Phe Val Glu
    210                 215                 220

Met Phe Val Gly Val Gly Ala Ser Arg Val Arg Asp Met Phe Asp Gln
225                 230                 235                 240

Ala Lys Lys Arg Ala Pro Cys Ile Ile Phe Ile Asp Glu Ile Asp Ala
                245                 250                 255

Val Gly Arg His Arg Gly Ser Gly Met Gly Gly Gly His Asp Glu Arg
            260                 265                 270

Glu Gln Thr Leu Asn Gln Met Leu Val Glu Met Asp Gly Phe Glu Gly
        275                 280                 285

Thr Glu Gly Val Ile Val Ile Ala Ala Thr Asn Arg Pro Asp Val Leu
    290                 295                 300

Asp Pro Ala Leu Leu Arg Pro Gly Arg Phe Asp Arg Gln Val Ser Val
305                 310                 315                 320

Gly Leu Pro Asp Val Lys Gly Arg Glu Gln Ile Leu Lys Val His Met
                325                 330                 335

Arg Lys Val Pro Leu Gly Asp Asp Val Lys Ala Ser Leu Ile Ala Arg
            340                 345                 350

Gly Thr Pro Gly Phe Ser Gly Ala Asp Leu Ala Asn Leu Val Asn Glu
        355                 360                 365

Ala Ala Leu Phe Ala Ala Arg Lys Asp Lys Thr Val Val Ala Met Arg
    370                 375                 380

Glu Phe Asp Asp Ala Lys Asp Lys Ile Leu Met Gly Thr Glu Arg Arg
385                 390                 395                 400

Ser Met Ala Met Thr Glu Glu Gln Lys Arg Leu Thr Ala Phe His Glu
                405                 410                 415

Ala Gly His Ala Ile Val Gly Cys Leu Val Pro Asp His Asp Pro Val
            420                 425                 430

Tyr Lys Val Ser Ile Val Pro Arg Gly Arg Ala Leu Gly Val Thr Met
        435                 440                 445

Tyr Leu Pro Glu Glu Asp Ser Tyr Gly Tyr Ser Arg Glu Arg Leu Glu
    450                 455                 460

Ser Leu Ile Ser Ser Met Tyr Gly Gly Arg Ile Ala Glu Ala Leu Val
465                 470                 475                 480

Phe Gly Val Glu Lys Val Thr Thr Gly Ala Ser Asn Asp Ile Glu Lys
                485                 490                 495

Ala Ser Glu Val Ala Arg Asn Met Val Thr Lys Trp Gly Leu Ser Glu
            500                 505                 510

Arg Leu Gly Pro Ile Leu Tyr Gly Gln Glu Gly Gly Asp Pro Phe Gly
```

-continued

```
        515                 520                 525

Tyr Gly Ala Gly Lys Gly Thr Pro Glu Phe Ser Asp Gln Thr Ser Val
    530                 535                 540

Ala Ile Asp Glu Glu Val Arg Gln Ile Ile Asp Arg Asn Tyr Thr Arg
545                 550                 555                 560

Ala Glu Ser Ile Leu Ile Asn Asn Arg Asp Ile Leu Asp Ala Met Ala
                565                 570                 575

Asp Ala Leu Met Val Tyr Glu Thr Ile Asp Arg Asp Gln Val Ala Asp
            580                 585                 590

Leu Met Ala Arg Arg Pro Val Lys Ala Pro Lys Asp Trp Asp Gln Pro
        595                 600                 605

Ser Asp Glu Ser Gly Ser Ser Ala Ser Gly Asp Glu Leu Gln Pro Leu
    610                 615                 620

Asp Ala Asn Ile Asn Thr Asp Ile Asn Glu Thr Lys Ser Ala Asp Gln
625                 630                 635                 640

Glu Thr Asp Gln Gly Ala Pro Ser Pro Glu Ile Lys Gly Lys Pro Ala
                645                 650                 655

Asp Asp Pro Thr
            660


<210> SEQ ID NO 55
<211> LENGTH: 660
<212> TYPE: PRT
<213> ORGANISM: Piscirickettsia salmonis

<400> SEQUENCE: 55

Met Ile Lys Asn Ile Met Leu Trp Leu Val Ile Ala Leu Val Leu Val
1               5                   10                  15

Thr Val Phe Ser Asn Leu Gly Pro Arg Gln Gln Ser Val Asn Arg Leu
            20                  25                  30

Asp Tyr Ser Thr Phe Val Lys Asp Ile Asn Asn Gly Gln Val Lys Ser
        35                  40                  45

Val Ile Ile Asp Gly Leu Asn Ile Lys Gly Gln Thr Ser Ser Gly Thr
    50                  55                  60

Pro Phe Ala Thr Tyr Ile Pro Trp Lys Asp Pro Phe Leu Met Asp Gln
65                  70                  75                  80

Met Leu Ala Lys Asn Val Thr Ile Ala Ala Lys Pro Pro Glu Gln Arg
                85                  90                  95

Ser Trp Leu Leu Ser Ala Leu Ile Ser Trp Phe Pro Gly Ile Leu Leu
            100                 105                 110

Ile Ala Ile Trp Ile Phe Phe Leu Arg Gln Met Gln Gly Gly Gly Gly
        115                 120                 125

Gly Lys Gly Met Met Ser Phe Gly Ser Ser Lys Ala Arg Leu Leu Gly
    130                 135                 140

Glu Asp Gln Ile Lys Val Asn Phe Ala Asp Val Ala Gly Cys Glu Glu
145                 150                 155                 160

Ala Lys Glu Glu Val Lys Glu Leu Val Asp Phe Leu Arg Asp Pro Thr
                165                 170                 175

Lys Phe Gln Lys Leu Gly Gly Lys Ile Pro Gln Gly Val Leu Met Val
            180                 185                 190

Gly Pro Pro Gly Thr Gly Lys Thr Leu Leu Ala Lys Ala Ile Ala Gly
        195                 200                 205

Glu Ala Lys Val Pro Phe Phe Ser Ile Ser Gly Ser Asp Phe Val Glu
    210                 215                 220
```

-continued

```
Met Phe Val Gly Val Gly Ala Ser Arg Val Arg Asp Met Phe Asp Gln
225                 230                 235                 240

Ala Lys Lys Arg Ala Pro Cys Ile Ile Phe Ile Asp Glu Ile Asp Ala
                245                 250                 255

Val Gly Arg His Arg Gly Ser Gly Met Gly Gly Gly His Asp Glu Arg
            260                 265                 270

Glu Gln Thr Leu Asn Gln Met Leu Val Glu Met Asp Gly Phe Glu Gly
        275                 280                 285

Thr Glu Gly Val Ile Val Ile Ala Ala Thr Asn Arg Pro Asp Val Leu
    290                 295                 300

Asp Pro Ala Leu Leu Arg Pro Gly Arg Phe Asp Arg Gln Val Ser Val
305                 310                 315                 320

Gly Leu Pro Asp Val Lys Gly Arg Glu Gln Ile Leu Lys Val His Met
                325                 330                 335

Arg Lys Val Pro Leu Gly Asp Asp Val Lys Ala Ser Leu Ile Ala Arg
            340                 345                 350

Gly Thr Pro Gly Phe Ser Gly Ala Asp Leu Ala Asn Leu Val Asn Glu
        355                 360                 365

Ala Ala Leu Phe Ala Ala Arg Lys Asp Lys Thr Val Val Ala Met Arg
    370                 375                 380

Glu Phe Asp Asp Ala Lys Asp Lys Ile Leu Met Gly Thr Glu Arg Arg
385                 390                 395                 400

Ser Met Ala Met Thr Glu Glu Gln Lys Arg Leu Thr Ala Phe His Glu
                405                 410                 415

Ala Gly His Ala Ile Val Gly Cys Leu Val Pro Asp His Asp Pro Val
            420                 425                 430

Tyr Lys Val Ser Ile Val Pro Arg Gly Arg Ala Leu Gly Val Thr Met
        435                 440                 445

Tyr Leu Pro Glu Glu Asp Ser Tyr Gly Tyr Ser Arg Glu Arg Leu Glu
    450                 455                 460

Ser Leu Ile Ser Ser Met Tyr Gly Gly Arg Ile Ala Glu Ala Leu Val
465                 470                 475                 480

Phe Gly Val Glu Lys Val Thr Thr Gly Ala Ser Asn Asp Ile Glu Lys
                485                 490                 495

Ala Ser Glu Val Ala Arg Asn Met Val Thr Lys Trp Gly Leu Ser Glu
            500                 505                 510

Arg Leu Gly Pro Ile Leu Tyr Gly Gln Glu Gly Gly Asp Pro Phe Gly
        515                 520                 525

Tyr Gly Ala Gly Lys Gly Thr Pro Glu Phe Ser Asp Gln Thr Ser Val
    530                 535                 540

Ala Ile Asp Glu Glu Val Arg Gln Ile Ile Asp Arg Asn Tyr Thr Arg
545                 550                 555                 560

Ala Glu Ser Ile Leu Ile Asn Asn Arg Asp Ile Leu Asp Ala Met Ala
                565                 570                 575

Asp Ala Leu Met Val Tyr Glu Thr Ile Asp Arg Asp Gln Val Ala Asp
            580                 585                 590

Leu Met Ala Arg Arg Pro Val Lys Ala Pro Lys Asp Trp Asp Gln Pro
        595                 600                 605

Ser Asp Glu Ser Gly Ser Ser Ala Ser Gly Asp Glu Leu Gln Pro Leu
    610                 615                 620

Asp Ala Asn Ile Asn Thr Asp Ile Asn Glu Thr Lys Ser Ala Asp Gln
625                 630                 635                 640

Glu Thr Asp Gln Gly Ala Pro Ser Pro Glu Ile Lys Gly Lys Pro Ala
```

```
                645                 650                 655

Asp Asp Pro Thr
            660


<210> SEQ ID NO 56
<211> LENGTH: 660
<212> TYPE: PRT
<213> ORGANISM: Piscirickettsia salmonis

<400> SEQUENCE: 56

Met Ile Lys Asn Ile Met Leu Trp Leu Val Ile Ala Leu Val Leu Val
1               5                   10                  15

Thr Val Phe Ser Asn Leu Gly Pro Arg Gln Gln Ser Val Asn Arg Leu
            20                  25                  30

Asp Tyr Ser Thr Phe Val Lys Asp Ile Asn Asn Gly Gln Val Lys Ser
        35                  40                  45

Val Ile Ile Asp Gly Leu Asn Ile Lys Gly Gln Thr Ser Ser Gly Thr
    50                  55                  60

Pro Phe Ala Thr Tyr Ile Pro Trp Lys Asp Pro Phe Leu Met Asp Gln
65                  70                  75                  80

Met Leu Ser Lys Asn Val Thr Ile Ala Ala Lys Pro Pro Glu Gln Arg
                85                  90                  95

Ser Trp Leu Leu Ser Ala Leu Ile Ser Trp Phe Pro Gly Ile Leu Leu
            100                 105                 110

Ile Ala Ile Trp Ile Phe Phe Leu Arg Gln Met Gln Gly Gly Gly Gly
        115                 120                 125

Gly Lys Gly Met Met Ser Phe Gly Ser Ser Lys Ala Arg Leu Leu Gly
    130                 135                 140

Glu Asp Gln Ile Lys Val Asn Phe Ala Asp Val Ala Gly Cys Glu Glu
145                 150                 155                 160

Ala Lys Glu Glu Val Lys Glu Leu Val Asp Phe Leu Arg Asp Pro Thr
                165                 170                 175

Lys Phe Gln Lys Leu Gly Gly Lys Ile Pro Gln Gly Val Leu Met Val
            180                 185                 190

Gly Pro Pro Gly Thr Gly Lys Thr Leu Leu Ala Lys Ala Ile Ala Gly
        195                 200                 205

Glu Ala Lys Val Pro Phe Phe Ser Ile Ser Gly Ser Asp Phe Val Glu
    210                 215                 220

Met Phe Val Gly Val Gly Ala Ser Arg Val Arg Asp Met Phe Asp Gln
225                 230                 235                 240

Ala Lys Lys Arg Ala Pro Cys Ile Ile Phe Ile Asp Glu Ile Asp Ala
                245                 250                 255

Val Gly Arg His Arg Gly Ser Gly Met Gly Gly Gly His Asp Glu Arg
            260                 265                 270

Glu Gln Thr Leu Asn Gln Met Leu Val Glu Met Asp Gly Phe Glu Gly
        275                 280                 285

Thr Glu Gly Val Ile Val Ile Ala Ala Thr Asn Arg Pro Asp Val Leu
    290                 295                 300

Asp Pro Ala Leu Leu Arg Pro Gly Arg Phe Asp Arg Gln Val Ser Val
305                 310                 315                 320

Gly Leu Pro Asp Val Lys Gly Arg Glu Gln Ile Leu Lys Val His Met
                325                 330                 335

Arg Lys Val Pro Leu Gly Asp Asp Val Lys Ala Ser Leu Ile Ala Arg
            340                 345                 350
```

-continued

```
Gly Thr Pro Gly Phe Ser Gly Ala Asp Leu Ala Asn Leu Val Asn Glu
        355                 360                 365

Ala Ala Leu Phe Ala Ala Arg Lys Asp Lys Thr Val Val Ala Met Arg
    370                 375                 380

Glu Phe Asp Asp Ala Lys Asp Lys Ile Leu Met Gly Thr Glu Arg Arg
385                 390                 395                 400

Ser Met Ala Met Thr Glu Glu Gln Lys Arg Leu Thr Ala Phe His Glu
                405                 410                 415

Ala Gly His Ala Ile Val Gly Cys Leu Val Pro Asp His Asp Pro Val
            420                 425                 430

Tyr Lys Val Ser Ile Val Pro Arg Gly Arg Ala Leu Gly Val Thr Met
        435                 440                 445

Tyr Leu Pro Glu Glu Asp Ser Tyr Gly Tyr Ser Arg Glu Arg Leu Glu
    450                 455                 460

Ser Leu Ile Ser Ser Met Tyr Gly Gly Arg Ile Ala Glu Ala Leu Val
465                 470                 475                 480

Phe Gly Val Glu Lys Val Thr Thr Gly Ala Ser Asn Asp Ile Glu Lys
                485                 490                 495

Ala Ser Glu Val Ala Arg Asn Met Val Thr Lys Trp Gly Leu Ser Glu
            500                 505                 510

Arg Leu Gly Pro Ile Leu Tyr Gly Gln Glu Gly Gly Asp Pro Phe Gly
        515                 520                 525

Tyr Gly Ala Gly Lys Gly Thr Pro Glu Phe Ser Asp Gln Thr Ser Val
    530                 535                 540

Ala Ile Asp Glu Glu Val Arg Gln Ile Ile Asp Arg Asn Tyr Thr Arg
545                 550                 555                 560

Ala Glu Ser Ile Leu Ile Asp Asn Arg Asp Ile Leu Asp Ala Met Ala
                565                 570                 575

Asp Ala Leu Met Val Tyr Glu Thr Ile Asp Arg Glu Gln Val Ala Asp
            580                 585                 590

Leu Met Ala Arg Arg Pro Val Lys Ala Pro Lys Asp Trp Asp Gln Pro
        595                 600                 605

Ser Asp Glu Ser Gly Ser Ser Ala Ser Gly Asp Glu Leu Gln Pro Leu
    610                 615                 620

Asp Ala Asn Ile Asn Thr Asp Ile Asn Asp Thr Lys Ser Ala Asp Gln
625                 630                 635                 640

Glu Ile Asp Gln Gly Ala Pro Ser Pro Glu Ile Lys Gly Lys Pro Ala
                645                 650                 655

Asp Asp Pro Thr
            660
```

<210> SEQ ID NO 57
<211> LENGTH: 660
<212> TYPE: PRT
<213> ORGANISM: Piscirickettsia salmonis

<400> SEQUENCE: 57

```
Met Ile Lys Asn Ile Met Leu Trp Leu Val Ile Ala Leu Val Leu Val
1               5                   10                  15

Thr Val Phe Ser Asn Leu Gly Pro Arg Gln Gln Ser Val Asn Arg Leu
            20                  25                  30

Asp Tyr Ser Thr Phe Val Lys Asp Ile Asn Asn Gly Gln Val Lys Ser
        35                  40                  45

Val Ile Ile Asp Gly Leu Asn Ile Lys Gly Gln Thr Ser Ser Gly Thr
    50                  55                  60
```

-continued

```
Pro Phe Ala Thr Tyr Ile Pro Trp Lys Asp Pro Phe Leu Met Asp Gln
65                  70                  75                  80

Met Leu Ala Lys Asn Val Thr Ile Ala Ala Lys Pro Pro Glu Gln Arg
                85                  90                  95

Ser Trp Leu Leu Ser Ala Leu Ile Ser Trp Phe Pro Gly Ile Leu Leu
            100                 105                 110

Ile Ala Ile Trp Ile Phe Phe Leu Arg Gln Met Gln Gly Gly Gly Gly
        115                 120                 125

Gly Lys Gly Met Met Ser Phe Gly Ser Ser Lys Ala Arg Leu Leu Gly
    130                 135                 140

Glu Asp Gln Ile Lys Val Asn Phe Ala Asp Val Ala Gly Cys Glu Glu
145                 150                 155                 160

Ala Lys Glu Glu Val Lys Glu Leu Val Asp Phe Leu Arg Asp Pro Thr
                165                 170                 175

Lys Phe Gln Lys Leu Gly Gly Lys Ile Pro Gln Gly Val Leu Met Val
            180                 185                 190

Gly Pro Pro Gly Thr Gly Lys Thr Leu Leu Ala Lys Ala Ile Ala Gly
        195                 200                 205

Glu Ala Lys Val Pro Phe Phe Ser Ile Ser Gly Ser Asp Phe Val Glu
    210                 215                 220

Met Phe Val Gly Val Gly Ala Ser Arg Val Arg Asp Met Phe Asp Gln
225                 230                 235                 240

Ala Lys Lys Arg Ala Pro Cys Ile Ile Phe Ile Asp Glu Ile Asp Ala
                245                 250                 255

Val Gly Arg His Arg Gly Ser Gly Met Gly Gly Gly His Asp Glu Arg
            260                 265                 270

Glu Gln Thr Leu Asn Gln Met Leu Val Glu Met Asp Gly Phe Glu Gly
        275                 280                 285

Thr Glu Gly Val Ile Val Ile Ala Ala Thr Asn Arg Pro Asp Val Leu
    290                 295                 300

Asp Pro Ala Leu Leu Arg Pro Gly Arg Phe Asp Arg Gln Val Ser Val
305                 310                 315                 320

Gly Leu Pro Asp Val Lys Gly Arg Glu Gln Ile Leu Lys Val His Met
                325                 330                 335

Arg Lys Val Pro Leu Gly Asp Asp Val Lys Ala Ser Leu Ile Ala Arg
            340                 345                 350

Gly Thr Pro Gly Phe Ser Gly Ala Asp Leu Ala Asn Leu Val Asn Glu
        355                 360                 365

Ala Ala Leu Phe Ala Ala Arg Lys Asp Lys Thr Val Val Ala Met Arg
    370                 375                 380

Glu Phe Asp Asp Ala Lys Asp Lys Ile Leu Met Gly Thr Glu Arg Arg
385                 390                 395                 400

Ser Met Ala Met Thr Glu Glu Gln Lys Arg Leu Thr Ala Phe His Glu
                405                 410                 415

Ala Gly His Ala Ile Val Gly Cys Leu Val Pro Asp His Asp Pro Val
            420                 425                 430

Tyr Lys Val Ser Ile Val Pro Arg Gly Arg Ala Leu Gly Val Thr Met
        435                 440                 445

Tyr Leu Pro Glu Glu Asp Ser Tyr Gly Tyr Ser Arg Glu Arg Leu Glu
    450                 455                 460

Ser Leu Ile Ser Ser Met Tyr Gly Gly Arg Ile Ala Glu Ala Leu Val
465                 470                 475                 480
```

-continued

```
Phe Gly Val Glu Lys Val Thr Thr Gly Ala Ser Asn Asp Ile Glu Lys
                485                 490                 495

Ala Ser Glu Val Ala Arg Asn Met Val Thr Lys Trp Gly Leu Ser Glu
            500                 505                 510

Arg Leu Gly Pro Ile Leu Tyr Gly Gln Glu Gly Gly Asp Pro Phe Gly
        515                 520                 525

Tyr Gly Ala Gly Lys Gly Thr Pro Glu Phe Ser Asp Gln Thr Ser Val
    530                 535                 540

Ala Ile Asp Glu Glu Val Arg Gln Ile Ile Asp Arg Asn Tyr Thr Arg
545                 550                 555                 560

Ala Glu Ser Ile Leu Ile Asn Asn Arg Asp Ile Leu Asp Ala Met Ala
                565                 570                 575

Asp Ala Leu Met Val Tyr Glu Thr Ile Asp Arg Asp Gln Val Ala Asp
            580                 585                 590

Leu Met Ala Arg Arg Pro Val Lys Ala Pro Lys Asp Trp Asp Gln Pro
        595                 600                 605

Ser Asp Glu Ser Gly Ser Ser Ala Ser Gly Asp Glu Leu Gln Pro Leu
    610                 615                 620

Asp Ala Asn Ile Asn Thr Asp Ile Asn Glu Thr Lys Ser Ala Asp Gln
625                 630                 635                 640

Glu Thr Asp Gln Gly Ala Pro Ser Pro Glu Ile Lys Gly Lys Pro Ala
                645                 650                 655

Asp Asp Pro Thr
            660


<210> SEQ ID NO 58
<211> LENGTH: 123
<212> TYPE: PRT
<213> ORGANISM: Piscirickettsia salmonis

<400> SEQUENCE: 58

Phe Ala Asp Val Ala Gly Cys Glu Glu Ala Lys Glu Glu Val Lys Glu
1               5                   10                  15

Leu Val Asp Phe Leu Arg Asp Pro Thr Lys Phe Gln Lys Leu Gly Gly
            20                  25                  30

Lys Ile Pro Gln Gly Val Leu Met Val Gly Pro Pro Gly Thr Gly Lys
        35                  40                  45

Thr Leu Leu Ala Lys Ala Ile Ala Gly Glu Ala Lys Val Pro Phe Phe
    50                  55                  60

Ser Ile Ser Gly Ser Asp Phe Val Glu Met Phe Val Gly Val Gly Ala
65                  70                  75                  80

Ser Arg Val Arg Asp Met Phe Asp Gln Ala Lys Lys Arg Ala Pro Cys
                85                  90                  95

Ile Ile Phe Ile Asp Glu Ile Asp Ala Val Gly Arg His Arg Gly Ser
            100                 105                 110

Gly Met Gly Gly Gly His Asp Glu Arg Glu Gln
        115                 120


<210> SEQ ID NO 59
<211> LENGTH: 123
<212> TYPE: PRT
<213> ORGANISM: Piscirickettsia salmonis

<400> SEQUENCE: 59

Phe Ala Asp Val Ala Gly Cys Glu Glu Ala Lys Glu Glu Val Lys Glu
1               5                   10                  15
```

```
Leu Val Asp Phe Leu Arg Asp Pro Thr Lys Phe Gln Lys Leu Gly Gly
            20                  25                  30

Lys Ile Pro Gln Gly Val Leu Met Val Gly Pro Pro Gly Thr Gly Lys
        35                  40                  45

Thr Leu Leu Ala Lys Ala Ile Ala Gly Glu Ala Lys Val Pro Phe Phe
    50                  55                  60

Ser Ile Ser Gly Ser Asp Phe Val Glu Met Phe Val Gly Val Gly Ala
65                  70                  75                  80

Ser Arg Val Arg Asp Met Phe Asp Gln Ala Lys Lys Arg Ala Pro Cys
                85                  90                  95

Ile Ile Phe Ile Asp Glu Ile Asp Ala Val Gly Arg His Arg Gly Ser
            100                 105                 110

Gly Met Gly Gly Gly His Asp Glu Arg Glu Gln
        115                 120


<210> SEQ ID NO 60
<211> LENGTH: 123
<212> TYPE: PRT
<213> ORGANISM: Piscirickettsia salmonis

<400> SEQUENCE: 60

Phe Ala Asp Val Ala Gly Cys Glu Glu Ala Lys Glu Glu Val Lys Glu
1               5                   10                  15

Leu Val Asp Phe Leu Arg Asp Pro Thr Lys Phe Gln Lys Leu Gly Gly
            20                  25                  30

Lys Ile Pro Gln Gly Val Leu Met Val Gly Pro Pro Gly Thr Gly Lys
        35                  40                  45

Thr Leu Leu Ala Lys Ala Ile Ala Gly Glu Ala Lys Val Pro Phe Phe
    50                  55                  60

Ser Ile Ser Gly Ser Asp Phe Val Glu Met Phe Val Gly Val Gly Ala
65                  70                  75                  80

Ser Arg Val Arg Asp Met Phe Asp Gln Ala Lys Lys Arg Ala Pro Cys
                85                  90                  95

Ile Ile Phe Ile Asp Glu Ile Asp Ala Val Gly Arg His Arg Gly Ser
            100                 105                 110

Gly Met Gly Gly Gly His Asp Glu Arg Glu Gln
        115                 120


<210> SEQ ID NO 61
<211> LENGTH: 123
<212> TYPE: PRT
<213> ORGANISM: Piscirickettsia salmonis

<400> SEQUENCE: 61

Phe Ala Asp Val Ala Gly Cys Glu Glu Ala Lys Glu Glu Val Lys Glu
1               5                   10                  15

Leu Val Asp Phe Leu Arg Asp Pro Thr Lys Phe Gln Lys Leu Gly Gly
            20                  25                  30

Lys Ile Pro Gln Gly Val Leu Met Val Gly Pro Pro Gly Thr Gly Lys
        35                  40                  45

Thr Leu Leu Ala Lys Ala Ile Ala Gly Glu Ala Lys Val Pro Phe Phe
    50                  55                  60

Ser Ile Ser Gly Ser Asp Phe Val Glu Met Phe Val Gly Val Gly Ala
65                  70                  75                  80

Ser Arg Val Arg Asp Met Phe Asp Gln Ala Lys Lys Arg Ala Pro Cys
                85                  90                  95
```

Ile Ile Phe Ile Asp Glu Ile Asp Ala Val Gly Arg His Arg Gly Ser
100 105 110

Gly Met Gly Gly Gly His Asp Glu Arg Glu Gln
115 120

<210> SEQ ID NO 62
<211> LENGTH: 123
<212> TYPE: PRT
<213> ORGANISM: Piscirickettsia salmonis

<400> SEQUENCE: 62

Phe Ala Asp Val Ala Gly Cys Glu Glu Ala Lys Glu Glu Val Lys Glu
1 5 10 15

Leu Val Asp Phe Leu Arg Asp Pro Thr Lys Phe Gln Lys Leu Gly Gly
20 25 30

Lys Ile Pro Gln Gly Val Leu Met Val Gly Pro Pro Gly Thr Gly Lys
35 40 45

Thr Leu Leu Ala Lys Ala Ile Ala Gly Glu Ala Lys Val Pro Phe Phe
50 55 60

Ser Ile Ser Gly Ser Asp Phe Val Glu Met Phe Val Gly Val Gly Ala
65 70 75 80

Ser Arg Val Arg Asp Met Phe Asp Gln Ala Lys Lys Arg Ala Pro Cys
85 90 95

Ile Ile Phe Ile Asp Glu Ile Asp Ala Val Gly Arg His Arg Gly Ser
100 105 110

Gly Met Gly Gly Gly His Asp Glu Arg Glu Gln
115 120

<210> SEQ ID NO 63
<211> LENGTH: 123
<212> TYPE: PRT
<213> ORGANISM: Piscirickettsia salmonis

<400> SEQUENCE: 63

Phe Ala Asp Val Ala Gly Cys Glu Glu Ala Lys Glu Glu Val Lys Glu
1 5 10 15

Leu Val Asp Phe Leu Arg Asp Pro Thr Lys Phe Gln Lys Leu Gly Gly
20 25 30

Lys Ile Pro Gln Gly Val Leu Met Val Gly Pro Pro Gly Thr Gly Lys
35 40 45

Thr Leu Leu Ala Lys Ala Ile Ala Gly Glu Ala Lys Val Pro Phe Phe
50 55 60

Ser Ile Ser Gly Ser Asp Phe Val Glu Met Phe Val Gly Val Gly Ala
65 70 75 80

Ser Arg Val Arg Asp Met Phe Asp Gln Ala Lys Lys Arg Ala Pro Cys
85 90 95

Ile Ile Phe Ile Asp Glu Ile Asp Ala Val Gly Arg His Arg Gly Ser
100 105 110

Gly Met Gly Gly Gly His Asp Glu Arg Glu Gln
115 120

<210> SEQ ID NO 64
<211> LENGTH: 123
<212> TYPE: PRT
<213> ORGANISM: Piscirickettsia salmonis

<400> SEQUENCE: 64

Phe Ala Asp Val Ala Gly Cys Glu Glu Ala Lys Glu Glu Val Lys Glu

-continued

```
1               5                   10                  15

Leu Val Asp Phe Leu Arg Asp Pro Thr Lys Phe Gln Lys Leu Gly Gly
            20                  25                  30

Lys Ile Pro Gln Gly Val Leu Met Val Gly Pro Pro Gly Thr Gly Lys
        35                  40                  45

Thr Leu Leu Ala Lys Ala Ile Ala Gly Glu Ala Lys Val Pro Phe Phe
    50                  55                  60

Ser Ile Ser Gly Ser Asp Phe Val Glu Met Phe Val Gly Val Gly Ala
65                  70                  75                  80

Ser Arg Val Arg Asp Met Phe Asp Gln Ala Lys Lys Arg Ala Pro Cys
            85                  90                  95

Ile Ile Phe Ile Asp Glu Ile Asp Ala Val Gly Arg His Arg Gly Ser
            100                 105                 110

Gly Met Gly Gly Gly His Asp Glu Arg Glu Gln
        115                 120


<210> SEQ ID NO 65
<211> LENGTH: 123
<212> TYPE: PRT
<213> ORGANISM: Piscirickettsia salmonis

<400> SEQUENCE: 65

Phe Ala Asp Val Ala Gly Cys Glu Glu Ala Lys Glu Glu Val Lys Glu
1               5                   10                  15

Leu Val Asp Phe Leu Arg Asp Pro Thr Lys Phe Gln Lys Leu Gly Gly
            20                  25                  30

Lys Ile Pro Gln Gly Val Leu Met Val Gly Pro Pro Gly Thr Gly Lys
        35                  40                  45

Thr Leu Leu Ala Lys Ala Ile Ala Gly Glu Ala Lys Val Pro Phe Phe
    50                  55                  60

Ser Ile Ser Gly Ser Asp Phe Val Glu Met Phe Val Gly Val Gly Ala
65                  70                  75                  80

Ser Arg Val Arg Asp Met Phe Asp Gln Ala Lys Lys Arg Ala Pro Cys
            85                  90                  95

Ile Ile Phe Ile Asp Glu Ile Asp Ala Val Gly Arg His Arg Gly Ser
            100                 105                 110

Gly Met Gly Gly Gly His Asp Glu Arg Glu Gln
        115                 120


<210> SEQ ID NO 66
<211> LENGTH: 123
<212> TYPE: PRT
<213> ORGANISM: Piscirickettsia salmonis

<400> SEQUENCE: 66

Phe Ala Asp Val Ala Gly Cys Glu Glu Ala Lys Glu Glu Val Lys Glu
1               5                   10                  15

Leu Val Asp Phe Leu Arg Asp Pro Thr Lys Phe Gln Lys Leu Gly Gly
            20                  25                  30

Lys Ile Pro Gln Gly Val Leu Met Val Gly Pro Pro Gly Thr Gly Lys
        35                  40                  45

Thr Leu Leu Ala Lys Ala Ile Ala Gly Glu Ala Lys Val Pro Phe Phe
    50                  55                  60

Ser Ile Ser Gly Ser Asp Phe Val Glu Met Phe Val Gly Val Gly Ala
65                  70                  75                  80

Ser Arg Val Arg Asp Met Phe Asp Gln Ala Lys Lys Arg Ala Pro Cys
```

-continued

```
                85                  90                  95

Ile Ile Phe Ile Asp Glu Ile Asp Ala Val Gly Arg His Arg Gly Ser
            100                 105                 110

Gly Met Gly Gly Gly His Asp Glu Arg Glu Gln
        115                 120


<210> SEQ ID NO 67
<211> LENGTH: 25
<212> TYPE: DNA
<213> ORGANISM: Artificial Sequence
<220> FEATURE:
<223> OTHER INFORMATION: PCR Primer: rpoD SNP Detection Forward Primer

<400> SEQUENCE: 67

ggacaatccg gattcctgta catat                                            25


<210> SEQ ID NO 68
<211> LENGTH: 19
<212> TYPE: DNA
<213> ORGANISM: Artificial Sequence
<220> FEATURE:
<223> OTHER INFORMATION: DNA probe: rpoD VProbe1-VIC Mutant Allele

<400> SEQUENCE: 68

acaagcttaa ctgcgtctc                                                   19


<210> SEQ ID NO 69
<211> LENGTH: 17
<212> TYPE: DNA
<213> ORGANISM: Artificial Sequence
<220> FEATURE:
<223> OTHER INFORMATION: DNA probe: rpoD MProbe2-FAM Wild-Type Allele

<400> SEQUENCE: 69

aagcttaacc gcgtctc                                                     17


<210> SEQ ID NO 70
<211> LENGTH: 23
<212> TYPE: DNA
<213> ORGANISM: Artificial Sequence
<220> FEATURE:
<223> OTHER INFORMATION: PCR Primer: rpoD SNP Detection Reverse Primer

<400> SEQUENCE: 70

gccgagttct tggatcattt gac                                              23


<210> SEQ ID NO 71
<211> LENGTH: 18
<212> TYPE: DNA
<213> ORGANISM: Artificial Sequence
<220> FEATURE:
<223> OTHER INFORMATION: PCR Primer: ATP-Grasp Domain Protein SNP
      Detection Forward Primer

<400> SEQUENCE: 71

tggcgatggt gcgtctac                                                    18


<210> SEQ ID NO 72
<211> LENGTH: 16
<212> TYPE: DNA
<213> ORGANISM: Artificial Sequence
<220> FEATURE:
<223> OTHER INFORMATION: DNA probe: ATP-Grasp Domain Protein VProbe1-VIC
      Mutant Allele

<400> SEQUENCE: 72
```

ccatcaggga gccgag 16

<210> SEQ ID NO 73
<211> LENGTH: 16
<212> TYPE: DNA
<213> ORGANISM: Artificial Sequence
<220> FEATURE:
<223> OTHER INFORMATION: DNA probe: ATP-Grasp Domain Protein MProbe2-FAM Wild-Type Allele

<400> SEQUENCE: 73
ccatcagaga gccgag 16

<210> SEQ ID NO 74
<211> LENGTH: 22
<212> TYPE: DNA
<213> ORGANISM: Artificial Sequence
<220> FEATURE:
<223> OTHER INFORMATION: PCR Primer: ATP-Grasp Domain Protein SNP Detection Reverse Primer

<400> SEQUENCE: 74
cgccaattgc accttgatga ag 22

<210> SEQ ID NO 75
<211> LENGTH: 24
<212> TYPE: DNA
<213> ORGANISM: Artificial Sequence
<220> FEATURE:
<223> OTHER INFORMATION: PCR Primer: FtsH SNP Detection Forward Primer

<400> SEQUENCE: 75
ccaaaagtta ggcggcaaaa ttcc 24

<210> SEQ ID NO 76
<211> LENGTH: 14
<212> TYPE: DNA
<213> ORGANISM: Artificial Sequence
<220> FEATURE:
<223> OTHER INFORMATION: DNA probe: FtsH VProbe1-VIC Mutant Allele

<400> SEQUENCE: 76
tgggccaact atca 14

<210> SEQ ID NO 77
<211> LENGTH: 14
<212> TYPE: DNA
<213> ORGANISM: Artificial Sequence
<220> FEATURE:
<223> OTHER INFORMATION: DNA probe: FtsH MProbe2-FAM Wild-Type Allele

<400> SEQUENCE: 77
tgggccaacc atca 14

<210> SEQ ID NO 78
<211> LENGTH: 24
<212> TYPE: DNA
<213> ORGANISM: Artificial Sequence
<220> FEATURE:
<223> OTHER INFORMATION: PCR Primer: FtsH SNP Detection Reverse Primer

<400> SEQUENCE: 78
gctaatagcg tcttacctgt tcca 24